United States Patent
Ohnuki et al.

(10) Patent No.: US 9,428,501 B2
(45) Date of Patent: Aug. 30, 2016

(54) BICYCLIC NITROGEN-CONTAINING AROMATIC HETEROCYCLIC AMIDE COMPOUND

(71) Applicant: ASTELLAS PHARMA INC., Tokyo (JP)

(72) Inventors: Kei Ohnuki, Tokyo (JP); Hidenori Azami, Tokyo (JP); Yuki Sawada, Tokyo (JP); Takashi Shin, Tokyo (JP); Kazuyuki Kuramoto, Tokyo (JP); Shigetoshi Kikuchi, Tokyo (JP); Tomoyuki Saito, Tokyo (JP); Hisao Hamaguchi, Tokyo (JP); Takeyuki Nagashima, Tokyo (JP)

(73) Assignee: Astellas Pharma Inc., Tokyo (JP)

(*) Notice: Subject to any disclaimer, the term of this patent is extended or adjusted under 35 U.S.C. 154(b) by 0 days.

(21) Appl. No.: 14/418,672

(22) PCT Filed: Jun. 9, 2014

(86) PCT No.: PCT/JP2014/065181
§ 371 (c)(1),
(2) Date: Jan. 30, 2015

(87) PCT Pub. No.: WO2014/199933
PCT Pub. Date: Dec. 18, 2014

(65) Prior Publication Data
US 2015/0266869 A1 Sep. 24, 2015

(30) Foreign Application Priority Data

Jun. 10, 2013 (JP) ................................. 2013-122180

(51) Int. Cl.
| | | |
|---|---|---|
| C07D 401/14 | (2006.01) | |
| C07D 471/04 | (2006.01) | |
| C07D 413/14 | (2006.01) | |
| C07D 401/12 | (2006.01) | |
| C07D 417/14 | (2006.01) | |
| A61K 31/496 | (2006.01) | |
| A61K 31/497 | (2006.01) | |
| C07D 405/14 | (2006.01) | |
| C07D 215/48 | (2006.01) | |
| C07D 401/04 | (2006.01) | |
| C07D 235/30 | (2006.01) | |
| C07D 471/14 | (2006.01) | |

(52) U.S. Cl.
CPC .......... *C07D 471/04* (2013.01); *C07D 215/48* (2013.01); *C07D 235/30* (2013.01); *C07D 401/04* (2013.01); *C07D 401/12* (2013.01); *C07D 401/14* (2013.01); *C07D 405/14* (2013.01); *C07D 413/14* (2013.01); *C07D 417/14* (2013.01); *C07D 471/14* (2013.01)

(58) Field of Classification Search
None
See application file for complete search history.

(56) References Cited

FOREIGN PATENT DOCUMENTS

| WO | 02 20008 | 3/2002 |
|---|---|---|
| WO | 2009 132136 | 10/2009 |
| WO | 2012 016217 | 2/2012 |
| WO | 2013 116491 | 8/2013 |

OTHER PUBLICATIONS

Hatoum et al. BioMed Research International, vol. 2015, pp. 1-13 (2015).*
Cancer Drug Design and Discovery, Neidle, Stephen,ed. (Elsevier/Academic Press), pp. 427-431 (2008).*
Jenkins, Y. et al., "AMPK Activation through Mitochondrial Regulation Results in Increased Substrate Oxidation and Improved Metabolic Parameters in Models of Diabetes", PLOS ONE, vol. 8, No. 12, URL: http://www.plosone.org, pp. 1-19, (2013).
International Search Report and Written Opinion of the International Searching Authority Issued Sep. 2, 2014 in PCT/JP14/065181 Filed Jun. 9, 2014.

* cited by examiner

*Primary Examiner* — Emily Bernhardt
(74) *Attorney, Agent, or Firm* — Oblon, McClelland, Maier & Neustadt, L.L.P

(57) ABSTRACT

Compounds of formula (I) and salts thereof:

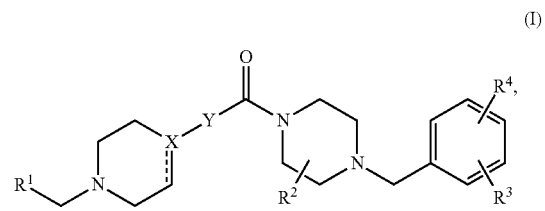

(I)

wherein the variables are defined herein, are useful for the treatment of breast cancer.

20 Claims, No Drawings

BICYCLIC NITROGEN-CONTAINING AROMATIC HETEROCYCLIC AMIDE COMPOUND

CROSS REFERENCES TO RELATED APPLICATIONS

This application is a 371 of International Patent Application No. PCT/JP14/065181, filed on Jun. 9, 2014, and claims priority to Japanese Patent Application No. 2013-122180, filed on Jun. 10, 2013.

TECHNICAL FIELD

The present invention relates to a bicyclic nitrogen-containing aromatic heterocyclic amide compound useful as an active ingredient of a pharmaceutical composition, for example, a pharmaceutical composition for treating breast cancer.

BACKGROUND ART

Breast cancer is generated when normal cells of the breast are changed by a gene mutation or by DNA damage and uncontrollably proliferated. In cancers affecting women, breast cancer has the highest incidence rate, and every year 1.3 million or more people are diagnosed with breast cancer worldwide with 450,000 or more deaths due to breast cancer (CA Cancer J Clin. 2011, 61: 69-90).

Treatment for breast cancer is broadly divided by surgery (surgical therapy), anticancer drug (hormone therapy and chemotherapy), and radiation irradiation (radiation therapy), and in many cases, treatment is performed through a combination of these methods. From gene profiling, breast cancer is classified into four subtypes, that is, (1) luminal A (hormone receptor (estrogen receptor (ER) or progesterone receptor (PR)) positive, human epidermal growth factor receptor type 2 (HER2) negative), (2) luminal B (hormone receptor positive, HER2 positive), (3) HER2 positive, and (4) triple negative in which all of ER, PR and HER2 are negative. In a case of a hormone receptor positive patient, hormone therapy such as tamoxifen and an aromatase inhibitor is performed, and in a case of a HER2 positive patient, anti HER2 therapy such as trastuzumab and lapatinib is performed. Similarly, treatment systems in accordance with the respective subtypes are established, and the concept of personalized medicines are widely used (J Clin Invest. 2011, 121: 3797-3803). On the other hand, chemotherapy is generally performed against triple negative, however there is no effective treatment at present. In addition, regarding the hormone therapy, there are not a few cases where patients have no therapeutic effect at all, or patients acquire tolerance.

From molecular biological analysis, it is reported that gene alteration of phosphatidylinositol 3-kinase (PI3K) pathway molecules occurs at high frequency in breast cancer (Breast Cancer Res. 2011, 13: 224). It is confirmed that among the gene alterations, in particular, PIK3CA mutations account for about 25% of breast cancer cases (Chin J Cancer. 2012, 31: 327-334). PIK3CA is the gene name of p110alpha which is a catalytic unit of PI3K, and a hot spot that mutations enter the helical domain and the kinase domain at high frequency is present. If the PI3K pathway is activated by these gene mutations, a serine-threonine kinase which is called Akt is subjected to phosphorylation, thereby being activated. At the downstream of Akt, a mammalian target of rapamycin (mTOR) is present. The mTOR is the serine-threonine kinase identified as a target of rapamycin, and plays a central role in the regulation of cell proliferation and survival. It is found that activation of the PI3K/Akt/mTOR pathway is extremely important as a mechanism to promote the proliferation of cancer cells (Oncologist. 2011, 16: 404-414).

It is recently reported that metformin known as a first-line drug of an agent for treating type 2 diabetes inhibits the proliferation of breast cancer cells by activating an AMP-activated protein kinase (AMPK) (Cancer Res. 2006, 66: 10269-10273). The AMPK is a highly conserved serine-threonine kinase, controls the energy metabolism in various cells, and responds by monitoring the variation of an AMP/ATP ratio in cells (Annu Rev Biochem. 1998, 67: 821-855). It is found that AMPK activation by metformin is based on a mitochondrial Complex I inhibitory effect (Diabetes Metab. 2003, 29 (4 Pt 2): 6S88-94). When an intracellular ATP level is reduced by Complex I inhibition, the AMP/ATP ratio increases, AMP is allosterically bonded to AMPK, and thus AMPK is activated. The activated AMPK inhibits a signal of mTOR through phosphorylation of a tuberous sclerosis complex 2 (TSC2) (Gene Cells. 2003, 8: 65-79). This is considered to be one of the reasons why metformin inhibits proliferation of cancer cells (Cancer Res 2007, 67: 10804-10812). From the above, it is believed that since Complex I inhibitor inhibits the PI3K/Akt/mTOR pathway, Complex I inhibitor is useful as an agent for treating breast cancer in which this pathway is activated.

As the compound having a Complex I inhibitory effect, a large number of compounds regardless of natural or non-natural compounds such as rotenone, pyridaben, bullatacin, piericidin A, capsaicin, and fenazaquin are known, and for example, it is reported that a compound of the following formula (A) has the Complex I inhibitory effect, and inhibits the proliferation of various cancer cells including breast cancer cells (Patent Document 1).

[Chem. 1]

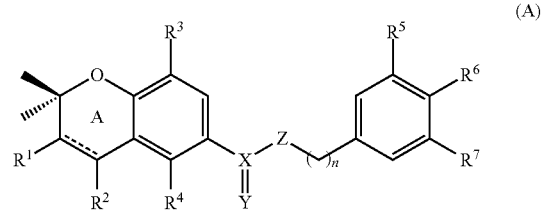

(A)

(Refer to this publication for the meanings of the symbols in the formula.)

In addition, it is reported that compounds of the following formulas (B) and (C), as an example of the compound having an AMPK activation effect, has the AMPK activation effect, and is useful for treating metabolic diseases such as type 2 diabetes, atherosclerosis, and cardiovascular disease and the like (Patent Documents 2 and 3, respectively). However, in these documents, the compound of the formula (I) of the present invention described below is not described, and there is no specific description suggesting usefulness for treatment of cancer and the like.

[Chem. 2]

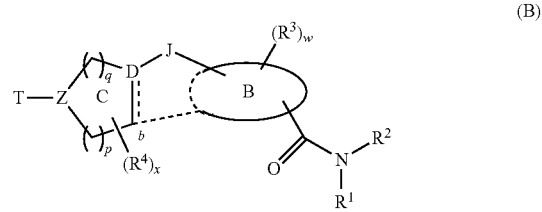

(B)

-continued

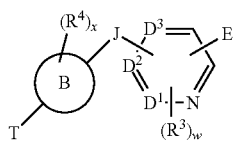
(C)

(Refer to the publication for the meanings of the symbols in the formulas.)

RELATED ART

Patent Document

[Patent Document 1] Pamphlet of International Publication No. WO02/20008
[Patent Document 2] Pamphlet of International Publication No. WO2009/132136
[Patent Document 3] Pamphlet of International Publication No. WO2012/016217

DISCLOSURE OF INVENTION

Problems to be Solved by the Invention

A compound useful as an active ingredient of a pharmaceutical composition, for example, a pharmaceutical composition for treating breast cancer is provided.

Means for Solving the Problems

As a result of intensive studies on a compound having the Complex I inhibitory effect and the AMPK activation effect, the present inventors found that a bicyclic nitrogen-containing aromatic heterocyclic amide compound of the present invention has excellent Complex I inhibitory effect and AMPK activation effect, thereby completing the present invention.

That is, the present invention relates to the compound of the formula (I) or a salt thereof, and a pharmaceutical composition containing the compound of the formula (I) or a salt thereof, and an excipient.

[Chem. 3]

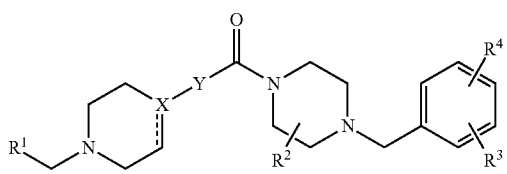
(I)

(In the formula,
$R^1$ is aryl or monocyclic nitrogen-containing heteroaryl, each of which may be substituted with group(s) selected from the group consisting of halogen, lower alkyl, —O-lower alkyl, halogeno-lower alkyl, —O-halogeno-lower alkyl, —CN, dimethylamino and cycloalkyl; X is CH, N, or C;

[Chem. 4]

is i) a single bond in a case where X is CH or N and ii) a double bond in a case where X is C;

Y is a cyclic group described below:

[Chem. 2]

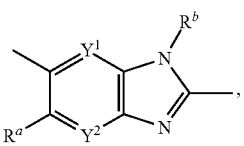
(Y-1)

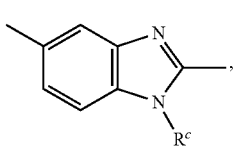
(Y-2)

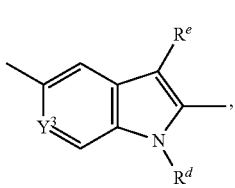
(Y-3)

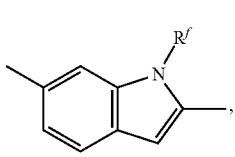
(Y-4)

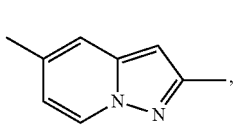
(Y-5)

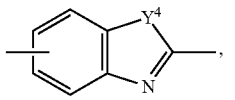
(Y-6)

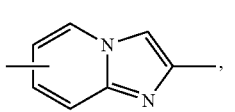
(Y-7)

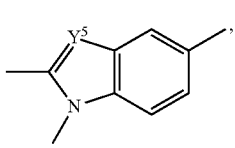
(Y-8)

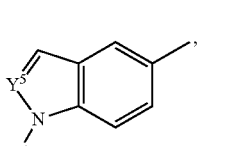
(Y-9)

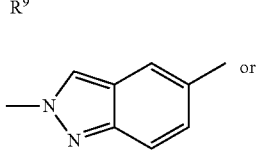
(Y-10) or

-continued

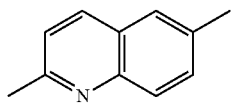
(Y-11)

here,
Y¹ is $CR^h$ or N,
Y² is $CR^i$ or N,
provided that Y¹ and Y² are not N at the same time,
$R^a$, $R^h$ and $R^i$ which are the same as or different from each other are H or halogen,
$R^b$ is H or lower alkyl,
$R^c$ is lower alkyl,
Y³ is CH or N,
$R^d$ and $R^e$ which are the same as or different from each other are H or lower alkyl,
$R^f$ is H or lower alkyl,
Y⁴ is O or S,
Y⁵ is CH or N,
Y⁶ is CH or N,
$R^g$ is H or lower alkyl;
R² is H or lower alkyl; and
R³ and R⁴ which are the same as or different from each other are H, halogen, lower alkyl, —O-lower alkyl, halogeno-lower alkyl, —O-halogeno-lower alkyl, cycloalkyl, or —CN, or R³ and R⁴ may form 2,2-difluoro-1,3-benzodioxole by joining together with the benzene ring to which R³ and R⁴ are bonded.)

In addition, unless otherwise described, in a case where the symbols in the chemical formulas in the present specification are also used in other chemical formulas, the same symbol indicates the same meaning.

In addition, the present invention relates to a pharmaceutical composition for treating breast cancer containing the compound of the formula (I) or a salt thereof. Moreover, the pharmaceutical composition includes an agent for treating breast cancer comprising the compound of the formula (I) or a salt thereof.

In addition, the present invention relates to use of the compound of the formula (I) or a salt thereof for the manufacture of the pharmaceutical composition for treating breast cancer, use of the compound of the formula (I) or a salt thereof for treating breast cancer, the compound of the formula (I) or a salt thereof for treating breast cancer, and a method for treating breast cancer comprising administering to a subject an effective amount of the compound of the formula (I) or a salt thereof. Moreover, the "subject" is a human or other animals in need of such treatment, and in an embodiment the subject is a human in need of such treatment.

Effects of the Invention

Since it was confirmed that the compound of the formula (I) or a salt thereof has an excellent Complex I inhibitory effect and AMPK activation effect, the present inventors have investigated a cell proliferation inhibitory effect and/or an anti-tumor effect of the compound of the formula (I) or a salt thereof using several human PIK3CA mutation-positive breast cancer cell lines including human PIK3CA mutation-positive breast cancer cell line MDA-MB-453 cells which is a breast cancer in which PI3K pathway is activated, and the present inventors found that in these several human PIK3CA mutation-positive breast cancer cell lines, the cell proliferation inhibitory effect and/or the anti-tumor effect is weak. Thus, the present inventors have further conducted on intensive studies on these human PIK3CA mutation-positive breast cancer cell lines, and have found that in the human PIK3CA mutation-positive breast cancer cell lines in which the compound of the formula (I) or a salt thereof exhibits a strong cell proliferation inhibitory effect and/or anti-tumor effect, MCT4 is not expressed, and focused on this. Moreover, the MCT4 is an abbreviation of monocarboxylate transporter 4, has a function to transport mainly lactic acid from the inside of a cell to the outside of a cell, and is highly expressed in tissues in which glycolysis system is enhanced, such as a white muscle (J Biol Chem. 2006; 281: 9030-9037).

In order to clarify that the compound of the formula (I) or a salt thereof exhibits a strong cell proliferation inhibitory effect and/or anti-tumor effect and a relationship with expression of MCT4 in cell lines, the present inventors have also investigated the cell proliferation inhibitory effect and/or the anti-tumor effect of the compound of the formula (I) or a salt thereof on human breast cancer cell lines which do not have any mutations of PIK3CA. As a result, it was clarified that the compound of the formula (I) or a salt thereof exhibits a strong cell proliferation inhibitory effect and/or anti-tumor effect with respect to the cells in human breast cancer cell lines in which MCT4 is not expressed, even in human breast cancer cell lines which do not have any mutation of PIK3CA.

In other words, the compound of the formula (I) or a salt thereof has an excellent Complex I inhibitory effect and the AMPK activation effect, and can be used as an agent for treating breast cancer, in particular, breast cancer in which MCT4 is not expressed, and among others, PIK3CA mutation-positive breast cancer in which MCT4 is not expressed.

EMBODIMENTS FOR CARRYING OUT THE INVENTION

Hereinafter, the present invention will be described in detail.

In the present specification, "lower alkyl" is a linear or branched alkyl having 1 to 6 carbon atoms (hereinafter, referred to as $C_{1-6}$), and examples thereof include methyl, ethyl, n-propyl, isopropyl, n-butyl, isobutyl, sec-butyl, tert-butyl, n-pentyl, and n-hexyl. In an embodiment, the "lower alkyl" is $C_{1-4}$ alkyl, and in another embodiment, is methyl or ethyl. In still another embodiment, the "lower alkyl" is methyl, and in still another embodiment, is ethyl.

"Halogen" refers to F, Cl, Br, or I. In an embodiment, "halogen" is F.

"Halogeno-lower alkyl" is $C_{1-6}$ alkyl substituted with one or more halogens. In an embodiment, the "halogeno-lower alkyl" is $C_{1-6}$ alkyl substituted with 1 to 5 halogens, and in another embodiment, is trifluoromethyl or difluoromethyl. In still another embodiment, the "halogeno-lower alkyl" is trifluoromethyl, and in still another embodiment, is difluoromethyl.

"Cycloalkyl" is a $C_{3-10}$ saturated hydrocarbon ring group, which may have a bridge. Examples thereof include cyclopropyl, cyclobutyl, cyclopentyl, cyclohexyl, cycloheptyl, cyclooctyl, and adamantyl. In an embodiment, the "cycloalkyl" is $C_{3-8}$ cycloalkyl, in another embodiment, is $C_{3-6}$ cycloalkyl, and in still another embodiment, is cyclopropyl.

"Aryl" is a $C_{6-14}$ monocyclic to tricyclic aromatic hydrocarbon ring group, examples thereof include phenyl and naphthyl, and in another embodiment, the "aryl" is phenyl.

"Monocyclic nitrogen-containing heteroaryl" is a cyclic group having one or more N as a constituent atom of a ring among 5- or 6-membered monocyclic aromatic ring groups containing 1 to 4 heteroatoms selected from O, S and N. Examples thereof include pyrrolyl, imidazolyl, pyrazolyl, oxazolyl, isoxazolyl, thiazolyl, isothiazolyl, triazolyl, oxadiazolyl, thiadiazolyl, tetrazolyl, pyridyl, pyrimidinyl, pyrazinyl, pyridazinyl, triazinyl, and tetrazinyl, and in an embodiment, the "monocyclic nitrogen-containing heteroaryl" is pyridyl, pyrazinyl, pyrazolyl, or thiadiazolyl. In another embodiment, the "monocyclic nitrogen-containing heteroaryl" is pyridyl, pyrazinyl, or pyrazolyl, and in still another embodiment, is pyridyl, pyrazinyl, or pyrimidinyl. In still another embodiment, the "monocyclic nitrogen-containing heteroaryl" is pyridyl. In still another embodiment, the "monocyclic nitrogen-containing heteroaryl" is pyrazinyl.

The compound of the formula (I) or a salt thereof in a case where —Y— in the formula (I) represents a group of the formula (Y-1) refers to a compound of the formula (I-1) or a salt thereof.

[Chem. 6]

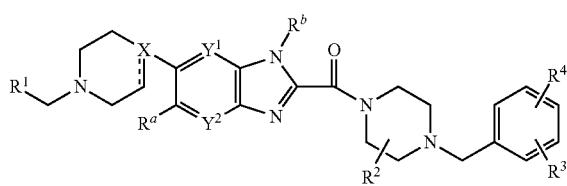

(I-1)

The compound of the formula (I) or a salt thereof in a case where —Y— in the formula (I) represents a group of the formula (Y-2) refers to a compound of the formula (I-2) or a salt thereof.

[Chem. 7]

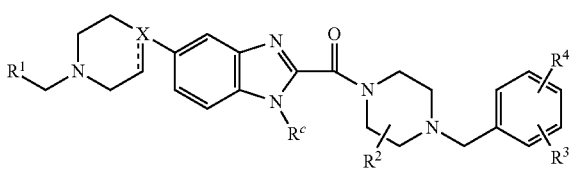

(I-2)

The compound of the formula (I) or a salt thereof in a case where —Y— in the formula (I) represents a group of the formula (Y-3) refers to a compound of the formula (I-3) or a salt thereof.

[Chem. 8]

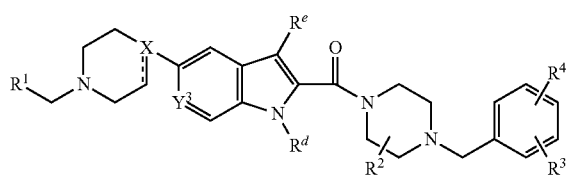

(I-3)

The compound of the formula (I) or a salt thereof in a case where —Y— in the formula (I) represents a group of the formula (Y-4) refers to a compound of the formula (I-4) or a salt thereof

[Chem. 9]

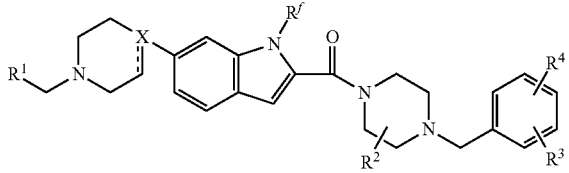

(I-4)

The compound of the formula (I) or a salt thereof in a case where —Y— in the formula (I) represents a group of the formula (Y-5) refers to a compound of the formula (I-5) or a salt thereof.

[Chem. 10]

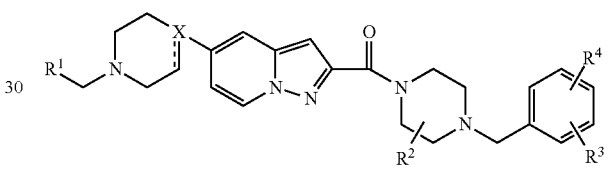

(I-5)

The compound of the formula (I) or a salt thereof in a case where —Y— in the formula (I) represents a group of the formula (Y-6) refers to a compound of the formula (I-6) or a salt thereof.

[Chem. 11]

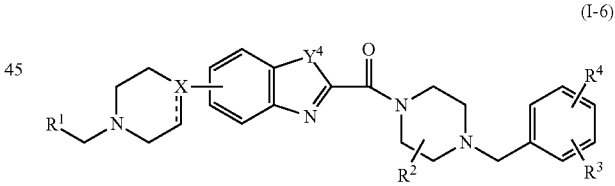

(I-6)

The compound of the formula (I) or a salt thereof in a case where —Y— in the formula (I) represents a group of the formula (Y-7) refers to a compound of the formula (I-7) or a salt thereof

[Chem. 12]

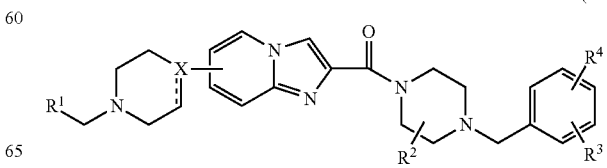

(I-7)

The compound of the formula (I) or a salt thereof in a case where —Y— in the formula (I) represents a group of the formula (Y-8) refers to a compound of the formula (I-8) or a salt thereof

[Chem. 13]

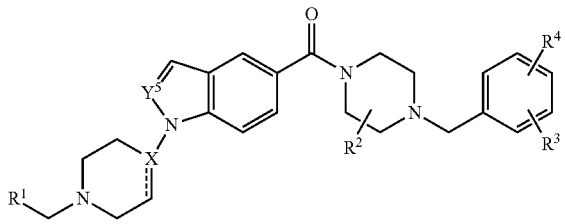

(I-8)

The compound of the formula (I) or a salt thereof in a case where —Y— in the formula (I) represents a group of the formula (Y-9) refers to a compound of the formula (I-9) or a salt thereof.

[Chem. 14]

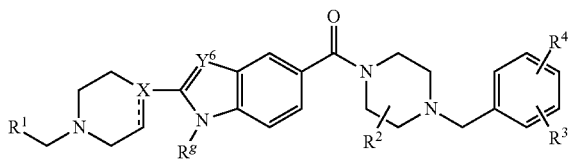

(I-9)

The compound of the formula (I) or a salt thereof in a case where —Y— in the formula (I) represents a group of the formula (Y-10) refers to a compound of the formula (I-10) or a salt thereof

[Chem. 15]

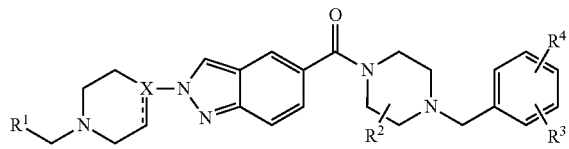

(I-10)

The compound of the formula (I) or a salt thereof in a case where —Y— in the formula (I) represents a group of the formula (Y-11) refers to a compound of the formula (I-11) or a salt thereof.

[Chem. 16]

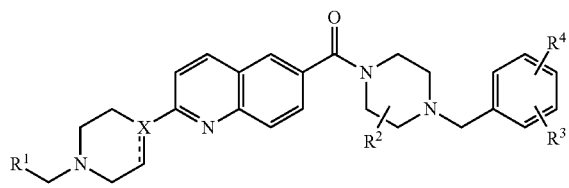

(I-11)

In the present specification, "may be substituted" means that a compound does not have a substituent, or has 1 to 5 substituents. Moreover, in a case of having a plurality of substituents, these substituents may be the same as or different from each other. In addition, cells in which "MCT4 is not expressed" mean cells which have the same expression level of MCT4 as MDA-MB-453 cells, BT-474 cells, or OCUB-M cells used in Test Example 6, or HCC1500 cells, ZR-75-30 cells, or HCC2218 cells used in Test Example 7 by methods such as a gene detection method (for example, FISH (fluorescence in situ hybridization method), PCR (polymerase chain reaction method), and the like), a messenger RNA detection method (for example, RT-PCR (Reverse Transcriptase PCR), ISH (in situ hybridization method), and the like), and a protein detection method (for example, IHC (immuno-histo-chemistry method), a western blot method, and the like), and the like.

Embodiments of the compound of the formula (I) or a salt thereof are shown below.

(1) A compound or a salt thereof in which $R^1$ is phenyl, pyridyl, pyrazinyl, pyrimidinyl or pyrazolyl, each of which may be substituted with group(s) selected from the group consisting of lower alkyl and —O-lower alkyl. In another embodiment, a compound or a salt thereof in which $R^1$ is phenyl, pyridyl, pyrazinyl or pyrimidinyl, each of which may be substituted with group(s) selected from the group consisting of lower alkyl and —O-lower alkyl. In still another embodiment, a compound or a salt thereof in which $R^1$ is phenyl, pyridyl, pyrazinyl or pyrimidinyl, each of which may be substituted with group(s) selected from the group consisting of methyl, ethyl, methoxy and ethoxy. In still another embodiment, a compound or a salt thereof in which $R^1$ is pyridyl, pyrazinyl or pyrimidinyl, each of which may be substituted with group(s) selected from the group consisting of methyl, ethyl, methoxy and ethoxy. In still another embodiment, a compound or a salt thereof in which $R^1$ is pyridyl which may be substituted with group(s) selected from the group consisting of methyl, ethyl, methoxy and ethoxy. In still another embodiment, a compound or a salt thereof in which $R^1$ is pyrazinyl which may be substituted with group(s) selected from the group consisting of methyl, ethyl, methoxy and ethoxy. In still another embodiment, a compound or a salt thereof in which $R^1$ is pyridyl or pyrazinyl, each of which is substituted with group(s) selected from the group consisting of methyl, ethyl, methoxy and ethoxy. In still another embodiment, a compound or a salt thereof in which $R^1$ is pyridyl which is substituted with group(s) selected from the group consisting of methyl, ethyl, methoxy and ethoxy. In still another embodiment, a compound or a salt thereof in which $R^1$ is pyrazinyl which is substituted with group(s) selected from the group consisting of methyl, ethyl, methoxy and ethoxy. In still another embodiment, a compound or a salt thereof in which $R^1$ is pyridyl or pyrazinyl, each of which is substituted with group(s) selected from the group consisting of methyl, methoxy and ethoxy. In still another embodiment, a compound or a salt thereof in which $R^1$ is pyridyl which is substituted with group(s) selected from the group consisting of methyl, methoxy and ethoxy. In still another embodiment, a compound or a salt thereof in which $R^1$ is pyrazinyl which is substituted with group(s) selected from the group consisting of methyl, methoxy and ethoxy.

(2) A compound or a salt thereof in which X is CH or N. In another embodiment, a compound or a salt thereof in which X is CH. In still another embodiment, a compound or a salt thereof in which X is N. In still another embodiment, a compound or a salt thereof in which X is C.

(3) A compound or a salt thereof in which Y is (Y-1), (Y-2), (Y-3), (Y-4), (Y-5), (Y-6), (Y-7) or (Y-10). In another embodiment, a compound or a salt thereof in which Y is (Y-1), (Y-2), (Y-3), (Y-4) or (Y-7). In still another embodiment, a compound or a salt thereof in which Y is (Y-1), (Y-3), (Y-4) or (Y-7). In further still another embodiment, a compound or a salt thereof in which Y is (Y-1), (Y-3) or (Y-4). In still another embodiment, a compound or a salt thereof in which Y is (Y-1). In still another embodiment, a compound or a salt thereof in which Y is (Y-3). In still another embodiment, a compound or a salt thereof in which Y is (Y-4). In still another embodiment, a compound or a salt thereof in which Y is (Y-7). As embodiments of the compound of the formula (I) or a salt thereof other than those described above, a compound or a salt thereof which is any one of the following (a) to (i) can also be exemplified.

(a) A compound or a salt thereof in which Y is

[Chem. 17]

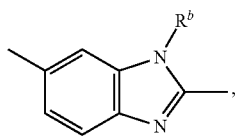 (Y-1-A)

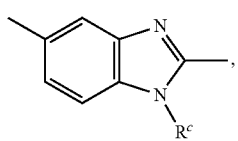 (Y-2)

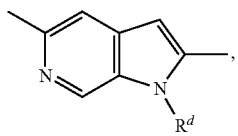 (Y-3-A)

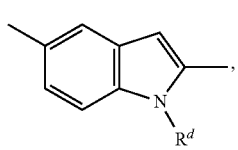 (Y-3-B)

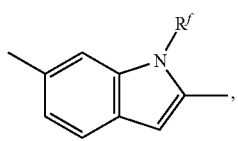 (Y-4)

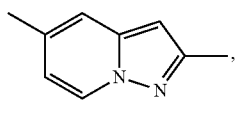 (Y-5)

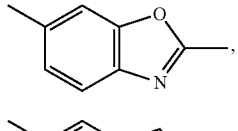 (Y-6-A)

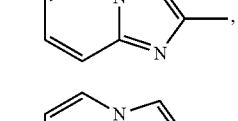 (Y-7-A)

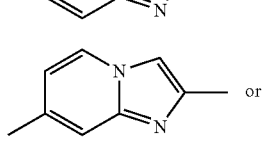 (Y-7-B)

or

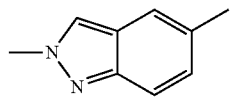 (Y-10)

(b) A compound or a salt thereof in which in the above-described (a), $R^b$ is H or methyl, $R^c$ is methyl, $R^d$ is methyl, and $R^f$ is methyl.

(c) A compound or a salt thereof in which Y is (Y-1-A), (Y-2), (Y-3-B), (Y-4) or (Y-7-B).

(d) A compound or a salt thereof in which in the above-described (c), $R^b$ is H or methyl, $R^c$ is methyl, $R^d$ is methyl, and $R^f$ is methyl.

(e) A compound or a salt thereof in which in the above-described (c), $R^b$ is H, $R^c$ is methyl, $R^d$ is methyl, and $R^f$ is methyl.

(f) A compound or a salt thereof in which in the above-described (c), $R^b$ is methyl, $R^c$ is methyl, $R^d$ is methyl, and $R^f$ is methyl.

(g) A compound or a salt thereof in which Y is (Y-1-A), (Y-3-B), (Y-4) or (Y-7-B).

(h) A compound or a salt thereof in which in the above-described (g), $R^b$ is H or methyl, $R^d$ is methyl, and $R^f$ is methyl.

(i) A compound or a salt thereof in which in the above-described (g), $R^b$ is H, $R^d$ is methyl, and $R^f$ is methyl.

(j) A compound or a salt thereof in which in the above-described (g), $R^b$ is methyl, $R^d$ is methyl, and $R^f$ is methyl.

(k) A compound or a salt thereof in which Y is (Y-1-A), (Y-3-B) or (Y-4).

(l) A compound or a salt thereof in which in the above-described (k), $R^b$ is H or methyl, $R^d$ is methyl, and $R^f$ is methyl.

(m) A compound or a salt thereof in which in the above-described (k), $R^b$ is H, $R^d$ is methyl, and $R^f$ is methyl.

(n) A compound or a salt thereof in which in the above-described (k), $R^b$ is methyl, $R^d$ is methyl, and $R^f$ is methyl.

(o) A compound or a salt thereof in which Y is (Y-1-A).

(p) A compound or a salt thereof in which in the above-described (o), $R^b$ is H or methyl.

(q) A compound or a salt thereof in which in the above-described (o), $R^b$ is H.

(r) A compound or a salt thereof in which in the above-described (o), $R^b$ is methyl.

(s) A compound or a salt thereof in which Y is (Y-3-B).

(t) A compound or a salt thereof in which in the above-described (s), $R^d$ is methyl.

(u) A compound or a salt thereof in which Y is (Y-4).

(v) A compound or a salt thereof in which in the above-described (u), $R^f$ is methyl.

(w) A compound or a salt thereof in which Y is (Y-7-B).

(4) A compound or a salt thereof in which $R^2$ is H.

(5) A compound or a salt thereof in which $R^3$ is H or halogen. In another embodiment, a compound or a salt thereof in which $R^3$ is H. In still another embodiment, a compound or a salt thereof in which $R^3$ is halogen. In still another embodiment, a compound or a salt thereof in which $R^3$ is H or F. In still another embodiment, a compound or a salt thereof in which $R^3$ is F. In still another embodiment, a compound or a salt thereof in which $R^3$ is H or 2-F (moreover, a compound in which $R^3$ is 2-F refers to a compound having F in the 2-position of a phenyl group to which $R^3$ is bonded). In still another embodiment, a compound or a salt thereof in which $R^3$ is 2-F.

(6) A compound or a salt thereof in which $R^4$ is halogeno-lower alkyl, —O-lower alkyl, or —CN. In another embodiment, a compound or a salt thereof in which $R^4$ is halogeno-lower alkyl. In still another embodiment, a compound or a salt thereof in which $R^4$ is —O-lower alkyl. In still another embodiment, a compound or a salt thereof in which $R^4$ is —CN. In still another embodiment, a compound or a salt thereof in which $R^4$ is trifluoromethyl, difluoromethyl, methoxy, or —CN. In still another embodiment, a compound or a salt thereof in which $R^4$ is trifluoromethyl, methoxy, or —CN. In still another embodiment, a compound or a salt thereof in which $R^4$ is trifluoromethyl or —CN. In still another embodiment, a compound or a salt thereof in which $R^4$ is trifluoromethyl. In still another embodiment, a compound or a salt thereof in which $R^4$ is 4-trifluoromethyl, 4-methoxy, or 4-CN. In still another embodiment, a compound or a salt thereof in which $R^4$ is 4-trifluoromethyl or 4-CN. In still another embodiment, a compound or a salt thereof in which $R^4$ is 4-CN. In still another embodiment, a compound or a salt thereof in which $R^4$ is 4-trifluoromethyl.
(7) A compound or a salt thereof in which $R^3$ is H or halogen, $R^4$ is halogeno-lower alkyl, —O-lower alkyl, or —CN, or $R^3$ and $R^4$ form 2,2-difluoro-1,3-benzodioxole by joining together with the benzene ring to which $R^3$ and $R^4$ are bonded. In another embodiment, a compound or a salt thereof in which $R^3$ is H or F, $R^4$ is trifluoromethyl, methoxy, or —CN, or $R^3$ and $R^4$ form 2,2-difluoro-1,3-benzodioxole by joining together with the benzene ring to which $R^3$ and $R^4$ are bonded. In still another embodiment, a compound or a salt thereof in which $R^3$ is H or 2-F, $R^4$ is 4-trifluoromethyl, 4-methoxy, or 4-CN, or $R^3$ and $R^4$ form 2,2-difluoro-1,3-benzodioxole by joining together with the benzene ring to which $R^3$ and $R^4$ are bonded. In still another embodiment, a compound or a salt thereof in which $R^3$ is H or 2-F, and $R^4$ is 4-trifluoromethyl or 4-CN. In still another embodiment, a compound or a salt thereof in which $R^3$ is H or 2-F, and $R^4$ is 4-trifluoromethyl. In still another embodiment, a compound or a salt thereof in which $R^3$ is H, and $R^4$ is 4-trifluoromethyl or 4-CN. In still another embodiment, a compound or a salt thereof in which $R^3$ is H, and $R^4$ is 4-trifluoromethyl. In still another embodiment, a compound or a salt thereof in which $R^3$ is H, and $R^4$ is 4-CN.
(8) The compound or salts thereof in which arbitrary two or more which are not contradictory among any embodiments of each group described in (1) to (7) are combined.

As the specific combination described in (8), the following embodiments can be exemplified.
(9) A compound or a salt thereof in which $R^2$ is H, and X is CH.
(10) A compound or a salt thereof described in (9) in which Y is (Y-1), (Y-2), (Y-3), (Y-4), (Y-5), (Y-6), (Y-7) or (Y-10).
(11) A compound or a salt thereof described in (9) in which Y is (Y-1-A), (Y-2), (Y-3-A), (Y-3-B), (Y-4), (Y-5), (Y-6-A), (Y-7-A), (Y-7-B) or (Y-10).
(12) A compound or a salt thereof described in (11) in which $R^b$ is H or methyl, $R^c$ is methyl, $R^d$ is methyl, and $R^f$ is methyl.
(13) A compound or a salt thereof described in (12) in which $R^3$ is H or halogen, $R^4$ is halogeno-lower alkyl, —O-lower alkyl, or —CN, or $R^3$ and $R^4$ form 2,2-difluoro-1,3-benzo-dioxole by joining together with the benzene ring to which $R^3$ and $R^4$ are bonded.
(14) A compound or a salt thereof described in (13) in which $R^1$ is phenyl, pyridyl, pyrazinyl, pyrimidinyl or pyrazolyl, each of which may be substituted with group(s) selected from the group consisting of lower alkyl and —O-lower alkyl.

Moreover, each compound of the formulas (I-1) to (I-11) or salt thereof is another embodiment of the compound of the formula (I) or a salt thereof.

In addition, another embodiment of the compound of the formula (I) or a salt thereof is a compound of the following formula (I-12) or a salt thereof

[Chem. 18]

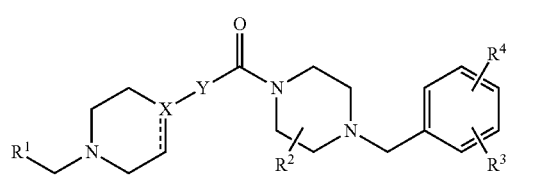

(I-12)

(In the formula,
$R^1$ is aryl or monocyclic nitrogen-containing heteroaryl, each of which may be substituted with group(s) selected from the group consisting of lower alkyl, —O-lower alkyl, and cycloalkyl;
X is CH, N, or C;

[Chem. 19]

is i) a single bond in a case where X is CH or N and ii) a double bond in a case where X is C;
Y is a cyclic group described below,

[Chem. 20]

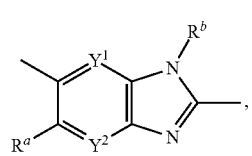

(Y-1)

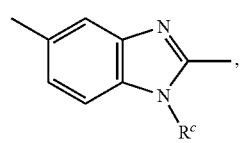

(Y-2)

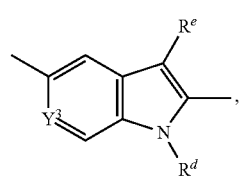

(Y-3)

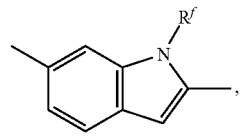

(Y-4)

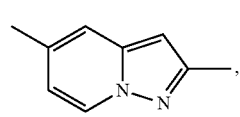

(Y-5)

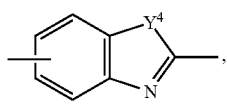 (Y-6)

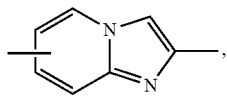 (Y-7)

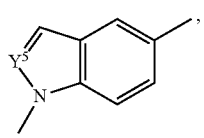 (Y-8)

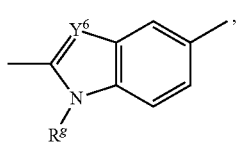 (Y-9)

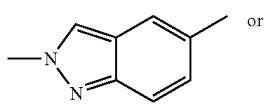 (Y-10)

or

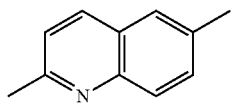 (Y-11)

here,
$Y^1$ is $CR^h$ or N,
$Y^2$ is $CR^i$ or N,
provided that $Y^1$ and $Y^2$ are not N at the same time,
$R^a$, $R^h$ and $R^i$ which are the same as or different from each other are H or halogen,
$R^b$ is H or lower alkyl,
$R^c$ is lower alkyl,
$Y^3$ is CH or N,
$R^d$ and $R^e$ which are the same as or different from each other are H or lower alkyl,
$R^f$ is H or lower alkyl,
$Y^4$ is O or S,
$Y^5$ is CH or N,
$Y^6$ is CH or N,
$R^g$ is H or lower alkyl;
$R^2$ is H or lower alkyl; and
$R^3$ and $R^4$ which are the same as or different from each other are H, halogen, halogeno-lower alkyl, or —CN, or $R^3$ and $R^4$ may form 2,2-difluoro-1,3-benzodioxole by joining together with the benzene ring to which $R^3$ and $R^4$ are bonded.)

Embodiments of a compound of the formula (I-12) or a salt thereof are shown below.

(1) A compound or a salt thereof in which $R^1$ is phenyl, pyridyl, pyrazinyl or pyrazolyl, each of which may be substituted with group(s) selected from the group consisting of lower alkyl and —O-lower alkyl. In another embodiment, a compound or a salt thereof in which $R^1$ is phenyl, pyridyl or pyrazinyl, each of which may be substituted with group(s) selected from the group consisting of lower alkyl and —O-lower alkyl. In still another embodiment, a compound or a salt thereof in which $R^1$ is phenyl, pyridyl or pyrazinyl, each of which may be substituted with group(s) selected from the group consisting of methyl, methoxy and ethoxy. In still another embodiment, a compound or a salt thereof in which $R^1$ is pyridyl or pyrazinyl, each of which may be substituted with group(s) selected from the group consisting of methyl, methoxy and ethoxy. In still another embodiment, a compound or a salt thereof in which $R^1$ is pyridyl which may be substituted with group(s) selected from the group consisting of methyl, methoxy and ethoxy. In still another embodiment, a compound or a salt thereof in which $R^1$ is pyrazinyl which may be substituted with group(s) selected from the group consisting of methyl, methoxy and ethoxy. In still another embodiment, a compound or a salt thereof in which $R^1$ is pyridyl or pyrazinyl, each of which is substituted with group(s) selected from the group consisting of methyl, methoxy and ethoxy. In still another embodiment, a compound or a salt thereof in which $R^1$ is pyridyl which is substituted with group(s) selected from the group consisting of methyl, methoxy and ethoxy. In still another embodiment, a compound or a salt thereof in which $R^1$ is pyrazinyl which is substituted with group(s) selected from the group consisting of methyl, methoxy and ethoxy. In still another embodiment, a compound or a salt thereof in which $R^1$ is pyridyl or pyrazinyl, each of which is substituted with group(s) selected from the group consisting of methyl and methoxy. In still another embodiment, a compound or a salt thereof in which $R^1$ is pyridyl which is substituted with group(s) selected from the group consisting of methyl and methoxy. In still another embodiment, a compound or a salt thereof in which $R^1$ is pyrazinyl which is substituted with group(s) selected from the group consisting of methyl and methoxy.

(2) A compound or a salt thereof in which X is CH or N. In another embodiment, a compound or a salt thereof in which X is CH. In still another embodiment, a compound or a salt thereof in which X is N. In still another embodiment, a compound or a salt thereof in which X is C.

(3) A compound or a salt thereof in which Y is (Y-1), (Y-2), (Y-3), (Y-5), (Y-6), (Y-7) or (Y-10). In another embodiment, a compound or a salt thereof in which Y is (Y-1) or (Y-7). In still another embodiment, a compound or a salt thereof in which Y is (Y-1). In still another embodiment, a compound or a salt thereof in which Y is (Y-7). As embodiments of the compound of the formula (I) or a salt thereof other than those described above, a compound or a salt thereof which is any one of the following (a) to (i) can also be exemplified.

(a) A compound or a salt thereof in which Y is

[Chem. 21]

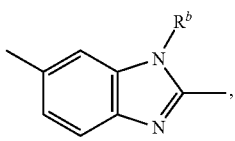 (Y-1-A)

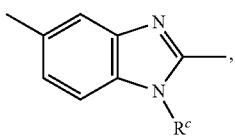 (Y-2)

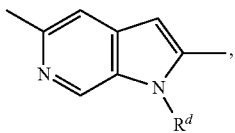 (Y-3-A)

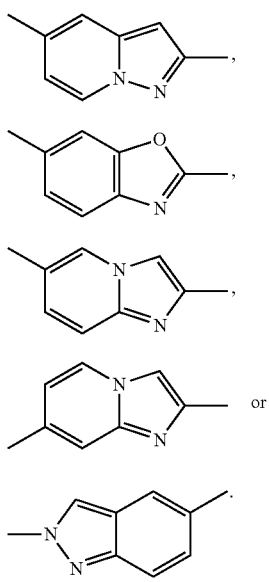

(b) A compound or a salt thereof in which in the above-described (a), $R^b$ is H or methyl, $R^c$ is methyl, and $R^d$ is methyl.
(c) A compound or a salt thereof in which Y is (Y-1-A) or (Y-7-B).
(d) A compound or a salt thereof in which in the above-described (c), $R^b$ is H.
(e) A compound or a salt thereof in which in the above-described (c), $R^b$ is methyl.
(f) A compound or a salt thereof in which Y is (Y-1-A).
(g) A compound or a salt thereof in which in the above-described (f), $R^b$ is H.
(h) A compound or a salt thereof in which in the above-described (f), $R^b$ is methyl.
(i) A compound or a salt thereof in which Y is (Y-7-B).
(4) A compound or a salt thereof in which $R^2$ is H.
(5) A compound or a salt thereof in which $R^3$ is H or halogen. In another embodiment, a compound or a salt thereof in which $R^3$ is H. In still another embodiment, a compound or a salt thereof in which $R^3$ is halogen. In still another embodiment, a compound or a salt thereof in which $R^3$ is H or F. In still another embodiment, a compound or a salt thereof in which $R^3$ is F. In still another embodiment, a compound or a salt thereof in which $R^3$ is H or 2-F (moreover, a compound in which $R^3$ is 2-F refers to a compound having F in the 2-position of a phenyl group to which $R^3$ is bonded). In still another embodiment, a compound or a salt thereof in which $R^3$ is 2-F.
(6) A compound or a salt thereof in which $R^4$ is halogeno-lower alkyl or —CN. In another embodiment, a compound or a salt thereof in which $R^4$ is halogeno-lower alkyl. In still another embodiment, a compound or a salt thereof in which $R^4$ is —CN. In still another embodiment, a compound or a salt thereof in which $R^4$ is trifluoromethyl, difluoromethyl, or —CN. In still another embodiment, a compound or a salt thereof in which $R^4$ is trifluoromethyl or —CN. In still another embodiment, a compound or a salt thereof in which $R^4$ is trifluoromethyl. In still another embodiment, a compound or a salt thereof in which $R^4$ is 4-trifluoromethyl or 4-CN. In still another embodiment, a compound or a salt thereof in which $R^4$ is 4-CN. In still another embodiment, a compound or a salt thereof in which $R^4$ is 4-trifluoromethyl.

(7) A compound or a salt thereof in which $R^3$ is H or halogen, $R^4$ is halogeno-lower alkyl or —CN, or $R^3$ and $R^4$ form 2,2-difluoro-1,3-benzodioxole by joining together with the benzene ring to which $R^3$ and $R^4$ are bonded. In another embodiment, a compound or a salt thereof in which $R^3$ is H or F, $R^4$ is trifluoromethyl or —CN, or $R^3$ and $R^4$ form 2,2-difluoro-1,3-benzodioxole by joining together with the benzene ring to which $R^3$ and $R^4$ are bonded. In still another embodiment, a compound or a salt thereof in which $R^3$ is H or 2-F, $R^4$ is 4-trifluoromethyl or 4-CN, or $R^3$ and $R^4$ form 2,2-difluoro-1,3-benzodioxole by joining together with the benzene ring to which $R^3$ and $R^4$ are bonded. In still another embodiment, a compound or a salt thereof in which $R^3$ is H or 2-F, and $R^4$ is 4-trifluoromethyl or 4-CN. In still another embodiment, a compound or a salt thereof in which $R^3$ is H or 2-F, and $R^4$ is 4-trifluoromethyl. In still another embodiment, a compound or a salt thereof in which $R^3$ is H, and $R^4$ is 4-trifluoromethyl. In still another embodiment, a compound or a salt thereof in which $R^3$ is H, and $R^4$ is 4-CN.
(8) The compound or salts thereof in which arbitrary two or more which are not contradictory among any embodiments of each group described in (1) to (7) are combined.
As the specific combination described in (8), the following embodiments can be exemplified.
(9) A compound or a salt thereof in which $R^2$ is H, and X is CH.
(10) A compound or a salt thereof described in (9) in which Y is (Y-1), (Y-2), (Y-3), (Y-5), (Y-6), (Y-7) or (Y-10).
(11) A compound or a salt thereof described in (10) in which Y is (Y-1-A), (Y-2), (Y-3-A), (Y-5), (Y-6-A), (Y-7-A), (Y-7-B) or (Y-10).
(12) A compound or a salt thereof described in (11) in which $R^b$ is H or methyl, $R^c$ is methyl, and $R^d$ is methyl.
(13) A compound or a salt thereof described in (12) in which $R^3$ is H or halogen, $R^4$ is halogeno-lower alkyl or —CN, or $R^3$ and $R^4$ form 2,2-difluoro-1,3-benzodioxole by joining together with the benzene ring to which $R^3$ and $R^4$ are bonded.
(14) A compound or a salt thereof described in (13) in which $R^1$ is phenyl, pyridyl, pyrazinyl or pyrazolyl, each of which may be substituted with group(s) selected from the group consisting of lower alkyl and —O-lower alkyl.
As the specific compounds included in the present invention, in an embodiment, <Compound of Compound group G1> or a salt thereof can be exemplified. In another embodiment, <Compound of Compound group G2> or a salt thereof can be exemplified.
<Compound of Compound Group G1>:
(5-{1-[(6-methoxypyridin-3-yl)methyl]piperidin-4-yl}-1H-benzimidazol-2-yl){4-[4-(trifluoromethyl)benzyl]piperazin-1-yl}methanone,
(5-{1-[(5-methoxypyrazin-2-yl)methyl]piperidin-4-yl}-1H-benzimidazol-2-yl){4-[4-(trifluoromethyl)benzyl]piperazin-1-yl}methanone,
(6-{1-[(5-methylpyrazin-2-yl)methyl]piperidin-4-yl}-1H-benzimidazol-2-yl){4-[4-(trifluoromethyl)benzyl]piperazin-1-yl}methanone,
(7-{1-[(6-methoxypyridin-3-yl)methyl]piperidin-4-yl}imidazo[1,2-a]pyridin-2-yl){4-[4-(trifluoromethyl)benzyl]piperazin-1-yl}methanone,
4-({4-[(5-{1-[(5-ethoxypyrazin-2-yl)methyl]piperidin-4-yl}-1-methyl-1H-indol-2-yl)carbonyl]piperazin-1-yl}methyl)benzonitrile,
4-({4-[(6-{1-[(5-ethoxypyrazin-2-yl)methyl]piperidin-4-yl}-1-methyl-1H-indol-2-yl)carbonyl]piperazin-1-yl}methyl)benzonitrile, 4-({4-[(5-{1-[(5-methoxypyrazin-2-yl)methyl]piperidin-4-yl}-1-methyl-1H-indol-2-yl)carbonyl]piperazin-1-yl}methyl)benzonitrile,
{6-[1-(4-methoxybenzyl)piperidin-4-yl]-1H-benzimidazol-2-yl}{4-[4-(trifluoromethyl)benzyl]piperazin-1-yl}methanone,
(6-{1-[(6-methoxypyridin-3-yl)methyl]piperidin-4-yl}-1-methyl-1H-benzimidazol-2-yl){4-[4-(trifluoromethyl)benzyl]piperazin-1-yl}methanone,
(5-{1-[(6-methoxypyridin-3-yl)methyl]piperidin-4-yl}-1-methyl-1H-benzimidazol-2-yl){4-[4-(trifluoromethyl)benzyl]piperazin-1-yl}methanone,
4-({4-[(6-{1-[(6-methoxypyridin-3-yl)methyl]piperidin-4-yl}-1H-benzimidazol-2-yl)carbonyl]piperazin-1-yl}methyl)benzonitrile,
(6-{1-[(6-methoxypyridin-3-yl)methyl]piperidin-4-yl}imidazo[1,2-a]pyridin-2-yl){4-[4-(trifluoromethyl)benzyl]piperazin-1-yl}methanone,
{4-[(2,2-difluoro-1,3-benzodioxol-5-yl)methyl]piperazin-1-yl}(6-{1-[(6-methoxypyridin-3-yl)methyl]piperidin-4-yl}-1H-benzimidazol-2-yl)methanone,
{4-[2-fluoro-4-(trifluoromethyl)benzyl]piperazin-1-yl}(6-{1-[(6-methoxypyridin-3-yl)methyl]piperidin-4-yl}-1H-benzimidazol-2-yl)methanone,
(5-{1-[(6-methoxypyridin-3-yl)methyl]piperidin-4-yl}-1-methyl-1H-pyrrolo[2,3-c]pyridin-2-yl){4-[4-(trifluoromethyl)benzyl]piperazin-1-yl}methanone,
(5-{1-[(6-methoxypyridin-3-yl)methyl]piperidin-4-yl}pyrazolo[1,5-a]pyridin-2-yl){4-[4-(trifluoromethyl)benzyl]piperazin-1-yl}methanone,
(5-{1-[(5-methoxypyrazin-2-yl)methyl]piperidin-4-yl}pyrazolo[1,5-a]pyridin-2-yl){4-[4-(trifluoromethyl)benzyl]piperazin-1-yl}methanone,
(2-{1-[(6-methoxypyridin-3-yl)methyl]piperidin-4-yl}-2H-indazol-5-yl){4-[4-(trifluoromethyl)benzyl]piperazin-1-yl}methanone, and
(2-{1-[(5-ethoxypyrazin-2-yl)methyl]piperidin-4-yl}-2H-indazol-5-yl){4-[4-(trifluoromethyl)benzyl]piperazin-1-yl}methanone.

<Compound of Compound group G2>:
(5-{1-[(6-methoxypyridin-3-yl)methyl]piperidin-4-yl}-1H-benzimidazol-2-yl){4-[4-(trifluoromethyl)benzyl]piperazin-1-yl}methanone,
(5-{1-[(5-methoxypyrazin-2-yl)methyl]piperidin-4-yl}-1H-benzimidazol-2-yl){4-[4-(trifluoromethyl)benzyl]piperazin-1-yl}methanone,
(6-{1-[(5-methylpyrazin-2-yl)methyl]piperidin-4-yl}-1H-benzimidazol-2-yl){4-[4-(trifluoromethyl)benzyl]piperazin-1-yl}methanone,
(7-{1-[(6-methoxypyridin-3-yl)methyl]piperidin-4-yl}imidazo[1,2-a]pyridin-2-yl){4-[4-(trifluoromethyl)benzyl]piperazin-1-yl}methanone,
4-({4-[(5-{1-[(5-ethoxypyrazin-2-yl)methyl]piperidin-4-yl}-1-methyl-1H-indol-2-yl)carbonyl]piperazin-1-yl}methyl)benzonitrile,
4-({4-[(6-{1-[(5-ethoxypyrazin-2-yl)methyl]piperidin-4-yl}-1-methyl-1H-indol-2-yl)carbonyl]piperazin-1-yl}methyl)benzonitrile, and
4-({4-[(5-{1-[(5-methoxypyrazin-2-yl)methyl]piperidin-4-yl}-1-methyl-1H-indol-2-yl)carbonyl]piperazin-1-yl}methyl)benzonitrile.

In the compound of the formula (I), tautomers or geometric isomers may be present depending on the types of substituents. In the present specification, the compound of the formula (I) is described as only one form of isomers, however the present invention also includes other isomers thereof, and also includes separated isomers or a mixture thereof.

Specifically, in a case where in the formula (I-1), $R^b$ is H, and in a case where in the formula (I-9), $Y^6$ is N and $R^g$ is H, tautomers as shown in the following formula may be present. In the present specification, any one of tautomers is described for the sake of convenience, however the present invention also includes other tautomers thereof.

[Chem. 22]

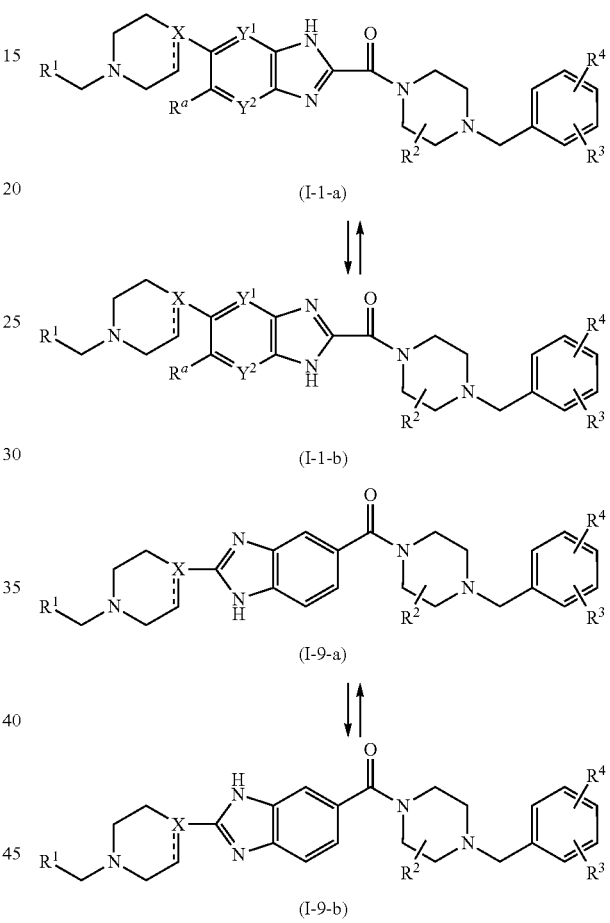

(I-1-a)

(I-1-b)

(I-9-a)

(I-9-b)

In addition, the compound of the formula (I) may have asymmetric carbon atoms or axial asymmetry, and optical isomers based on this can be present. The present invention also includes separated optical isomers of the compound of the formula (I) or a mixture thereof.

Furthermore, the present invention also includes a pharmaceutically acceptable prodrug of a compound represented by the formula (I). The pharmaceutically acceptable prodrug is a compound having a group which can be converted into an amino group, a hydroxyl group, a carboxyl group, or the like by solvolysis or under physiological conditions. As the group forming the prodrug, groups described in Prog. Med., 5, 2157-2161 (1985), and "Development of Pharmaceutical Products" (Hirokawa Publishing Company), 1990, vol. 7, Molecular Design p. 163-198 are exemplified.

In addition, a salt of the compound of the formula (I) is a pharmaceutically acceptable salt of the compound of the formula (I), and an acid addition salt or a salt with a base may be formed depending on the types of substituents. Specifically, acid addition salts of inorganic acids such as hydrochloric acid, hydrobromic acid, hydroiodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methane sulfonic acid, ethane sulfonic acid, benzene sulfonic acid, p-toluene sulfonic acid (tosic acid), aspartic acid, and glutamic acid, salts of inorganic bases such as sodium, potassium, magnesium, calcium, and aluminum, organic bases such as methylamine, ethylamine, ethanolamine, lysine, and ornithine, salts of various amino acids and amino acid derivatives such as acetylleucine and the like, and ammonium salt are exemplified.

Furthermore, the present invention also includes various hydrates or solvates of the compound of the formula (I) and a salt thereof, and crystal polymorphism substances. In addition, the present invention also includes compounds labeled with various radioactive or non-radioactive isotopes.

(Preparation Method)

The compound of the formula (I) and a salt thereof can be prepared by applying various known synthetic methods using the characteristics based on the basic structure thereof or the types of substituents. At that time, it may be effective in a preparation technology that the functional group is substituted with a suitable protecting group (group which can be easily converted into a functional group) at the stage from a starting material to an intermediate depending on the types of functional groups. As such a protecting group, the protective groups described in "Greene's Protective Groups in Organic Synthesis (4th edition, 2006)" written by P. G. M. Wuts and T. W. Greene can be exemplified, and these may be suitably selected and used depending on the reaction conditions. In such a method, first, the protecting group is introduced, a reaction is carried out, and the protecting group is removed, if necessary. By doing this, it is possible to obtain a desired compound.

In addition, the prodrug of the compound of the formula (I) can be prepared by further carrying out the reaction by introducing a specific group at the stage from a starting material to an intermediate in the same manner as the above-described protecting group, or using the obtained compound of the formula (I). The reaction can be carried out by applying known methods in the related art such as general esterification, amidation, or dehydration.

Hereinafter, representative preparation methods of the compound of the formula (I) will be described. Each preparation process can also be carried out with reference to references described in the description. Moreover, the preparation method of the present invention is not limited to examples described below.

(First Preparation Method)

[Chem. 23]

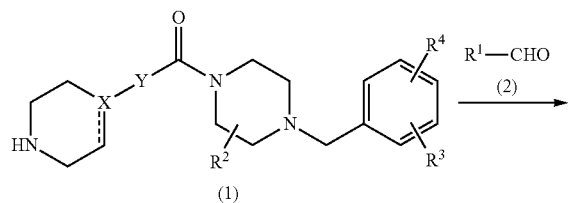

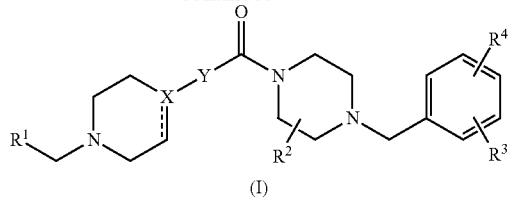

The compound of the formula (I) can be obtained by a reaction of a compound (1) and a compound (2).

In this reaction, the compound (1) and the compound (2) are used in equivalent amounts, or either thereof in an excess amount, and the mixture thereof is stirred in a range from −45° C. to heating to reflux, preferably at a temperature from 0° C. to room temperature, usually for 0.1 hours to 5 days, in a solvent which is inert to the reaction, in the presence of a reductant. Examples of the solvent used in this reaction, which are not particularly limited, include alcohols such as methanol and ethanol, ethers such as diethylether, tetrahydrofuran (THF), dioxane, and dimethoxyethane, halogenated hydrocarbons such as dichloromethane, 1,2-dichloroethane, and chloroform, and a mixture thereof. Examples of the reductant include sodium cyanoborohydride, sodium triacetoxyborohydride, and sodium borohydride. The reaction may be preferably carried out in the presence of a dehydrating agent such as molecular sieves, or an acid such as acetic acid, hydrochloric acid, and titanium (IV) isopropoxide complex.

REFERENCES

"Comprehensive Organic Functional Group Transformations II" written by A. R. Katritzky and R. J. K. Taylor, 2nd edition, Elsevier Pergamon, 2005

"Courses in Experimental Chemistry" (5th edition) edited by The Chemical Society of Japan, vol. 14 (2005) (Maruzen Co., Ltd.)

(Preparation Method 2)

[Chem. 24]

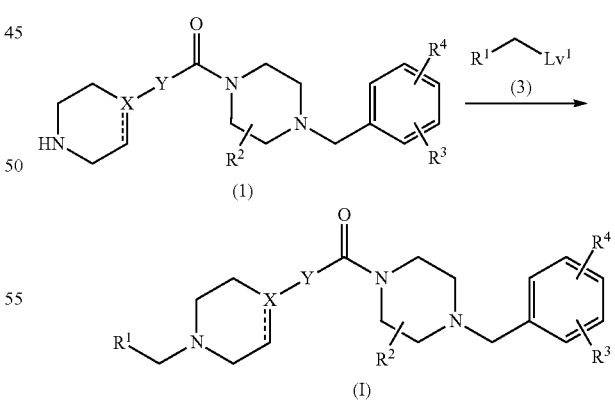

(In the formula, $Lv^1$ represents a leaving group.)

The compound of the formula (I) can be obtained by a reaction of a compound (1) and a compound (3). Examples of the leaving group of $Lv^1$ include halogen, a methanesulfonyloxy group, and a p-toluenesulfonyloxy group.

In this reaction, the compound (1) and the compound (3) are used in equivalent amounts, or either thereof in an excess amount, and the mixture thereof is stirred in a range from cooling to heating to reflux, preferably at a temperature from 0° C. to 80° C., usually for 0.1 hours to 5 days, in a solvent which is inert to the reaction or in the absence of a solvent. Examples of the solvent used in this reaction, which are not particularly limited, include aromatic hydrocarbons such as benzene, toluene, and xylene, ethers such as diethylether, tetrahydrofuran (THF), dioxane, and dimethoxyethane, halogenated hydrocarbons such as dichloromethane, 1,2-dichloroethane, and chloroform, N,N-dimethylformamide (DMF), dimethyl sulfoxide, ethyl acetate, acetonitrile, and a mixture thereof. In some cases, it is advantageous for smooth progress of the reaction to carry out the reaction in the presence of organic bases such as triethylamine, N,N-diisopropylethylamine, and N-methylmorpholine, or inorganic bases such as potassium carbonate, sodium carbonate, and potassium hydroxide.

REFERENCES

"Organic Functional Group Preparations" written by S. R. Sandler and W. Karo, 2nd edition, vol. 1, Academic Press Inc., 1991

"Courses in Experimental Chemistry" (5th edition) edited by The Chemical Society of Japan, vol. 14 (2005) (Maruzen Co., Ltd.)

In the above preparation methods, a starting compound can be prepared by using, for example, the methods below, the methods described in Preparation Examples described later, known methods, or modified methods thereof.

(Starting Material Synthesis 1-1)

[Chem. 25]

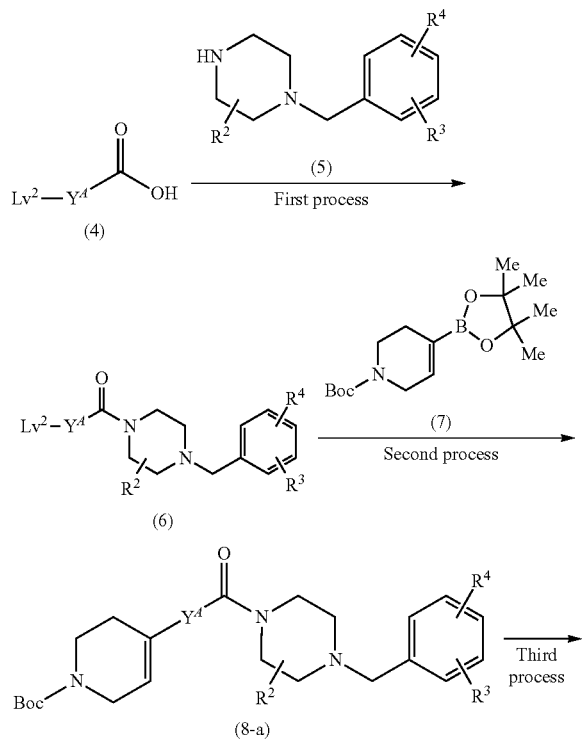

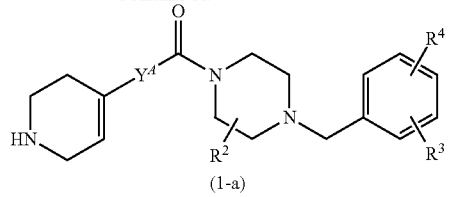

(In the formula, $Y^A$ refers to a group of which C atom constituting a ring in Y in the compound of the formula (I) is bonded to X, $Lv^2$ refers to a leaving group which is bonded to C atom constituting a ring of $Y^A$, Me refers to methyl, and Boc refers to tert-butoxycarbonyl. The same shall apply hereinafter).

The preparation method is a method in which X is bonded to C atom constituting a ring in Y in a starting compound (1) in the first preparation method and the second preparation method, and a compound (1-a) of which X is C is prepared. Here, examples of the leaving group of $Lv^2$ include halogen, methanesulfonyloxy, p-toluenesulfonyloxy, and trifluoromethanesulfonyloxy groups.

(First Process)

This process is a process in which a compound (6) is obtained by subjecting a compound (4) and a compound (5) to an amidation reaction.

In this reaction, the compound (4) and the compound (5) are used in equivalent amounts, or either thereof in an excess amount, and the mixture thereof is stirred in a range from cooling to heating, preferably at a temperature from −20° C. to 60° C., usually for 0.1 hours to 5 days, in a solvent which is inert to the reaction, in the presence of a condensing agent. Examples of the solvent used in this reaction, which are not particularly limited, include aromatic hydrocarbons such as benzene, toluene, and xylene, halogenated hydrocarbons such as dichloromethane, 1,2-dichloroethane, or chloroform, ethers such as diethylether, tetrahydrofuran (THF), dioxane, dimethoxyethane, N,N-dimethylformamide (DMF), dimethyl sulfoxide, ethyl acetate, acetonitrile, or water, and a mixture thereof. Examples of the condensing agent include N-[3-(dimethylamino)propyl]-N'-ethylcarbodiimide or a hydrochloride thereof, dicyclohexylcarbodiimide, 1,1'-carbonyldiimidazole, diphenylphosphoryl azide, phosphorus oxychloride, and the condensing agent is not limited thereto. It may be preferable for the reaction to use an additive (for example, 1H-benzotriazol-1-ol) in some cases. In some cases, it is advantageous for smooth progress of the reaction to carry out the reaction in the presence of organic bases such as triethylamine, N,N-diisopropylethylamine, and N-methylmorpholine, or inorganic bases such as potassium carbonate, sodium carbonate, and potassium hydroxide.

In addition, it is also possible to use a method in which carboxylic acid (4) is converted to a reactive derivative thereof and then reacted with amine (5). Examples of the reactive derivative of carboxylic acid include acid halides obtained by a reaction with a halogenating agent such as phosphorus oxychloride and thionyl chloride, and mixed acid anhydrides obtained by a reaction with isobutyl chloroformate, and active esters obtained by condensation with 1H-benzotriazol-1-ol. The reaction of these reactive derivatives with the compound (5) can be carried out in a range from cooling to heating, and preferably from −20° C. to 60° C., in a solvent which is inert to the reaction such as halogenated hydrocarbons, aromatic hydrocarbons, and ethers, and in some cases, it is advantageous for smooth progress of the reaction to carry out the reaction in the presence of organic bases such as triethylamine, N,N-diisopropylethylamine, and N-methylmorpholine.

REFERENCES

"Organic Functional Group Preparations" written by S. R. Sandler and W. Karo, 2nd edition, vol. 1, Academic Press Inc., 1991
"Courses in Experimental Chemistry" (5th edition)" edited by The Chemical Society of Japan, vol. 16 (2005) (Maruzen Co., Ltd.)

(Second Process)

This process is a process in which a compound (8-a) is obtained by subjecting a compound (6) and a compound (7) to a coupling reaction.

In this reaction, the compounds (6) and (7) are used in equivalent amounts, or either thereof in an excess amount, and the mixture thereof is stirred in a range from room temperature to heating to reflux, usually for 0.1 hours to 5 days, in a solvent which is inert to the reaction, in the presence of a base and a palladium catalyst. This reaction is preferably carried out in an inert gas atmosphere. Examples of the solvent used in this reaction, which are not particularly limited, include aromatic hydrocarbons such as benzene, toluene, and xylene, ethers such as diethylether, tetrahydrofuran (THF), dioxane, and dimethoxyethane, halogenated hydrocarbons such as dichloromethane, 1,2-dichloroethane, and chloroform, alcohols such as methanol, ethanol, 2-propanol, and butanol, N,N-dimethylformamide (DMF), dimethyl sulfoxide, water, and a mixed solvent thereof. Preferred examples of the base include inorganic bases such as sodium carbonate, potassium carbonate, and sodium hydroxide. As the palladium catalyst, tetrakis(triphenylphosphine)palladium, dichlorobis(triphenylphosphine)palladium, [1,1'-bis(diphenylphosphino)ferrocene]palladium chloride, and dichlorobis[di-tert-butyl(4-dimethylaminophenyl)phosphine]palladium are preferable.

REFERENCES

"Metal-Catalyzed Cross-Coupling Reactions" edited by A. d. Meijere and F. Diederich, 1st edition, VCH Publishers Inc., 1997
"Courses in Experimental Chemistry" (5th edition) edited by The Chemical Society of Japan, vol. 13 (2005) (Maruzen Co., Ltd.)

(Third Process)

This process is a process in which a compound (1-a) is obtained by subjecting a compound (8-a) to a Boc-removal reaction. This reaction, for example, can be carried out by a method described in "Greene's Protective Groups in Organic Synthesis (4th edition, 2006)" written by P. G. M. Wuts and T. W. Greene.

(Starting Material Synthesis 1-2)

[Chem. 26]

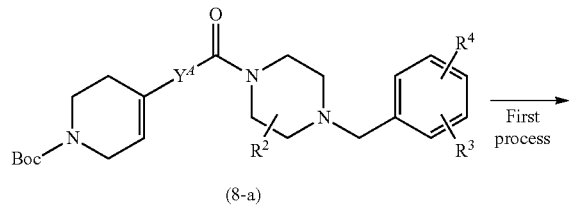

(8-a)

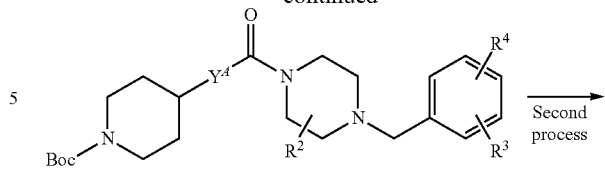

(8-b)

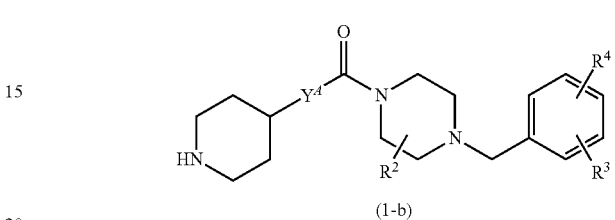

(1-b)

The preparation method is a method in which X is bonded to C atom constituting a ring in Y in a starting compound (1) in the first preparation method and the second preparation method, and a compound (1-b) of which X is CH is prepared.

(First Process)

This process is a process in which a compound (8-b) is obtained by subjecting a compound (8-a) to a hydrogenation reaction.

In this reaction, the compound (8-a) is stirred usually for 1 hour to 5 days, in a solvent which is inert to the reaction, in the presence of a metal catalyst, in a hydrogen atmosphere. This reaction is usually carried out in a range from cooling to heating, and preferably at a temperature from room temperature to 60° C. Examples of the solvent used in this reaction, which are not particularly limited, include alcohols such as methanol, ethanol, and 2-propanol, ethers such as diethylether, tetrahydrofuran (THF), dioxane, and dimethoxyethane, water, ethyl acetate, N,N-dimethylformamide (DMF), dimethyl sulfoxide, and a mixture thereof. As the metal catalyst, palladium catalysts such as palladium on carbon, palladium black, and palladium hydroxide, platinum catalysts such as platinum plate, platinum oxide, nickel catalysts such as reduced nickel and Raney nickel, rhodium catalysts such as chloro(triphenylphosphine)rhodium, or iron catalysts such as reduced iron can be appropriately used. Instead of hydrogen gas, formic acid or ammonium formate can also be used in equivalent amounts to an excess amount with respect to the compound (8-a).

REFERENCES

"Reductions in Organic Chemistry, 2nd edition (ACS Monograph: 188)" written by M. Hudlicky, ACS, 1996
"Courses in Experimental Chemistry" (5th edition) edited by The Chemical Society of Japan, vol. 19 (2005) (Maruzen Co., Ltd.)

(Second Process)

This process is a process in which a compound (1-b) is obtained by subjecting a compound (8-b) to a Boc-removal reaction. The reaction can be carried out according to the third process of Starting Material Synthesis 1-1.

(Starting Material Synthesis 1-3)

[Chem. 27]

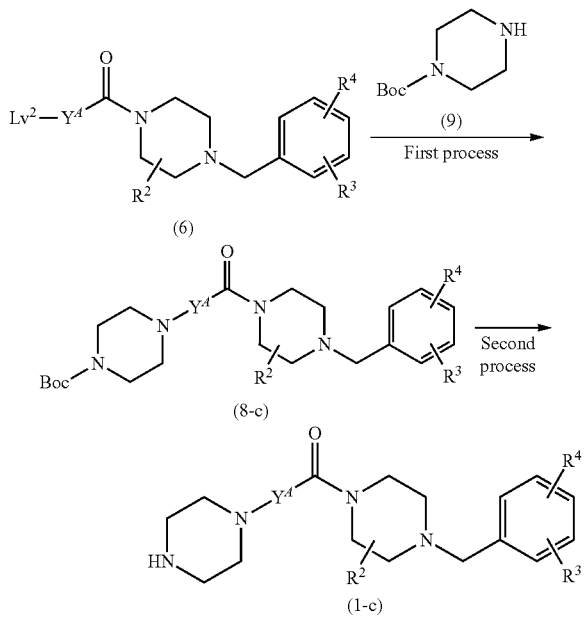

The preparation method is a method in which X is bonded to C atom constituting a ring in Y in a starting compound (1) in the first preparation method and the second preparation method, and a compound (1-c) of which X is N is prepared.

(First Process)

This process is a process in which a compound (8-c) is obtained by carrying out a substitution reaction or a coupling reaction with a compound (9) based on a difference in reactivity of the compound (6).

In a case where the reactivity of the compound (6) is relatively high as in a case where $Lv^2$ is bonded to C atom of —C=N— structure in $Y^1$, it is possible to obtain the compound (8-c) by a substitution reaction with the compound (9). This reaction can be carried out in the same manner as in the second preparation method.

In addition, in a case where the reactivity of the compound (6) is relatively low, it is possible to obtain the compound (8-c) by a coupling reaction with the compound (9). In this reaction, the compound (6) and the compound (9) are used in equivalent amounts, or either thereof in an excess amount, and the mixture thereof is stirred in a range from room temperature to heating to reflux, usually for 0.1 hours to 5 days, in a solvent which is inert to the reaction or in the absence of a solvent, in the presence of a predetermined catalyst. This reaction is preferably carried out in an inert gas atmosphere. Examples of the solvent used in this reaction, which are not particularly limited, include aromatic hydrocarbons such as benzene, toluene, and xylene, ethers such as diethylether, tetrahydrofuran (THF), dioxane, and dimethoxyethane, halogenated hydrocarbons such as dichloromethane, 1,2-dichloroethane, and chloroform, N-methylpyrrolidone, N,N-dimethylformamide (DMF), N,N-dimethylacetamide, dimethyl sulfoxide, ethyl acetate, acetonitrile, tert-butyl alcohol, and a mixture thereof. Examples of the predetermined catalyst include palladium acetate, tris(dibenzylideneacetone)dipalladium, and (2-dicyclohexylphosphino-2',6'-diisopropoxy-1,1'-biphenyl)[2-(2-aminoethyl)phenyl]palladium chloride tert-butyl methyl ether adduct. In addition, in a case using a palladium catalyst, as a ligand thereof, triphenylphosphine, 1,1'-binaphthalene-2,2'-diylbis(diphenylphosphine), 2-(dicyclohexylphosphino)-2',4',6'-triisopropyl-1,1'-biphenyl, 4,5-bis(diphenylphosphino)-9,9-dimethylxanthene, dicyclohexyl (2',6'-diisopropoxybiphenyl-2-yl)phosphine may also be used. In addition, in some cases, it is advantageous for smooth progress of the reaction to carry out the reaction in the presence of organic bases such as triethylamine, N,N-diisopropylethylamine or N-methylmorpholine, inorganic bases such as potassium carbonate, sodium carbonate, cesium carbonate or potassium hydroxide, sodium tert-butoxide, or lithium hexamethyldisilazide. In some cases, it is advantageous for smooth progress of the reaction to heat the reaction mixture by microwave irradiation.

REFERENCES

"Organic Functional Group Preparations" written by S. R. Sandler and W. Karo, 2nd edition, vol. 1, Academic Press Inc., 1991

"Courses in Experimental Chemistry" (5th edition)" edited by The Chemical Society of Japan, vol. 14 (2005) (Maruzen Co., Ltd.)

(Second Process)

This process is a process in which a compound (1-c) is obtained by subjecting the compound (8-c) to a Boc-removal reaction. The reaction can be carried out according to the third process of Starting Material Synthesis 1-1.

(Starting Material Synthesis 2)

[Chem. 28]

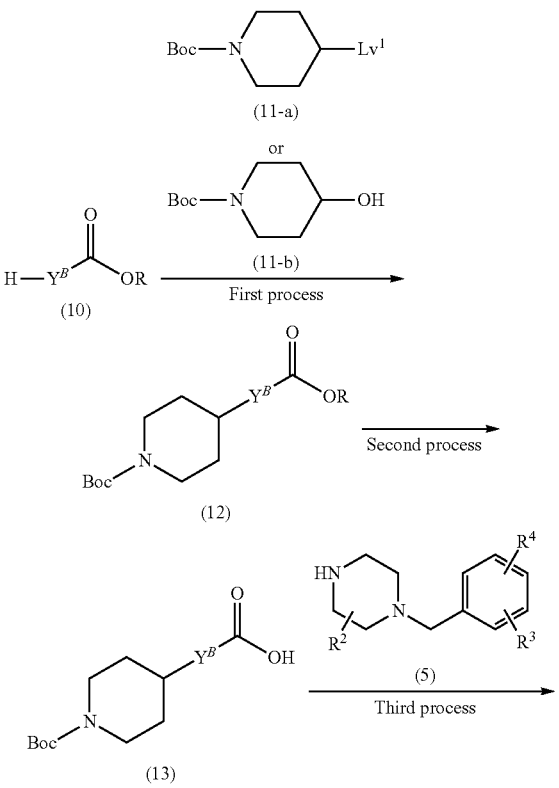

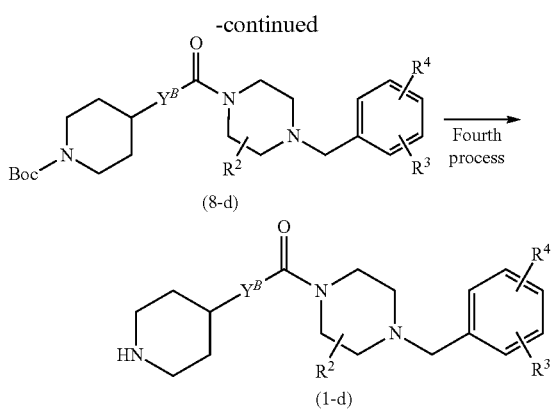

(In the formula, $Y^B$ refers to a group of which N atom constituting a ring in Y in the compound of the formula (I) is bonded to X, and R refers to lower alkyl. Moreover, H in a compound (10) is bonded to N atom which constitutes a ring in $Y^B$, and is bonded to C atom at a 4-position of a piperidine ring in a compound (1-d).)

The preparation method is a method in which X is bonded to N atom constituting a ring in Y in a starting compound (1) in the first preparation method and the second preparation method, and a compound (1-d) of which X is CH is prepared.

(First Process)

This process is a process in which a compound (12) is obtained by an alkylation reaction of a compound (10) and a compound (11-a), or a Mitsunobu reaction of the compound (10) and a compound (11-b).

The alkylation reaction of this process can be carried out according to the second preparation method.

In addition, in the Mitsunobu reaction of this process, the compounds (10) and (11-b) are used in equivalent amounts, or either thereof in an excess amount, and the mixture thereof is stirred in a range from room temperature to heating to reflux, usually for 0.1 hours to 5 days, in a solvent which is inert to the reaction such as toluene, in the presence of cyanomethylenetributyl phosphorane.

(Second Process)

This process is a process in which a compound (13) is obtained by subjecting a compound (12) to a hydrolysis reaction. This reaction, for example, can be carried out by a method described in "Greene's Protective Groups in Organic Synthesis (4th edition, 2006)" written by P. G. M. Wuts and T. W. Greene.

(Third Process)

This process is a process in which a compound (8-d) is obtained by subjecting a compound (13) and the compound (5) to an amidation reaction. The reaction can be carried out according to the first process of Starting Material Synthesis 1-1.

(Fourth Process)

This process is a process in which the compound (1-d) is obtained by subjecting the compound (8-d) to a Boc-removal reaction. The reaction can be carried out according to the third process of Starting Material Synthesis 1-1.

The compound of the formula (I) is isolated and purified as a free compound, a salt thereof, a hydrate, a solvate, or a crystal polymorphism substance. The salt of the compound of the formula (I) can be prepared by a common salt formation reaction.

Isolation and purification are carried out by applying usual chemical operations such as extraction, fractional crystallization, various types of fractional chromatography, and the like.

Various isomers can be prepared by selecting a suitable starting compound, or can be separated using a difference in physicochemical properties among the isomers. For example, optical isomers are obtained by general optical resolution methods (for example, fractional crystallization leading to a diastereomeric salt with an optically active base or an acid, or chromatography using a chiral column or the like) of a racemic mixture, and can also be prepared from a suitable optically active starting compound.

The pharmacological activity of the compound of the formula (I) was confirmed by the tests shown below.

Test Example 1

Evaluation of Human Mitochondrial Complex I Inhibitory Effect

Mitochondria was extracted from MDA-MB-453 tumor, and the Complex I inhibitory activity of the test compound was evaluated.

Human PIK3CA mutation-positive breast cancer cell line MDA-MB-453 cells were subcutaneously implanted into nude mice, MDA-MB-453 tumor was excised, a mitochondria extraction solution (0.25 M Sucrose, 2 mM EDTA, 10 mM Tris/HCl pH 7.5) of 9 times of tumor weight was added thereto, and crushing was carried out thereon. The reaction mixture was centrifuged at 600×g and 4° C. for 10 minutes to obtain a supernatant, and the supernatant was centrifuged at 14000×g and 4° C. for 10 minutes, thereby obtaining a pellet. The pellet was suspended in 10 mM Tris/HCl pH 7.5 of 5 times of the excised tumor weight, thereby obtaining a human mitochondrial suspension.

Next, 25 μl of the human mitochondrial suspension per 1 ml of Complex I activity measurement solution (200 mM potassium phosphate pH 7.6, 0.35% Bovine Serum Albumin (BSA), 60 μM 2,6-dichlorophenol-indophenol, 70 μM decylubiquinone, 1 μM antimycin) was added. After dispensed into a 96 or 384-well plate, a test compound (from 10000 nM to 0.3 nM) and DMSO which is a solvent for the test compound as a negative control were added such that a final concentration of Rotenone which is a Complex I inhibitor as a positive control becomes 1 μM. Further, NADH was added so as to have a final concentration of 0.2 mM, and a change in absorbance at a wavelength of 600 nm using SpectraMax (manufactured by Molecular Devices LLC) set to 37° C. in advance was measured. Signal values in a DMSO treatment is set to top, signal values in a Rotenone 1 μM treatment was set to bottom, a signal variation within a range in which the reaction is linear was calculated, and 50% inhibition values ($IC_{50}$) were calculated by a logistic regression method. The results of some compounds of the formula (I) are shown in Table 1. Moreover, in the Table, Ex indicates Example No. (the same shall apply hereinafter.).

TABLE 1

| Ex | $IC_{50}$ (nM) |
|---|---|
| 1 | 41 |
| 7 | 75 |
| 8 | 83 |
| 18 | 7.1 |
| 23 | 160 |

TABLE 1-continued

| Ex | IC$_{50}$ (nM) |
|---|---|
| 35 | 1.8 |
| 36 | 55 |
| 37 | 29 |
| 38 | 59 |
| 44 | 87 |
| 49 | 18 |
| 57 | 12 |
| 66 | 120 |
| 69 | 22 |
| 79 | 120 |

Test Example 2

Evaluation of AMPK Activation Effect

By measuring phosphorylation of 79th serine (Ser79) of Acetyl-CoA Carboxylase (ACC) which is a substrate of AMPK with Cell ELISA, the AMPK activation effect by the test compound was evaluated.

In order to make MDA-MB-453 cell become 15000 cells per well, each 36 μl was seeded in Leibovitz's L-15 medium including 10% fetal bovine serum (manufactured by Life Technologies Corp.) in a 384 well plate, followed by culturing at 37° C. overnight in the absence of $CO_2$. The following day, the test compound and DMSO which is a solvent for the test compound as a negative control were diluted with a fresh medium so as to become 10-fold concentration of the final concentration, and the resultant product was added by 4 μl to each well (the test compound had 10 steps in a final concentration from 10000 nM to 0.3 nM, a final concentration of DMSO was 0.1%), followed by culturing at 37° C. for 2 hours in the absence of $CO_2$. After the incubation, 20 μl of a 40% glyoxal solution (Nacalai Tesque) was added to each well, and then cells were fixed by leaving to stand at room temperature for 30 minutes. Thereafter, the supernatant was removed by centrifuging the plate, and then 0.1% Triton X-100-containing Phosphate-Buffered Saline (PBS) was added to each well by 20 followed by incubating at room temperature for 10 minutes. The 0.1% Triton X-100-containing PBS was removed by centrifuging for 8 seconds at 800 rpm (all solution removal operation by centrifuge described below were carried out under the same conditions), and then a blocking solution (ODYSSEY Blocking Buffer; manufactured by Li—COR Biosciences) was added to each well by 20 μl, followed by leaving to stand at room temperature for 1 hour. The blocking solution was removed by centrifuging, with the exception of the blocking solution by centrifugation, and then a blocking solution which was diluted such that the amount of phosphorylation antibody (manufactured by Cell Signaling Technology, Inc) of ACC Ser79 as a primary antibody is 1/500 was added to each well by 10 followed by leaving to stand at 4° C. overnight. The following day, the reaction liquid was removed by centrifuging the plate, and then 0.05% Tween-20-containing Tris-Buffered Saline (TBS) (manufacture by Thermo Scientific Inc.; used in 1× in which 20×TBS Tween-20 was diluted with ion-exchange water) was added to each well by 25 followed by washing each well by centrifugal removal. The washing of each well was repeated for a total of 3 times. After washing, a blocking solution which was diluted such that the amount of IRDye 800CW Goat anti-Rabbit IgG (manufactured by Li—CoR Biosciences) as a secondary antibody is 1/1000 was added to each well by 10 μl, followed by leaving to stand at room temperature for 1 hour. After the secondary antibody reaction, the reaction liquid was removed by centrifuging the plate, and then each well was washed three times with 0.05% Tween-20-containing TBS in the same manner as after the primary antibody reaction. After the washing solution was removed, without change, the plate was air-dried at room temperature for 3 hours or longer and signals were measured by Aerius (manufactured by Li—CoR Biosciences). Signal values in a DMSO treatment was set to bottom, signal values when reaching a plateau was set to top, and 50% activation values (EC$_{50}$) were calculated by the logistic regression method. The results of some compounds of the formula (I) are shown in Table 2.

TABLE 2

| Ex | EC$_{50}$ (nM) |
|---|---|
| 1 | 24 |
| 7 | 8.3 |
| 8 | 13 |
| 14 | 34 |
| 18 | 3.0 |
| 19 | 10 |
| 23 | 19 |
| 35 | 3.6 |
| 36 | 5.1 |
| 37 | 10 |
| 38 | 13 |
| 44 | 5.2 |
| 49 | 6.5 |
| 50 | 14 |
| 57 | 1.8 |
| 58 | 0.86 |
| 66 | 2.8 |
| 69 | 1.8 |
| 79 | 3.3 |

Test Example 3

Evaluation of Scaffold Independent Cell Proliferation Inhibitory Effect with Respect to Human PIK3CA Mutation-Positive Breast Cancer Cell Line MDA-MB-453 Cells The effect on proliferation of cancer cells of the test compound was evaluated.

Measurement (colony method) of the scaffold independent cell proliferation is known as a system in which the anti-cancer effect of the test compound is examined. As a method for measuring cell-non-adhesive proliferation substituting the colony method, there is a method of using a non-adhesive plate as follows.

In order to make human PIK3 CA mutation-positive breast cancer cell line MDA-MB-453 cells become 500 cells per well in a 384 well non-adhesive plate (Lipidure-Coat plate AT-384; manufactured by NOF Corporation), 36 μl/well was seeded in Leibovitz's L-15 medium including 10% fetal bovine serum (manufactured by Life technologies Corp.), followed by culturing at 37° C. overnight in the presence of $CO_2$. The following day, the test compound (the test compound had 11 steps in a final concentration from 10000 nM to 0.1 nM), and DMSO which is a solvent for the test compound as a negative control were diluted with the medium, and 4 μl was added to cells. Thereafter, the cells were cultured for 4 days at 37° C. in the absence of $CO_2$, and a cytometric reagent (CellTiter-Glo Luminescent Cell Viability assay manufactured by Promega Corporation) was added. The resultant product was stirred for 30 minutes, and then measurement was carried out using a luminescence measurement apparatus (ARVO manufactured by Perkin Elmer Inc.). The measured value in medium alone was set to 100% inhibition, the measured value of the negative control was set to 0% inhibition, and an inhibition rate (%) of the test compound was calculated. 50% inhibition concentrations ($IC_{50}$ values) were calculated by the logistic regression method. The results of some compounds of the formula (I) are shown in Table 3.

TABLE 3

| Ex | $IC_{50}$ (nM) |
|---|---|
| 1 | 12 |
| 7 | 12 |
| 8 | 26 |
| 14 | 7.6 |
| 18 | 2.5 |
| 19 | 8.5 |
| 23 | 40 |
| 35 | 5.2 |
| 36 | 11 |
| 37 | 8.9 |
| 38 | 8.1 |
| 44 | 4.2 |
| 49 | 2.8 |
| 50 | 4.0 |
| 57 | 0.65 |
| 58 | 0.55 |
| 66 | 6.2 |
| 69 | 3.2 |
| 79 | 7.8 |

Test Example 4

Evaluation of Anti-Tumor Effect in Human PIK3CA Mutation-Positive Breast Cancer Cell Line MDA-MB-453 Cell in a Cancer-Bearing Mouse $3 \times 10^6$ cells of MDA-MB-453 cells which were suspended with PBS were subcutaneously injected to be planted in the back of a 5 to 6 weeks old male Balb/c nude mouse (provided by Charles River Laboratories, Japan). 10 days after planting, the test compound was administered. The test was carried out on respective five mice of the solvent group and the test compound administered group, and 6% aqueous cyclodextrin solution was administered to the solvent group, and a mixture of 6% aqueous cyclodextrin solution and the test compound (1 or 3 mg/kg) was orally administered to the test compound administered group. Administration was carried out once a day for 15 days, and body weight and tumor size were measured approximately every other day. The following equation was used to calculate the tumor volume.

[Tumor volume (mm³)]=[major axis of tumor (mm)]×[minor axis of tumor (mm)]²×0.5

The tumor volume of the test compound administered group on the test compound administration start date and the tumor volume in the solvent group on the administration end date was set to 100% inhibition and 0% inhibition, respectively, and the inhibition rate (%) of the test compound was calculated. In addition, in a case where the tumor volume of the test compound administered group was lower than the tumor volume on the administration start date, the tumor volume on the test compound administration start date was set to 0% regression (that is, 100% inhibition), and the tumor volume 0 was set to 100% regression, and the regression rate (%) of the test compound was calculated. The results of some compounds of the formula (I) are shown in Table 4.

TABLE 4

| Ex | Dose of test compound | Anti-tumor effect |
|---|---|---|
| 1 | 3 mg/kg | 26% regression |
| 7 | 3 mg/kg | 49% regression |
| 8 | 3 mg/kg | 88% inhibition |
| 36 | 3 mg/kg | 10% regression |
| 66 | 1 mg/kg | 91% regression |
| 69 | 1 mg/kg | 87% regression |
| 79 | 1 mg/kg | 43% regression |

Moreover, as shown in the following Test Examples, human PIK3CA mutation-positive breast cancer cell line MDA-MB-453 cells in which the anti-tumor effect was confirmed in Test Example 4 are human PIK3CA mutation-positive breast cancer cell lines in which MCT4 is not expressed.

Test Example 5

Evaluation of Anti-Tumor Effect in Several Human PIK3CA Mutation-Positive Breast Cancer Cell Line in a Cancer-Bearing Mouse In the same manner as in Test Example 4, the anti-tumor effect in a cancer-bearing mouse of the test compound with respect to BT-474 cells, HCC1954 cells, MDA-MB-361 cells, CAL-51 cells, and OCUB-M cells which are human PIK3CA mutation-positive breast cancer cell lines was evaluated.

As a result, the test compound exhibited the regression effect on the tumor at a dose of 8 mg/kg with respect to BT-474 cells and OCUB-M cells, and did not exhibit the anti-tumor effect of 50% inhibition or higher with respect to other HCC1954 cells, MDA-MB-361 cells, and CAL-51 cells.

Test Example 6

Measurement of MCT4 Expression Level in Several Human PIK3CA Mutation-Positive Breast Cancer Cell Lines Using the following method, MCT4 expression level in tumor of MDA-MB-453 cells (Test Example 4), BT-474 cells, HCC1954 cells, MDA-MB-361 cells, CAL-51 cells, and OCUB-M cells (hereinbefore, Test Example 5) was measured.

The tumor of the solvent administered group was collected from a cancer-bearing mouse to which test compound administration ended in Test Example 4 or Test Example 5, and immediately frozen in liquid nitrogen. A mixture of CelLytic MT (manufactured by Sigma-Aldrich Co. LLC), protease inhibitor cocktail (manufactured by F. Hoffmann-La Roche Ltd.), and phosphatase inhibitor cocktail (manufactured by Sigma-Aldrich Co. LLC) was added to a portion of the collected tumor, and the tumor was homogenized by Tissue Lyser II (manufactured by QIAGEN). The same amount of tumor protein solution was electrophoresed in NuPAGE 4-12% Bis-Tris Gel (manufactured by Life Technologies Corp.), and transferred to a PVDF membrane. After blocking was carried out by PVDF Blocking Reagent for Can Get Signal solution (manufactured by Toyobo Co., Ltd.), the PVDF membrane was reacted with an MCT4 antibody (H90; manufactured by Santa Cruz Biotechnology, Inc.) at 4° C. overnight. After the PVDF membrane was washed, the PVDF membrane was reacted with a horseradish peroxidase-labeled rabbit IgG antibody (manufactured by GE Healthcare) at room temperature for 1 hour. After the PVDF membrane was washed, the MCT4 expression level was measured using an ECL detection kit (manufactured by GE Healthcare).

As a result, under the above-mentioned experimental conditions, it was confirmed that MCT4 was not sufficiently expressed in tumor of MDA-MB-453 cells, BT-474 cells, and OCUB-M cells. In contrast, it was confirmed that MCT4 was sufficiently expressed in tumors of other HCC1954 cells, MDA-MB-361 cells, and CAL-51 cells.

This MCT4 expression correlates well with the anti-tumor effect of the test compound shown in Test Example 4 and Test Example 5. That is, as a result, the test compound exhibited the tumor regression effect with respect to tumor of human PIK3CA mutation-positive breast cancer cell lines in which MCT4 is not expressed, and in contrast, did not exhibit the anti-tumor effect of 50% inhibition or higher with respect to tumor of human PIK3CA mutation-positive breast cancer cell lines in which MCT4 is expressed.

Test Example 7

Evaluation of Scaffold Independent Cell Proliferation Inhibitory Effect of Several Human Breast Cancer Cell Lines which do not have Mutation of PIK3CA and Measurement of MCT4 Expression Level In order to confirm a relationship between the cell proliferation inhibitory effect of the compound of the formula (I) and the MCT4 expression in the cells, a relationship between the cell proliferation inhibitory effect of the test compound and the MCT4 expression was also examined with respect to human breast cancer cell lines which do not have mutation of PIK3CA.

The cell proliferation inhibitory effect of the test compound was evaluated as follows. In order to make HCC1500 cells, ZR-75-30 cells, HCC2218 cells, SK-BR-3 cells, AU565 cells, HCC1569 cells, HCC1806 cells, and CAL-120 cells which are human breast cancer cell lines which do not have mutation of PIK3CA become 1000 cells per well in a 96 well non-adhesive plate (MS-0096S; manufactured by Sumiron Co., Ltd.), 90 μl/well was seeded in RPMI medium including 10% fetal bovine serum (manufactured by Sigma-Aldrich Co. LLC), followed by culturing at 37° C. overnight in the presence of $CO_2$. The following day, the test compound (the test compound had 9 steps in a final concentration from 3000 nM to 0.3 nM), and DMSO which is a solvent for the test compound as a negative control were diluted with the medium, and 10 μl was added to cells. Thereafter, the cells were cultured for 4 days at 37° C. in the absence of $CO_2$, and a cytometric reagent (CellTiter-Glo Luminescent Cell Viability assay manufactured by Promega Corporation) was added. The resultant product was stirred for 30 minutes, and then measurement was carried out using a luminescence measurement apparatus (ARVO manufactured by Perkin Elmer Inc.). The measured value 0 was set to 100% inhibition, the measured value of the negative control was set to 0% inhibition, and the inhibition rate (%) of the test compound was calculated.

MCT4 expression level of each cell line was measured as follows. In order to make the above-described cell lines become 500000 cells per well in a 6 well adhesive plate (manufactured by IWAKI & Co., Ltd.), 2 ml/well was seeded in RPMI medium including 10% fetal bovine serum, followed by culturing at 37° C. overnight in the presence of $CO_2$. The following day, the test compound (final concentration of 100 nM), and DMSO which is a negative subject were added to each well by 2 μl. The test compound and DMSO were added to the medium, and cultured at 37° C. for 2 hours. The medium was removed, and each well was washed with 500 μl of ice-cold PBS once. 500 μl of the ice-cold PBS was added again, and cells were collected with a cell scraper on ice. Each well was washed with 500 μl of the ice-cold PBS once, and combined with the previously collected cell suspension. After the collected cell suspension was centrifuged at 4° C. for 5 minutes at 3000 rpm, the supernatant was removed to prepare a pellet, and a mixture of CelLytic M (manufactured by Sigma-Aldrich Co. LLC), protease inhibitor cocktail (manufactured by Sigma-Aldrich Co. LLC), and phosphatase inhibitor cocktail (manufacture by Thermo Fisher Scientific Inc.) was added to the pellet. After pipetting, the resultant product was left to stand for 30 minutes on ice, and centrifuged at 4° C. for 5 minutes at 12000 rpm. The supernatant was put into another tube to use as a protein solution for SDS-PAGE. The same amount of protein was electrophoresed using 5% to 20% SDS polyacrylamide gel (manufactured by Wako Pure Chemical Industries, Ltd.), and MCT4 expression level was measured in the same method as in Test Example 6.

As a result, under the above-mentioned experimental conditions, when 100 nM of the test compound was added, the cell proliferation inhibitory effect of 80% inhibition or higher was exhibited with respect to HCC1500 cells, ZR-75-30 cells, and HCC2218 cells which are human breast cancer cell lines which do not have mutation of PIK3CA in which MCT4 is not sufficiently expressed, and in contrast, when 100 nM of a certain compound among the test compound was added, the cell proliferation inhibitory effect of 50% inhibition or higher was not exhibited with respect to SK-BR-3 cells, AU565 cells, HCC1569 cells, HCC1806 cells, and CAL-120 cells which are human breast cancer cell lines which do not have mutation of PIK3CA in which MCT4 is sufficiently expressed.

From the result of the above-described tests, it was confirmed that the compound of the formula (I) have Complex I inhibitory effect and the AMPK activation effect. In addition, it was confirmed that the compound of the formula (I) has the cell proliferation inhibitory effect with respect to human PIK3CA mutation-positive breast cancer cell line MDA-MB-453 cells in which MCT4 is not expressed, and exhibits the anti-tumor effect in an MDA-MB-453 cell in a cancer-bearing mouse. Further, it was confirmed that the compound of the formula (I) has the cell proliferation inhibitory effect with respect to not only human PIK3CA mutation-positive breast cancer cell lines in which MCT4 is not expressed but also human breast cancer cell lines which do not have mutation of PIK3CA in which MCT4 is not expressed. Thus, the compound of the formula (I) can be used for treating breast cancer, in particular, breast cancer in which MCT4 is not expressed, and among others, PIK3CA mutation-positive breast cancer in which MCT4 is not expressed.

A pharmaceutical composition which contains one or two or more kinds of the compound of the formula (I) or the salt thereof as an active ingredient can be prepared by methods which are commonly used, using excipients commonly used in the related art, that is, pharmaceutical excipients or pharmaceutical carriers.

Administration may be any form of an oral administration by a tablet, a pill, a capsule, a granule, powder, or a solution, or a parenteral administration by intraarticular, intravenous, or intramuscular injections, a suppository, an eye drop, an eye ointment, a transdermal solution, an ointment, a transdermal patch, a mucosal solution, a transmucosal patch, or an inhalant.

As a solid composition for the oral administration, a tablet, powder, or a granule can be used. In such a solid composition, one or two or more kinds of active ingredients are mixed with at least one of inert excipients. According to commonly used methods in the related art, the composition may contain an inert additive, for example, a lubricant, a disintegrant, a stabilizer, or a solubilizer. The tablet or pill, if necessary, may be coated with a film of sugar or a stomach-soluble or enteric-soluble substance.

A liquid composition for oral administrations contains an emulsion, a solution preparation, a suspension, a syrup or an elixir which is pharmaceutically acceptable, and contains a generally used inert diluent, for example, purified water or ethanol. In addition to the inert diluent, the liquid composition may contain adjuvants such as a solubilizing agent, a wetting agent, and a suspension, a sweetener, a flavor, a fragrance, or a preservative.

The injection for parenteral administration contains a sterile aqueous or non-aqueous solution preparation, a suspension or an emulsion. As the aqueous solvent, for example, distilled water for injection or physiological saline is included. As the non-aqueous solvent, for example, alcohols such as ethanol are included. Such a composition may further include an isotonic agent, a preservative, a wetting agent, an emulsifier, a dispersant, a stabilizer, or a solubilizer. For example, these are sterilized by filtration through a bacteria-catching filter, or mixing of a germicide or irradiation. In addition, these can also be used by preparing a sterile solid composition, and before using, it is possible to dissolve or suspend the composition in sterile water or a sterile solvent for injection.

As an external application, an ointment, a plaster, a cream, a jelly, a poultice, a spray, a lotion, an eye drop, and an eye ointment are included. A generally used ointment base, lotion base, aqueous or non-aqueous solution, suspension, and emulsion are contained.

The transmucosal agent such as the inhalant and a transnasal agent are used in a solid, liquid or semi-solid form, and can be prepared according to methods known in the related art. For example, a known excipient, a pH adjuster, a preservative, a surfactant, a lubricant, a stabilizer, and a thickener may be suitably added. In administration, it is possible to use a device for a suitable inhalation or insufflation. For example, using a known device such as a metered dose inhaler or a nebulizer, administration can be performed as a solution or a suspension, as a compound alone or a powder of a prescribed mixture, or in combination with a carrier which is pharmaceutically acceptable. A dry powder inhaler may be an inhaler for single or multiple administrations, and it is possible to use dry powder or a powder-containing capsule. Alternatively, a suitable propellant, for example, a form of a pressurized aerosol spray using a suitable gas such as chlorofluoroalkane or carbon dioxide may be used.

In a case of normal oral administration, a daily dose is about 0.001 to 100 mg/kg of body weight, preferably 0.1 to 30 mg/kg, more preferably 0.1 to 10 mg/kg, and this dose is administered once or 2 to 4 times in parts per day. In a case of an intravenous administration, a daily dose is suitably about 0.0001 to 10 mg/kg of body weight, and this dose is administered once or several times in parts per day. In addition, as the transmucosal agent, about 0.001 to 100 mg/kg of body weight is administered once or several times in parts per day. The dose is suitably determined according to individual cases in consideration of symptoms, age, and gender.

The dose differs depending on the types of an administration route, a dosage form, an administration site, an excipient, and an additive, and the pharmaceutical composition of the present invention contains one or more kinds of the compound of the formula (I) or the salt thereof in which the active ingredient is 0.01 to 100% by weight, and 0.01 to 50% by weight as a certain embodiment.

The compound of the formula (I) can be used in combination with various agents for treating diseases which is believed that the compound of the formula (I) described above shows effectiveness. In the combined use, co-administration or separate administration in succession may be performed, or administration may be performed at a desired time interval. The co-administration formulation may be a combined drug, and may be separately formulated.

EXAMPLES

Hereinafter, the preparation methods for the compound of the formula (I) will be described in more detail with reference to examples. Moreover, the present invention is not limited to compounds described in the following examples. In addition, each preparation method for starting compounds will be described in Preparation Examples. In addition, the preparation method for the compound of the formula (I) is not limited to the preparation methods in specific examples shown below, and the compound of the formula (I) can also be prepared by using a combination of the preparation methods or a method apparent to those skilled in the art.

In the present specification, in some cases, naming software such as ACD/Name (registered trademark, manufactured by Advanced Chemistry Development, Inc.) is used in naming of compounds.

In addition, for the sake of convenience, a concentration mol/l is expressed by M. For example, a 1 M aqueous sodium hydroxide solution refers to a 1 mol/l aqueous sodium hydroxide solution.

The powder X-ray diffraction is measured using RINT-TTRII (manufactured by RIGAKU Corporation) under the conditions of a tube: Cu anode, a tube current: 300 mA, a tube voltage: 50 kV, a sampling width: 0.020°, a scanning speed: 4°/min, a wavelength: 1.54056 Å, and a measurement diffraction angle (2θ): 2.5° to 40°, and handling of apparatus including a data process was carried out according to the methods and procedures instructed on each device. Moreover, an error range of a diffraction angle)) (2θ(° in the powder X-ray diffraction is about ±0.2°.

Each crystal is characterized by a powder X-ray diffraction pattern, respectively, and in the powder X-ray diffraction, crystal lattice distance or overall pattern is important in identification of the crystal in terms of the nature of the data. Since a diffraction angle and a diffracted intensity may somewhat vary depending on a direction of crystal growth, a particle size, and measurement conditions, it is not necessary to be strictly interpreted.

Preparation Example 1

N-[3-(dimethylamino)propyl]-N'-ethylcarbodiimide hydrochloride (1.2 g) was added to a mixture of 5-bromo-1H-benzimidazol-2-carboxylic acid (1.0 g), 1-[4-(trifluoromethyl)benzyl]piperazine (1.0 g), 1H-benzotriazol-1-ol (840 mg), and N,N-dimethylformamide (10 ml: hereinafter, abbreviated as DMF), followed by stirring at room temperature overnight. A saturated aqueous sodium hydrogen carbonate solution was added to the reaction mixture, followed by stirring at room temperature for 1 hour, and the resulting solid was collected by filtration, followed by drying under reduced pressure. The obtained solid was dissolved in a mixture of chloroform (100 ml) and ethanol (1 ml) while heating to reflux. The mixture was cooled to room temperature and then hexane (100 ml) was added thereto. The resulting solid was collected by filtration, followed by drying under reduced pressure, thereby obtaining (5-bromo-1H-benzimidazol-2-yl){4-[4-(trifluoromethyl)benzyl]piperazin-1-yl}methanone (1.4 g) as a solid.

Preparation Example 2

A mixture of 2-chloroquinoline-6-carboxylic acid (500 mg), thionyl chloride (5 ml), and DMF (1 drop) was heated to reflux for 30 minutes, and cooled to room temperature. 1-[4-(trifluoromethyl)benzyl]piperazine (620 mg) and triethylamine (340 µl was added to a mixture of the solid obtained by concentrating the reaction mixture under reduced pressure and dichloromethane under ice-cooling, followed by stirring at room temperature for 2 hours. A saturated aqueous sodium hydrogen carbonate solution was added to the reaction mixture, and extraction was carried out using chloroform. The organic layer was washed with a saturated aqueous sodium chloride solution, and dried over anhydrous sodium sulfate. The desiccant was removed, and then the solvent was evaporated under reduced pressure. The obtained residue was purified by amino silica gel column chromatography (hexane-ethyl acetate), thereby obtaining (2-chloroquinolin-6-yl){4-[4-(trifluoromethyl)benzyl]piperazin-1-yl}methanone (630 mg) as an oily material.

Preparation Example 3

Water (2.5 ml) and 1-[4-(trifluoromethyl)benzyl]piperazine (850 mg) were added to a mixture of 6-bromo-2-(trichloromethyl)-1H-imidazo[4,5-b]pyridine (500 mg), sodium hydrogen carbonate (2.0 g), and tetrahydrofuran (5 ml: hereinafter, abbreviated as THF), followed by stirring at room temperature for 20 minutes. Water was added to the reaction mixture, and extraction was carried out using chloroform. The organic layer was washed with a saturated aqueous sodium chloride solution, and dried over anhydrous sodium sulfate. The desiccant was removed, and then the solvent was evaporated under reduced pressure. A mixture of the obtained residue, THF (15 ml), and 1 M hydrochloric acid (15 ml) was stirred at room temperature for 2 hours. A saturated aqueous sodium hydrogen carbonate solution was added to the reaction mixture, and extraction was carried out using chloroform. After the organic layer was dried over anhydrous sodium sulfate, the desiccant was removed, and the solvent was evaporated under reduced pressure. The obtained residue was purified by silica gel chromatography (chloroform-methanol). A mixture of the obtained solid and chloroform (25 ml) was heated to reflux for 30 minutes, and then hexane (50 ml) was added thereto, followed by ice-cooling. The resulting solid was collected by filtration, followed by drying under reduced pressure, thereby obtaining (6-bromo-1H-imidazo[4,5-b]pyridin-2-yl){4-[4-(trifluoromethyl)benzyl]piperazin-1-yl}methanone (490 mg) as a solid.

Preparation Example 4

2-(7-aza-1H-benzotriazol-1-yl)-1,1,3,3-tetramethyluronium hexafluorophosphate (270 mg) was added to a mixture of 5-[1-(tert-butoxycarbonyl)piperidin-4-yl]-1-methyl-1H-indole-2-carboxylic acid (170 mg), N,N-diisopropylethylamine (240 µl), 1-[4-(trifluoromethyl)benzyl]perazine (140 mg), and DMF (2 ml), followed by stirring at room temperature overnight. A saturated aqueous sodium hydrogen carbonate solution and water were added to the reaction mixture, followed by stirring for 1 hour under ice-cooling. The resulting solid was collected by filtration, followed by drying under reduced pressure, thereby obtaining tert-butyl 4-[1-methyl-2-({4-[4-(trifluoromethyl)benzyl]piperazin-1-yl}carbonyl)-1H-indol-5-yl]piperidine-1-carboxylate (280 mg) as a solid.

Preparation Example 5

A 1 M aqueous sodium hydroxide solution (3.2 ml) was added to a solution of methyl 5-bromo-1-methyl-1H-benzimidazol-2-carboxylate (710 mg) in THF (15 ml), followed by stirring at room temperature overnight. 2-(7-aza-1H-benzotriazol-1-yl)-1,1,3,3-tetramethyluronium hexafluorophosphate (1.5 g) was added to a mixture of the residue obtained by concentrating the reaction mixture under reduced pressure, 1-[4-(trifluoromethyl)benzyl]piperazine (960 mg), and DMF (14 ml), followed by stirring at room temperature overnight. A saturated aqueous sodium hydrogen carbonate solution was added to the reaction mixture under ice-cooling, and extraction was carried out using ethyl acetate. The organic layer was washed with water and a saturated aqueous sodium chloride solution in this order, and dried over anhydrous sodium sulfate. The desiccant was removed, and then the solvent was evaporated under reduced pressure. The obtained residue was purified by silica gel column chromatography (hexane-ethyl acetate), thereby obtaining (5-bromo-1-methyl-1H-benzimidazol-2-yl){4-[4-(trifluoromethyl)benzyl]piperazin-1-yl}-methanone (580 mg) as an amorphous material.

Preparation Example 6

After 1-[4-(trifluoromethyl)benzyl]piperazine (3.7 g) was added to a mixture of 6-bromo-1-methyl-2-(trichloromethyl)-1H-benzimidazole (2.2 g), sodium hydrogen carbonate (8.6 g), THF (22 ml), and water (11 ml), the resultant product was stirred at room temperature for 30 minutes, and heated to reflux for 4 hours. After dioxane (11 ml) was added to the reaction mixture, the resultant product was heated to reflux for 76 hours, and cooled to room temperature. After concentrating under reduced pressure, extraction was carried out on the obtained mixture using ethyl acetate. The organic layer was washed with a saturated aqueous sodium chloride solution, and dried over anhydrous sodium sulfate. The desiccant was removed, and then the solvent was evaporated under reduced pressure. The obtained residue was purified by silica gel column chromatography (hexane-ethyl acetate), thereby obtaining (6-bromo-1-methyl-1H-benzimidazol-2-yl){4-[4-(trifluoromethyl)benzyl]piperazin-1-yl}-methanone (1.7 g) as a solid.

Preparation Example 7

Ethyl 1H-indazole-5-carboxylate (500 mg) was added to a mixture of 0.5 M potassium hexamethyldisilazide/toluene solution (5.3 ml), 18-crown-6 (100 mg), and THF (15 ml) at room temperature, followed by stirring at room temperature for 5 minutes. After tert-butyl 4-[(methanesulfonyl)oxy]piperidine-1-carboxylate (740 mg) was added to the reaction mixture, the reaction mixture was stirred at 90° C. for 17 hours, and cooled to room temperature. Water was added to the reaction mixture, and extraction was carried out using ethyl acetate. The organic layer was washed with a saturated aqueous sodium chloride solution, and dried over anhydrous magnesium sulfate. The desiccant was removed, and then the solvent was evaporated under reduced pressure. The obtained residue was purified by amino silica gel column chromatography (hexane-ethyl acetate), thereby obtaining ethyl 1-[1-(tert-butoxycarbonyl)piperidin-4-yl]-1H-indazole-5-carboxylate (Preparation Example 7-1: 270 mg) as a candy shape material and ethyl 2-[1-(tert-butoxycarbonyl)piperidin-4-yl]-2H-indazole-5-carboxylate (Preparation Example 7-2: 410 mg) as a solid, respectively.

Preparation Example 8

After a solution of 1-(chloromethyl)-4-(difluoromethyl)benzene (4.4 g) in toluene (5 ml) was added to a mixture of piperazine (15 g) and toluene (40 ml) at 85° C., the reaction mixture was stirred at 85° C. for 3 hours, and then cooled to room temperature. A saturated aqueous sodium hydrogen carbonate solution was added to the reaction mixture, and extraction was carried out using diethyl ether. The organic layer was washed with water and a saturated aqueous sodium chloride solution in this order, and dried over anhydrous sodium sulfate. The desiccant was removed, and then the solvent was evaporated under reduced pressure, thereby obtaining 1-[4-(difluoromethyl)benzyl]piperazine (5.0 g) as an oily material.

Preparation Example 9

A mixture of (5-bromo-1H-benzimidazol-2-yl){4-[4-(trifluoromethyl)benzyl]piperazin-1-yl}methanone (1.2 g), tert-butyl 4-(4,4,5,5-tetramethyl-1,3,2-dioxaborolan-2-yl)-3,6-dihydropyridine-1(2H)-carboxylate (1.6 g), tetrakis(triphenylphosphine)palladium (590 mg), sodium carbonate (2.2 g), dioxane (40 ml), and water (10 ml) was stirred at 95° C. for 24 hours in an argon atmosphere, and then cooled to room temperature. Water was added to the reaction mixture, and extraction was carried out using ethyl acetate. After the organic layer was dried over anhydrous sodium sulfate, the desiccant was removed, and the solvent was evaporated under reduced pressure. The obtained residue was purified by silica gel column chromatography (chloroform-methanol), thereby obtaining tert-butyl 4-[2-({4-[4-(trifluoromethyl)benzyl]piperazin-1-yl}carbonyl)-1H-benzimidazol-5-yl]-3,6-dihydropyridine-1(2H)-carboxylate (1.2 g) as an oily material.

Preparation Example 10

A mixture of tert-butyl 4-ethynylpiperidine-1-carboxylate (1.5 g), methyl 4-amino-3-iodobenzoate (2.2 g), copper (I) iodide (82 mg), dichlorobis(triphenylphosphine)palladium (500 mg), and triethylamine (45 ml) was stirred at room temperature overnight. The solvent was evaporated under reduced pressure, and the obtained residue was purified by silica gel column chromatography (hexane-ethyl acetate) and a silica gel column chromatography (chloroform-methanol), thereby obtaining tert-butyl 4-{[2-amino-5-(methoxycarbonyl)phenyl]ethynyl}piperidine-1-carboxylate (1.8 g) as an oily material.

Preparation Example 11

After a 1.0 M lithium hex amethyldisilazide/THF solution (2.2 ml) was added to a mixture of (5-bromo-1H-benzimidazol-2-yl){4-[4-(trifluoromethyl)benzyl]piperazin-1-yl}methanone (300 mg), tert-butyl piperazine-1-carboxylate (140 mg), dicyclohexyl(2',6'-diisopropoxybiphenyl-2-yl)phosphine (15 mg) and chloro(2-dicyclohexylphosphino-2',6'-diisopropoxy-1,1'-biphenyl)[2-(2-aminoethyl)phenyl]palladium tert-butyl methyl ether adduct (23 mg) in an argon atmosphere, the reaction mixture was stirred at 65° C. for 17 hours, and cooled to room temperature. Water and a saturated aqueous ammonium chloride solution were added to the reaction mixture, and extraction was carried out using chloroform. The organic layer was washed with a saturated aqueous sodium chloride solution, and dried over anhydrous sodium sulfate. The desiccant was removed, and then the solvent was evaporated under reduced pressure. The obtained residue was purified by silica gel column chromatography (chloroform-methanol) and a silica gel column chromatography (hexane-ethyl acetate), thereby obtaining tert-butyl 4-[2-({4-[4-(trifluoromethyl)benzyl]piperazin-1-yl}carbonyl)-1H-benzimidazol-5-yl]piperazine-1-carboxylate (250 mg) as a solid.

Preparation Example 12

A mixture of (5-chloro-1H-pyrrolo[2,3-c]pyridin-2-yl){4-[4-(trifluoromethyl)benzyl]piperazin-1-yl}methanone (300 mg), tert-butyl 4-(4,4,5,5-tetramethyl-1,3,2-dioxaborolan-2-yl)-3,6-dihydropyridine-1(2H)-carboxylate (440 mg), dichlorobis[di-tert-butyl(4-dimethylaminophenyl)phosphine]palladium (150 mg), potassium carbonate (780 mg), dioxane (12 ml), and water (3 ml) was stirred at 95° C. overnight, and then cooled to room temperature. Water was added to the reaction mixture, and extraction was carried out using chloroform. After the organic layer was dried over anhydrous sodium sulfate, the desiccant was removed, and the solvent was evaporated under reduced pressure. The obtained residue was purified by silica gel column chromatography (hexane-ethyl acetate) and a DIOL silica gel column chromatography (hexane-ethyl acetate), thereby obtaining tert-butyl 4-[2-({4-[4-(trifluoromethyl)benzyl]piperazin-1-yl}carbonyl)-1H-pyrrolo[2,3-c]pyridin-5-yl]-3,6-dihydropyridine-1(2H)-carboxylate (300 mg) as an amorphous material.

Preparation Example 13

10% palladium-activated charcoal (about 50% water-containing product, 500 mg) was added to a solution of tert-butyl 4-[2-({4-[4-(trifluoromethyl)benzyl]piperazin-1-yl}carbonyl)-1H-benzimidazol-5-yl]-3,6-dihydropyridine-1(2H)-carboxylate (1.4 g) in ethanol (40 ml), followed by stirring at room temperature for 6 hours in a hydrogen atmosphere. The insoluble material was removed, and then the solvent was evaporated under reduced pressure. 10% palladium-activated charcoal (about 50% water-containing product, 500 mg) was added to a solution of the obtained residue in ethanol (40 ml), followed by stirring at room temperature for 4 hours in a hydrogen atmosphere of 3.0 kgf/cm$^2$. The insoluble material was removed, and then the solvent was evaporated under reduced pressure. 20% palladium hydroxide-activated charcoal (about 50% water-containing product, 800 mg) was added to a solution of the obtained residue in methanol (41 ml), followed by stirring at room temperature for 24 hours in a hydrogen atmosphere of 3.0 kgf/cm$^2$. The insoluble material was removed, and then the solvent was evaporated under reduced pressure. The obtained residue was purified by silica gel column chromatography (chloroform-methanol), thereby obtaining tert-butyl 4-[2-({4-[4-(trifluoromethyl)benzyl]piperazin-1-yl}carbonyl)-1H-benzimidazol-5-yl]piperidine-1-carboxylate (1.1 g) as an oily material.

Preparation Example 14

20% palladium hydroxide-activated charcoal (about 50% water-containing product, 260 mg) was added to a solution of tert-butyl 4-(2-{[4-(4-cyanobenzyl)piperazin-1-yl]carbonyl}-1H-benzimidazol-6-yl)-3,6-dihydropyridine-1(2H)-carboxylate (380 mg) in ethanol (12 ml), followed by stirring at room temperature overnight in a hydrogen atmosphere of 3.0 kgf/cm$^2$. The insoluble material was removed, and then the solvent was evaporated under reduced pressure. 20% palladium hydroxide-activated charcoal (about 50% water-containing product, 290 mg) was added to a solution of the obtained residue in ethanol (12 ml), followed by stirring at room temperature overnight in a hydrogen atmosphere of 3.0 kgf/cm$^2$. The insoluble material was removed, and then the solvent was evaporated under reduced pressure. The obtained residue was purified by amino silica gel column chromatography (chloroform-methanol), thereby obtaining tert-butyl 4-[2-(piperazin-1-yl-carbonyl)-1H-benzimidazol-6-yl]piperidine-1-carboxylate (250 mg) as a solid.

Preparation Example 15

10% palladium-activated charcoal (about 50% water-containing product, 1.0 g) was added to a mixture of tert-butyl 4-[2-({4-[4-(trifluoromethyl)benzyl]piperazin-1-yl}carbonyl)-1H-indol-6-yl]-3,6-dihydropyridine-1(2H)-carboxylate (2.2 g), THF (60 ml), ethanol (20 ml), and methanol (10 ml), followed by stirring at room temperature for 48 hours in a hydrogen atmosphere. The insoluble material was removed, and then the solvent was evaporated under reduced pressure. The obtained residue was purified by silica gel column chromatography (chloroform-methanol), thereby obtaining tert-butyl 4-[2-({4-[4-(trifluoromethyl)benzyl]piperazin-1-yl}carbonyl)-1H-indol-6-yl]piperidine-1-carboxylate (530 mg) as an amorphous material.

Preparation Example 16

20% palladium hydroxide-activated charcoal (about 50% water-containing product, 82 mg) was added to a mixture of benzyl 4-({5-[1-(tert-butoxycarbonyl)-1,2,3,6-tetrahydropyridin-4-yl]-1,3-benzothiazol-2-yl}carbonyl)piperazine-1-carboxylate (330 mg), THF (12 ml), and ethanol (4 ml), followed by stirring at room temperature for 3 hours in a hydrogen atmosphere. The insoluble material was removed, and then the solvent was evaporated under reduced pressure. The obtained residue was purified by amino silica gel column chromatography (chloroform-methanol), thereby obtaining a fraction including tert-butyl 4-[2-(piperazin-1-yl-carbonyl)-1,3-benzothiazol-5-yl]piperidine-1-carboxylate and a fraction including the starting material, respectively. 20% palladium hydroxide-activated charcoal (about 50% water-containing product, 410 mg) was added to a mixture of the residue obtained by concentrating the fraction including the starting material under reduced pressure, THF (5 ml), and ethanol (5 ml), followed by stirring at room temperature for 2.5 hours in a hydrogen atmosphere. The insoluble material was removed, and then the solvent was evaporated under reduced pressure. The obtained residue was purified by amino silica gel column chromatography (chloroform-methanol), thereby obtaining a fraction including tert-butyl 4-[2-(piperazin-1-yl-carbonyl)-1,3-benzothiazol-5-yl]piperidine-1-carboxylate and a fraction including the starting material, respectively. 20% palladium hydroxide-activated charcoal (about 50% water-containing product, 820 mg) was added to a mixture of the residue obtained by concentrating the fraction including the starting material under reduced pressure, THF (5 ml), and ethanol (5 ml), followed by stirring at room temperature for 1.5 hours in a hydrogen atmosphere. The insoluble material was removed, and then the solvent was evaporated under reduced pressure. The obtained residue was purified by amino silica gel column chromatography (chloroform-methanol), followed by combining with the fraction obtained above. The mixture was concentrated under reduced pressure, thereby obtaining tert-butyl 4-[2-(piperazin-1-yl-carbonyl)-1,3-benzothiazol-5-yl]piperidine-1-carboxylate (50 mg) as an oily material.

Preparation Example 17

20% palladium hydroxide-activated charcoal (about 50% water-containing product, 110 mg) was added to a mixture of tert-butyl 4-[2-({4-[4-(trifluoromethyl)benzyl]piperazin-1-yl}carbonyl)-1H-imidazo[4,5-b]pyridin-6-yl]-3,6-dihydropyridine-1(2H)-carboxylate (110 mg), THF (4.5 ml), and methanol (2.3 ml), followed by stirring at room temperature for 30 minutes in a hydrogen atmosphere of 3.0 kgf/cm$^2$. 20% palladium hydroxide-activated charcoal (about 50% water-containing product, 110 mg) was added to a mixture of the residue obtained by evaporating the solvent under reduced pressure after the insoluble material was removed, THF (4.5 ml), and methanol (2.3 ml), followed by stirring at room temperature for 3 hours in a hydrogen atmosphere of 3.0 kgf/cm$^2$. 20% palladium hydroxide-activated charcoal (about 50% water-containing product, 110 mg) was added to a mixture of the residue obtained by evaporating the solvent under reduced pressure after the insoluble material was removed, THF (4.5 ml), and methanol (2.3 ml), followed by stirring at room temperature for 3 hours in a hydrogen atmosphere of 3.0 kgf/cm$^2$. The insoluble material was removed, and then the solvent was evaporated under reduced pressure, thereby obtaining tert-butyl 4-[2-({4-[4-(trifluoromethyl)benzyl]piperazin-1-yl}carbonyl)-3H-imidazo[4,5-b]pyridin-6-yl]piperidine-1-carboxylate (76 mg) as an oily material.

Preparation Example 18

20% palladium hydroxide-activated charcoal (about 50% water-containing product, 69 mg) was added to a mixture of methyl 5-[1-(tert-butoxycarbonyl)-1,2,3,6-tetrahydropyridin-4-yl]-3-methyl-1H-indole-2-carboxylate (690 mg), ethanol (10 ml), and THF (10 ml), followed by stirring at room temperature for 1 hour in a hydrogen atmosphere of 4.0 kgf/cm$^2$. The insoluble material was removed, and then the solvent was evaporated under reduced pressure. After 20% palladium hydroxide-activated charcoal (about 50% water-containing product, 140 mg) was added to a mixture of the obtained residue, ethanol (10 ml), and THF (10 ml), the reaction mixture was stirred at room temperature for 1 hour in a hydrogen atmosphere of 4.0 kgf/cm$^2$, and stirred at 50° C. for 1.5 hours. After the reaction mixture was cooled to room temperature, the insoluble material was removed, and then the solvent was evaporated under reduced pressure. After diethyl ether was added to the obtained residue, the resulting solid was collected by filtration, followed by drying under reduced pressure. 20% palladium hydroxide-activated charcoal (about 50% water-containing product, 32 mg) was added to a mixture of the obtained solid, ethanol (5 ml), and THF (5 ml), followed by stirring at room temperature for 1.5 hours in a hydrogen atmosphere of 4.0 kgf/cm². The insoluble material was removed, and then the solvent was evaporated under reduced pressure, thereby obtaining methyl 5-[1-(tert-butoxycarbonyl)piperidin-4-yl]-3-methyl-1H-indole-2-carboxylate (310 mg) as a solid.

Preparation Example 19

After 20% palladium hydroxide-activated charcoal (about 50% water-containing product, 360 mg) was added to a mixture of tert-butyl 4-[4-fluoro-2-({4-[4-(trifluoromethyl)benzyl]piperazin-1-yl}carbonyl)-1H-benzimidazol-6-yl]-3,6-dihydropyridine-1(2H)-carboxylate (720 mg), THF (10 ml), and methanol (10 ml), the reaction mixture was stirred at 55° C. for 2 hours in a hydrogen atmosphere of 4.0 kgf/cm², and cooled to room temperature. The insoluble material was removed, and then the solvent was evaporated under reduced pressure. The obtained residue was purified by silica gel column chromatography (chloroform-methanol), thereby obtaining tert-butyl 4-[4-fluoro-2-({4-[4-(trifluoromethyl)benzyl]piperazin-1-yl}carbonyl)-1H-benzimidazol-6-yl]piperidine-1-carboxylate (460 mg) as a solid.

Preparation Example 20

After a 4 M hydrogen chloride/ethyl acetate solution (5 ml) was added to a solution of tert-butyl 4-[2-({4-[4-(trifluoromethyl)benzyl]piperazin-1-yl}carbonyl)-1H-benzimidazol-5-yl]piperidine-1-carboxylate (1.1 g) in ethyl acetate (30 ml), the reaction mixture was stirred at room temperature for 6 hours, and then left to stand overnight. The solvent was evaporated under reduced pressure, and then ethyl acetate and hexane was added to the obtained residue. The resulting solid was collected by filtration, followed by drying under reduced pressure, thereby obtaining hydrochloride (740 mg: a molar ratio to hydrogen chloride was not determined) of [5-(piperidin-4-yl)-1H-benzimidazol-2-yl]{4-[4-(trifluoromethyl)benzyl]piperazin-1-yl}methanone as a solid.

Preparation Example 21

Trifluoroacetic acid (5 ml) was added to a solution of tert-butyl 4-[5-({4-[4-(trifluoromethyl)benzyl]piperazin-1-yl}carbonyl)-1H-indol-1-yl]piperidine-1-carboxylate (1.4 g) in dichloromethane (10 ml) at room temperature, followed by leaving to stand overnight. After the solvent was evaporated under reduced pressure, a saturated aqueous sodium hydrogen carbonate solution was added to the obtained residue, and then extraction was carried out using chloroform. After the organic layer was dried over anhydrous sodium sulfate, the desiccant was removed, and the solvent was evaporated under reduced pressure. The obtained residue was purified by amino silica gel column chromatography (chloroform-methanol), thereby obtaining [1-(piperidin-4-yl)-1H-indol-5-yl]{4-[4-(trifluoromethyl)benzyl]piperazin-1-yl}methanone (1.2 g) as an oily material.

Preparation Example 22

After a 4 M hydrogen chloride/dioxane solution (3.6 ml) was added to a solution of tert-butyl 4-[6-({4-[4-(trifluoromethyl)benzyl]piperazin-1-yl}carbonyl)quinolin-2-yl]piperazine-1-carboxylate (840 mg) in dioxane (4 ml), the reaction mixture was stirred at room temperature for 2 hours, and then left to stand overnight. After the solvent was evaporated under reduced pressure, a saturated aqueous sodium hydrogen carbonate solution was added to the obtained residue, and then extraction was carried out using chloroform. After the organic layer was dried over anhydrous sodium sulfate, the desiccant was removed, and the solvent was evaporated under reduced pressure. The obtained residue was purified by amino silica gel column chromatography (chloroform-methanol), thereby obtaining [2-(piperazin-1-yl)quinolin-6-yl]{4-[4-(trifluoromethyl)benzyl]piperazin-1-yl}methanone (540 mg) as an oily material.

Preparation Example 23

A 4 M hydrogen chloride/ethyl acetate solution (12 ml) was added to a mixture of tert-butyl 4-[(2,2-difluoro-1,3-benzodioxol-5-yl)methyl]piperazine-1-carboxylate (3.3 g) and ethyl acetate (12 ml), followed by stirring at room temperature for 2 hours. The resulting solid was collected by filtration, followed by drying under reduced pressure. A 4 M hydrogen chloride/ethyl acetate solution (10 ml) was added to a mixture of the obtained solid, methanol (12 ml), and ethyl acetate (12 ml), followed by stirring at room temperature for 4 hours. After diethyl ether was added to the reaction mixture, the solid was collected by filtration, and then dried under reduced pressure, thereby obtaining hydrochloride (2.8 g: a molar ratio to hydrogen chloride was not determined) of 1-[(2,2-difluoro-1,3-benzodioxol-5-yl)methyl]piperazine as a solid.

Preparation Example 24

A mixture of methyl 1H-indole-5-carboxylate (700 mg), tert-butyl 4-hydroxypiperidine-1-carboxylate (1.5 g), cyanomethylenetributylphosphorane (3.7 ml), and toluene (14 ml) was heated to reflux for 14 hours, and then cooled to room temperature. After cyanomethylenetributylphosphorane (1.9 ml) was added to the reaction mixture, the reaction mixture was heated to reflux for 14 hours, and cooled to room temperature. The solvent was evaporated under reduced pressure, and the obtained residue was purified by silica gel column chromatography (chloroform-methanol) and a silica gel column chromatography (hexane-ethyl acetate), thereby obtaining methyl 1-[1-(tert-butoxycarbonyl)piperidin-4-yl]-1H-indole-5-carboxylate (1.1 g) as an oily material.

Preparation Example 25

A 1 M aqueous sodium hydroxide solution (2 ml) was added to a mixture of methyl 1-[1-(tert-butoxycarbonyl)piperidin-4-yl]-1H-indole-5-carboxylate (1.1 g), methanol (10 ml), and THF (10 ml), followed by stirring at room temperature for 2 hours. A 1 M aqueous sodium hydroxide solution (8 ml) was added to the reaction mixture, followed by stirring at 50° C. for 3 hours. After the solvent was evaporated under reduced pressure, 1 M hydrochloric acid was added to the obtained residue to adjust pH to be pH 4.0 to 4.5 at room temperature, and then water was added thereto. The resulting solid was collected by filtration, and then dried under reduced pressure, thereby obtaining 1-[1-(tert-butoxycarbonyl)piperidin-4-yl]-1H-indole-5-carboxylic acid (850 mg) as a solid.

Preparation Example 26

A mixture of ethyl 2-chloro-1H-benzimidazole-5-carboxylate (490 mg), tert-butyl piperazine-1-carboxylate (1.0 g), N,N-diisopropylethylamine (940 μl), and N-methylpyrrolidone (2 ml) was reacted at 170° C. for 30 minutes in a sealed tube using a microwave reaction apparatus (manufactured by Biotage), followed by cooling to room temperature. Water was added to the reaction mixture, and extraction was carried out using ethyl acetate. The organic layer was washed with water and a saturated aqueous sodium chloride solution in this order, and dried over anhydrous sodium sulfate. The desiccant was removed, and then the solvent was evaporated under reduced pressure. A mixture of the obtained residue and ethyl acetate (10 ml) was dissolved while being heated to reflux. After hexane (70 ml) was added to the mixture, the reaction mixture was cooled to room temperature, and then stirred at room temperature for 1 hour. The resulting solid was collected by filtration, and then dried under reduced pressure, thereby obtaining ethyl 2-[4-(tert-butoxycarbonyl)piperazin-1-yl]-1H-benzimidazole-5-carboxylate (730 mg) as a solid.

Preparation Example 27

A mixture of (2-chloroquinolin-6-yl){4-[4-(trifluoromethyl)benzyl]piperazin-1-yl}methanone (640 mg), tert-butyl piperazine-1-carboxylate (820 mg), potassium carbonate (610 mg), acetonitrile (3.2 ml), and DMF (6.4 ml) was stirred at room temperature overnight, followed by stirring at 95° C. for 6 hours. tert-Butyl piperazine-1-carboxylate (270 mg) and potassium carbonate (200 mg) were added to the reaction mixture, followed by stirring at 95° C. for 8 hours. After the reaction mixture was cooled to room temperature, water (200 ml) was added thereto. The resulting solid was collected by filtration, and then dried under reduced pressure. The obtained solid was purified by silica gel column chromatography (chloroform-methanol), thereby obtaining tert-butyl 4-[6-({4-[4-(trifluoromethyl)benzyl]piperazin-1-yl}carbonyl)quinolin-2-yl]-piperazine-1-carboxylate (840 mg) as an oily material.

Preparation Example 28

Sodium hydride (containing a liquid paraffin of about 45%, 89 mg) was added to a solution of tert-butyl 4-[5-({4-[4-(trifluoromethyl)benzyl]piperazin-1-yl}carbonyl)-1H-indol-2-yl]piperidine-1-carboxylate (510 mg) in DMF (5.1 ml) under ice-cooling, followed by stirring at room temperature for 30 minutes. Methyl iodide (61 μl) was added to the reaction mixture under ice-cooling, followed by stirring at room temperature for 2 hours. Water was added to the reaction mixture, followed by stirring at room temperature for 30 minutes. The resulting solid was collected by filtration, and then dried under reduced pressure. The obtained solid was purified by silica gel column chromatography (chloroform-methanol), thereby obtaining a mixture of the starting material and a main reaction product. Sodium hydride (containing a liquid paraffin of about 45%, 90 mg) was added to a solution of the obtained mixture in DMF (5 ml) under ice-cooling, followed by stirring at room temperature for 30 minutes. Methyl iodide (61 μl) was added to the reaction mixture under ice-cooling, followed by stirring at room temperature overnight. Water was added to the reaction mixture, followed by stirring at room temperature for 30 minutes. The resulting solid was collected by filtration, and then dried under reduced pressure. The obtained solid was purified by silica gel column chromatography (chloroform-methanol), thereby obtaining tert-butyl 4-[1-methyl-5-({4-[4-(trifluoromethyl)benzyl]piperazin-1-yl}carbonyl)-1H-indol-2-yl]-piperidine-1-carboxylate (160 mg) as a solid.

Preparation Example 29

After dimethyl sulfate (32 μl) was added to a mixture of methyl 5-[1-(tert-butoxycarbonyl)piperidin-4-yl]-3-methyl-1H-indole-2-carboxylate (82 mg), cesium carbonate (130 mg), and acetonitrile (2 ml), and the reaction mixture was stirred at 75° C. overnight, and then cooled to room temperature. After water was added to the reaction mixture, extraction was carried out using ethyl acetate. The organic layer was washed with a saturated aqueous sodium chloride solution, and dried over anhydrous sodium sulfate. The desiccant was removed, and then the solvent was evaporated under reduced pressure. The obtained residue was purified by silica gel column chromatography (hexane-ethyl acetate), thereby obtaining methyl 5-[1-(tert-butoxycarbonyl)piperidin-4-yl]-1,3-dimethyl-1H-indole-2-carboxylate (78 mg) as a solid.

Preparation Example 30

Under a nitrogen gas flow, sodium hydride (containing a liquid paraffin of about 45%, 20 mg) was added to a solution of tert-butyl 4-[2-({4-[4-(trifluoromethyl)benzyl]piperazin-1-yl}carbonyl)-1H-indol-6-yl]-piperidin-1-carboxylate (250 mg) in N-methylpyrrolidone (5 ml) under ice-cooling, followed by stirring at room temperature for 30 minutes. Methyl iodide (30 μl) was added to the reaction mixture at room temperature, followed by stirring at room temperature for 2.5 hours. Water was added to the reaction mixture, and extraction was carried out using ethyl acetate. The organic layer was washed with water and a saturated aqueous sodium chloride solution in this order, and dried over anhydrous magnesium sulfate. The desiccant was removed, and then the solvent was evaporated under reduced pressure. After the obtained residue was purified by silica gel column chromatography (hexane-ethyl acetate), the obtained oily material was dissolved in ethyl acetate, and then washed with water and a saturated sodium chloride solution in this order. After the organic layer was dried over anhydrous magnesium sulfate, the desiccant was removed, and then the solvent was evaporated under reduced pressure, thereby obtaining tert-butyl 4-[1-methyl-2-({4-[4-(trifluoromethyl)benzyl]piperazin-1-yl}carbonyl)-1H-indol-6-yl]-piperidine-1-carboxylate (180 mg) as an amorphous material.

Preparation Example 31

A mixture of tert-butyl piperazine-1-carboxylate (3.0 g), 2-fluoro-4-(trifluoromethyl)benzaldehyde (2.6 ml), acetic acid (1.8 ml), and dichloromethane (60 ml) was stirred at room temperature for 1 hour. Sodium triacetoxyborohydride (6.8 g) was added to the reaction mixture, followed by stirring at room temperature overnight. After a saturated aqueous sodium hydrogen carbonate solution was added to the reaction mixture, the reaction mixture was stirred at room temperature for 15 minutes, and chloroform and water were added thereto. After liquid-liquid partition, the organic layer was washed with a saturated aqueous sodium chloride solution, and dried over anhydrous sodium sulfate. The desiccant was removed, and then the solvent was evaporated under reduced pressure. The obtained residue was purified by silica gel column chromatography (chloroform-methanol), thereby obtaining tert-butyl 4-[2-fluoro-4-(trifluoromethyl)benzyl]piperazine-1-carboxylate (5.0 g) as an oily material.

Preparation Example 32

Sodium triacetoxyborohydride (3.0 g) was added to a mixture of tert-butyl (2S)-2-methylpiperazine-1-carboxylate (1.0 g), 4-(trifluoromethyl)benzaldehyde (7004 acetic acid (50 µl), and dichloromethane (20 ml), followed by stirring at room temperature for 64 hours. A saturated aqueous sodium hydrogen carbonate solution was added to the reaction mixture, and extraction was carried out using chloroform. After the organic layer was dried over anhydrous magnesium sulfate, the desiccant was removed, and then the solvent was evaporated under reduced pressure. The obtained residue was purified by a silica gel column chromatography (hexane-ethyl acetate). A 4 M hydrogen chloride/dioxane solution (9 ml) was added to a mixture of the obtained purified product and methanol (9 ml), followed by stirring at room temperature for 1 hour. The solvent was evaporated under reduced pressure, thereby obtaining hydrochloride (1.5 g: a molar ratio to hydrogen chloride was not determined) of (3S)-3-methyl-1-[4-(trifluoromethyl)benzyl]piperazine.

Preparation Example 33

A mixture of tert-butyl 4-[2-(piperazin-1-yl-carbonyl)-1H-benzimidazol-6-yl]-piperidine-1-carboxylate (250 mg), 4-formylbenzonitrile (98 mg), acetic acid (68 µl), and dichloromethane (2 ml) was stirred at room temperature for 30 minutes. Sodium triacetoxyborohydride (250 mg) was added to the reaction mixture, followed by stirring at room temperature overnight. A saturated aqueous sodium hydrogen carbonate solution was added to the reaction mixture, and extraction was carried out using chloroform. After the organic layer was dried over anhydrous sodium sulfate, the desiccant was removed, and the solvent was evaporated under reduced pressure. The obtained residue was purified by silica gel column chromatography (chloroform-methanol), thereby obtaining tert-butyl 4-(2-{[4-(4-cyanobenzyl)piperazin-1-yl]-carbonyl}-1H-benzimidazol-6-yl)piperidine-1-carboxylate (330 mg) as an oily material.

Preparation Example 34

A mixture of methyl 3,4-diaminobenzoate (1.3 g), 1-(tert-butoxycarbonyl)piperidine-4-carboxylic acid (1.8 g), triphenyl phosphite (2.5 ml), and pyridine (5.2 ml) was heated to reflux for 18 hours, and then cooled to room temperature. After the solvent was evaporated under reduced pressure, a solution of the obtained residue in ethyl acetate (50 ml) was washed with 1 M hydrochloric acid, water, a 1 M aqueous sodium hydrogen carbonate solution and a saturated aqueous sodium chloride solution in this order, and then dried over anhydrous sodium sulfate. The desiccant was removed, and then the solvent was evaporated under reduced pressure. The obtained residue was purified by silica gel column chromatography (hexane-ethyl acetate), thereby obtaining methyl 2-[1-(tert-butoxycarbonyl)piperidin-4-yl]-1H-benzimidazole-5-carboxylate (1.3 g).

Preparation Example 35

Trifluoroacetic acid (1.9 ml) was added to a mixture of 4-bromo-5-fluorobenzene-1,2-diamine (2.0 g), methyl 2,2,2-trichloroacetimidate (1.5 ml), dichloromethane (57 ml), and diethyl ether (85 ml), followed by stirring at room temperature for 3 hours. After the insoluble material was removed, a 1 M aqueous sodium hydroxide solution (100 ml) was added to the filtrate, followed by concentrating under reduced pressure. Diethyl ether (50 ml) and methanol (50 ml) were added to the obtained residue, followed by stirring at room temperature overnight. Ether (100 ml) was added to the mixture, and after liquid-liquid partition, the aqueous layer was concentrated under reduced pressure. Concentrated hydrochloric acid was added to the obtained mixture to adjust pH to be pH 4.0 to 4.5. The resulting solid was collected by filtration, and then dried under reduced pressure, thereby obtaining 5-bromo-6-fluoro-1H-benzimidazole-2-carboxylic acid (1.5 g) as a solid.

Preparation Example 36

Trifluoroacetic acid (5.1 ml) was added to a mixture of 5-bromopyridine-2,3-diamine (5.0 g), methyl 2,2,2-trichloroacetimidate (4.1 ml), and acetic acid (30 ml), followed by stirring at room temperature overnight. The resulting solid was collected by filtration, and then dried under reduced pressure, thereby obtaining 6-bromo-2-(trichloromethyl)-1H-imidazo[4,5-b]pyridine (4.3 g) as a solid.

Preparation Example 37

After methyl dichloro(methoxy)acetate (2.5 ml) was added to a solution of 4-bromo-$N^1$-methylbenzene-1,2-diamine (1.0 g), N,N-diisopropylethylamine (7.1 ml) in 1,2-dichloroethane (30 ml), the reaction mixture was stirred at room temperature for 1 hour, and then stirred at 60° C. for 3 days. After the reaction mixture was cooled to room temperature, a saturated aqueous sodium hydrogen carbonate solution was added thereto, and extraction was carried out using chloroform. After the organic layer was dried over anhydrous sodium sulfate, the desiccant was removed, and the solvent was evaporated under reduced pressure. The obtained residue was purified by silica gel column chromatography (hexane-ethyl acetate), thereby obtaining methyl 5-bromo-1-methyl-1H-benzimidazole-2-carboxylate (820 mg) as a solid.

Preparation Example 38

N-bromosuccinimide (480 mg) was added to a mixture of methyl 3-methyl-1H-indole-2-carboxylate (500 mg), trifluoroacetic acid (410 µl), and THF (10 ml), followed by stirring at room temperature for 30 minutes. A saturated aqueous sodium thiosulfate solution was added to the reaction mixture, and extraction was carried out using hexane-ethyl acetate. The organic layer was washed with a saturated aqueous sodium hydrogen carbonate solution and a saturated aqueous sodium chloride solution in this order, and dried over anhydrous sodium sulfate. The desiccant was removed, and then the solvent was evaporated under reduced pressure. The obtained residue was purified by silica gel column chromatography (hexane-ethyl acetate), thereby obtaining methyl 5-bromo-3-methyl-1H-indole-2-carboxylate (470 mg) as a solid.

Preparation Example 39

A mixture of tert-butyl 4-{[2-amino-5-(methoxycarbonyl)phenyl]ethynyl}piperidine-1-carboxylate (920 mg), copper (II) acetate (93 mg), and 1,2-dichloroethane (18 ml) was reacted at 150° C. for 1 hour in a sealed tube using a microwave reaction apparatus (manufactured by Biotage), followed by cooling to room temperature. After a mixture of tert-butyl 4-{[2-amino-5-(methoxycarbonyl)phenyl]ethynyl}piperidine-1-carboxylate (920 mg), copper(II) acetate (93 mg), and 1,2-dichloroethane (18 ml) was processed in the same manner as described above, the two reaction mixtures were combined, the reaction mixture was diluted with chloroform, and washed with water. After the organic layer was dried over anhydrous sodium sulfate, the desiccant was removed, and the solvent was evaporated under reduced pressure. The residue was purified by silica gel column chromatography (chloroform-methanol), thereby obtaining methyl 2-[1-(tert-butoxycarbonyl)piperidin-4-yl]-1H-indole-5-carboxylate (1.7 g) as a solid.

Preparation Example 40

After thionyl chloride (8.9 ml) and DMF (50 μl) were added to a solution of [4-(difluoromethyl)phenyl]methanol (4.8 g) in 1,2-dichloroethane (64 ml) at room temperature, the reaction mixture was stirred at 80° C. overnight, and then cooled to room temperature. The reaction mixture was concentrated under reduced pressure, thereby obtaining 1-(chloromethyl)-4-(difluoromethyl)benzene (4.4 g) as an oily material.

Preparation Example 65

Trifluoroacetic acid (1 ml) was added to a solution of tert-butyl 4-[2-({4-[4-(trifluoromethyl)benzyl]piperazin-1-yl}carbonyl)-1H-benzimidazol-5-yl]piperidine-1-carboxylate (270 mg) in dichloromethane (2 ml), followed by stirring at room temperature for 30 minutes. A saturated aqueous sodium hydrogen carbonate solution was added to the reaction mixture, and extraction was carried out using chloroform. The organic layer was washed with a saturated aqueous sodium chloride solution, and dried over anhydrous sodium sulfate. The desiccant was removed, and then the solvent was evaporated under reduced pressure. The obtained residue was purified by amino silica gel column chromatography (chloroform-methanol), thereby obtaining [5-(piperidin-4-yl)-11-1-benzimidazol-2-yl]{4-[4-(trifluoromethyl)benzyl]piperazin-1-yl}methanone (150 mg) as an amorphous material.

Preparation Example 92

N-[3-(dimethylamino)propyl]-N'-ethylcarbodiimide hydrochloride (1.2 g) was added to a mixture of 7-bromoimidazo[1,2-a]pyridine-2-carboxylic acid (1.0 g), 1-[4-(trifluoromethyl)benzyl]piperazine (1.1 g), 1H-benzotriazol-1-ol (840 mg), and DMF (10 ml), followed by stirring at room temperature overnight. The solvent was evaporated under reduced pressure, and then a saturated aqueous sodium hydrogen carbonate solution was added to the obtained residue, followed by stirring at room temperature for 1 hour. The resulting solid was collected by filtration, followed by drying under reduced pressure, thereby obtaining (7-bromoimidazo[1,2-a]pyridin-2-yl){4-[4-(trifluoromethyl)benzyl]piperazin-1-yl}methanone (1.7 g) as a solid.

Preparation Example 100

A mixture of (7-bromoimidazo[1,2-a]pyridin-2-yl){4-[4-(trifluoromethyl)benzyl]piperazin-1-yl}methanone (1.7 g), tert-butyl 4-(4,4,5,5-tetramethyl-1,3,2-dioxaborolan-2-yl)-3,6-dihydropyridine-1(2H)-carboxylate (2.3 g), tetrakis(triphenylphosphine)palladium (1.3 g), 2 M aqueous sodium carbonate solution (15 ml), and dioxane (58 ml) was stirred at 100° C. overnight in an argon atmosphere, and then cooled to room temperature. A saturated aqueous sodium hydrogen carbonate solution and ethyl acetate were added to the reaction mixture. The insoluble material was removed, and after liquid-liquid partition, extraction was carried out on the aqueous layer using ethyl acetate. The collected organic layer was washed with a saturated aqueous sodium chloride solution, and then dried over anhydrous sodium sulfate. The desiccant was removed, and then the solvent was evaporated under reduced pressure. The obtained residue was purified by silica gel column chromatography (chloroform-methanol) and an amino silica gel column chromatography (chloroform-methanol), and then diethyl ether (60 ml) was added to the obtained solid (2.7 g), followed by stirring at room temperature for 1 hour. The solid was collected by filtration, followed by drying under reduced pressure, thereby obtaining tert-butyl 4-[2-({4-[4-(trifluoromethyl)benzyl]piperazin-1-yl}carbonyl)imidazo[1,2-a]pyridin-7-yl]-3,6-dihydropyridine-1(2H)-carboxylate (1.9 g) as a solid.

Preparation Example 107

Trifluoroacetic acid (6 ml) was added to a solution of tert-butyl 4-[2-({4-[4-(trifluoromethyl)benzyl]piperazin-1-yl}carbonyl)imidazo[1,2-a]pyridin-7-yl]piperidine-1-carboxylate (1.8 g) in dichloromethane (12 ml), followed by stirring at room temperature for 30 minutes. After concentrating under reduced pressure, a saturated aqueous sodium hydrogen carbonate solution was added to the obtained residue, and then extraction was carried out using chloroform. After the organic layer was dried over anhydrous sodium sulfate, the desiccant was removed, and the solvent was evaporated under reduced pressure. Chloroform (20 ml) was added to the obtained residue, followed by stirring at room temperature for 30 minutes. The insoluble material was removed, and then the solvent was evaporated under reduced pressure. The obtained residue was purified by amino silica gel column chromatography (chloroform-methanol), thereby obtaining [7-(piperidin-4-yl)imidazo[1,2-a]pyridin-2-yl]{4-[4-(trifluoromethyl)benzyl]piperazin-1-yl}methanone (860 mg) as an oily material.

Preparation Example 109

20% palladium hydroxide-activated charcoal (about 50% water-containing product, 560 mg) was added to a mixture of tert-butyl 4-[2-({4-[4-(trifluoromethyl)benzyl]piperazin-1-yl}carbonyl)imidazo[1,2-a]pyridin-7-yl]-3,6-dihydropyridine-1(2H)-carboxylate (1.9 g), THF (20 ml), and methanol (20 ml), followed by stirring at room temperature for 1.5 hours in a hydrogen atmosphere. The insoluble material was removed, and then the solvent was evaporated under reduced pressure. The obtained residue was purified by amino silica gel column chromatography (hexane-ethyl acetate), thereby obtaining tert-butyl 4-[2-({4-[4-(trifluoromethyl)benzyl]piperazin-1-yl}carbonyl)imidazo[1,2-a]pyridin-7-yl]piperidine-1-carboxylate (1.8 g) as a solid.

Preparation Example 165

Sodium borohydride (2.6 g) was added in parts at plural times to a solution of ethyl 5-ethoxypyrazine-2-carboxylate (4.5 g) in methanol (100 ml) under ice-cooling, followed by stirring at room temperature for 6 hours. 1 M hydrochloric acid was added to the reaction mixture to adjust pH to be 4, followed by stirring at room temperature for 15 minutes. A 1 M aqueous sodium hydroxide solution was added to the mixture to adjust pH to be 9, and then extraction was carried out using chloroform. After the organic layer was dried over anhydrous sodium sulfate, the desiccant was removed, and the solvent was evaporated under reduced pressure. The obtained residue was purified by silica gel column chromatography (hexane-ethyl acetate), thereby obtaining (5-ethoxypyrazin-2-yl)methanol (2.6 g) as an oily material.

Preparation Example 166

Thionyl chloride (200 µl) was added to a solution of (5-ethoxypyrazin-2-yl)methanol (150 mg) in dichloromethane (3 ml) under ice-cooling, followed by stirring at room temperature for 30 minutes. The reaction mixture was concentrated under reduced pressure, thereby obtaining 2-(chloromethyl)-5-ethoxypyrazine (160 mg) as an oily material.

Preparation Example 167

A 1 M aqueous sodium hydroxide solution (2.8 ml) was added to a solution of 2,2,2-trifluoro-1-{4-[(5-{1-[(6-methoxypyridin-3-yl)methyl]piperidin-4-yl}-1H-benzimidazol-2-yl)carbonyl]piperazin-1-yl}ethanone (1.3 g) in methanol (7 ml), followed by stirring at room temperature for 5 hours. A saturated aqueous sodium sulfate solution was added to the reaction mixture, and extraction was carried out using a mixed solvent of chloroform and 2-propanol. After the organic layer was dried over anhydrous sodium sulfate, the desiccant was removed, and then the solvent was evaporated under reduced pressure, thereby obtaining (5-{1-[(6-methoxypyridin-3-yl)methyl]piperidin-4-yl}-1H-benzimidazol-2-yl)(piperazin-1-yl)methanone (1.1 g) as an oily material.

Preparation Example 168

A mixture of 5-bromo-1H-benzimidazol-2-carboxylic acid (3.0 g), tert-butyl 4-(4,4,5,5-tetramethyl-1,3,2-dioxaborolan-2-yl)-3,6-dihydropyridine-1(2H)-carboxylate (7.7 g), dichloro[1,1'-bis(di-tert-butylphosphino)ferrocene]palladium (410 mg), 2 M aqueous sodium carbonate solution (50 ml), and dioxane (75 ml) was stirred at 95° C. overnight in an argon atmosphere, and then cooled to room temperature. After water (170 ml) and ethyl acetate (200 ml) were added to the reaction mixture, the reaction mixture was stirred for 20 minutes, and then subjected to liquid-liquid partition. The aqueous layer was washed with ethyl acetate (50 ml), and then citric acid was added thereto to adjust pH to be 6 to 7. The resulting solid was collected by filtration, and then dried under reduced pressure, thereby obtaining 5-[1-(tert-butoxycarbonyl)-1,2,3,6-tetrahydropyridin-4-yl]-1H-benzimidazole-2-carboxylic acid (2.7 g) as a solid.

Preparation Example 169

10% palladium-activated charcoal (about 50% water-containing product, 230 mg) was added to a mixture of tert-butyl 4-(2-{[4-(4-cyanobenzyl)piperazin-1-yl]carbonyl}-1H-indol-6-yl)-3,6-dihydropyridine-1(2H)-carboxylate (470 mg), THF (14 ml), and ethanol (3 ml), followed by stirring at room temperature for 2 hours in a hydrogen atmosphere. After the insoluble material was removed, solvent was evaporated under reduced pressure, and then 10% palladium-activated charcoal (about 50% water-containing product, 230 mg) was added to a mixture of the obtained residue, THF (14 ml), and ethanol (3 ml), followed by stirring at room temperature overnight in a hydrogen atmosphere. After the insoluble material was removed, the solvent was evaporated under reduced pressure. After 20% palladium hydroxide-activated charcoal (about 50% water-containing product, 230 mg) was added to a mixture of the obtained residue, THF (14 ml), and ethanol (3 ml), the reaction mixture was stirred at room temperature for 4 hours in a hydrogen atmosphere of 3.0 kgf/cm$^2$, and then left to stand for 3 days. The insoluble material was removed, and then the solvent was evaporated under reduced pressure. The obtained residue was purified by amino silica gel column chromatography (chloroform-methanol), thereby obtaining tert-butyl 4-[2-(piperazin-1-ylcarbonyl)-1H-indol-6-yl]piperidine-1-carboxylate (360 mg) as an oily material.

Preparation Example 170

A mixture of 5-ethylpyrazine-2-carboxylic acid (2.3 g), benzyl bromide (2.3 ml), potassium carbonate (4.0 g), and DMF (20 ml) was stirred at 80° C. for 1 hour, and then cooled to room temperature. Ethyl acetate was added to the reaction mixture, followed by washing with a saturated aqueous sodium chloride solution. After the organic layer was dried over anhydrous sodium sulfate, the desiccant was removed, and the solvent was evaporated under reduced pressure. The obtained residue was purified by silica gel column chromatography (hexane-ethyl acetate), thereby obtaining benzyl 5-ethylpyrazine-2-carboxylate (3.0 g) as an oily material.

Preparation Example 171

A mixture of 2,2,2-trifluoro-1-(4-{[5-(piperidin-4-yl)-1H-benzimidazol-2-yl]carbonyl}piperazin-1-yl)ethanone hydrochloride (2.0 g), 6-methoxynicotinaldehyde (680 mg), triethylamine (1.2 ml), and dichloromethane (80 ml) was stirred at room temperature for 10 minutes, and then acetic acid (1.3 ml) was added thereto, followed by stirring at room temperature for 30 minutes. Sodium triacetoxyborohydride (6.6 g) was added to the reaction mixture, followed by stirring at room temperature overnight. 6-methoxynicotinaldehyde (340 mg) and acetic acid (650 µl) were added to the reaction mixture, followed by stirring at room temperature for 30 minutes. After sodium triacetoxyborohydride (3.2 g) was added to the reaction mixture, the reaction mixture was stirred at room temperature for 6 hours, and then left to stand at room temperature for 3 days. After a saturated aqueous sodium hydrogen carbonate solution was added to the reaction mixture, the reaction mixture was stirred at room temperature for 1 hour, and then extraction was carried out using chloroform. After the organic layer was dried over anhydrous sodium sulfate, the desiccant was removed, and the solvent was evaporated under reduced pressure. The obtained residue was purified by silica gel column chromatography (chloroform-methanol), thereby obtaining 2,2,2-trifluoro-1-{4-[(5-{1-[(6-methoxypyridin-3-yl)methyl]piperidin-4-yl}-1H-benzimidazol-2-yl)carbonyl]piperazin-1-yl}ethanone (1.3 g) as an oily material.

Example 1

A mixture of hydrochloride (200 mg) of [5-(piperidin-4-yl)-1H-benzimidazol-2-yl]{4-[4-(trifluoromethyl)benzyl]piperazin-1-yl}methanone obtained in the same manner as in Preparation Example 20, 6-methoxynicotinaldehyde (100 mg), triethylamine (140 µl), acetic acid (100 µl), and dichloromethane (4 ml) was stirred at room temperature for 10 minutes. After sodium triacetoxyborohydride (580 mg) was added to the reaction mixture at room temperature, the reaction mixture was stirred at room temperature for 2 hours, and then left to stand at room temperature overnight. A saturated aqueous sodium hydrogen carbonate solution was added to the reaction mixture, and extraction was carried out using chloroform. After the organic layer was dried over anhydrous sodium sulfate, the desiccant was removed, and then the solvent was evaporated under reduced pressure. After the obtained crude product was purified by amino silica gel column chromatography (chloroform-methanol), tosic acid monohydrate (69 mg) was added to a solution of the obtained oily material (110 mg) in acetone, and then the solvent was evaporated under reduced pressure. Ethanol (3 ml) and diisopropyl ether (20 ml) were added to the obtained residue, followed by stirring at room temperature. The resulting solid was collected by filtration, and then dried under reduced pressure, thereby obtaining (5-{1-[(6-methoxypyridin-3-yl)methyl]piperidin-4-yl}-1H-benzimidazol-2-yl){4-[4-(trifluoromethyl)benzyl]piperazin-1-yl}methanone ditosylate (180 mg) as an amorphous material. In addition, after the crude product obtained in the same manner as above was purified by amino silica gel column chromatography (chloroform-methanol), a mixture of the solid (200 mg) obtained by drying under reduced pressure after pulverising using acetonitrile and acetonitrile (10 ml) was stirred at 95° C. for 30 minutes, and tosic acid monohydrate (130 mg) was added thereto. The mixture was cooled to room temperature while stirring, and then stirred at room temperature for 7 days. The resulting solid was collected by filtration, and then dried under reduced pressure, thereby obtaining (5-{1-[(6-methoxypyridin-3-yl) methyl]piperidin-4-yl}-1H-benzimidazol-2-yl){4-[4-(trifluoromethyl)benzyl]piperazin-1-yl}methanone ditosylate (300 mg) as a crystal. The powder X-ray diffraction data of this crystal are shown in Tables below.

Example 2

A mixture of [1-(piperidin-4-yl)-1H-indol-5-yl]{4-[4-(trifluoromethyl)benzyl]piperazin-1-yl}methanone (150 mg), 6-methoxynicotinaldehyde (66 mg), acetic acid (27 µl), and dichloromethane (7.5 ml) was stirred at room temperature for 30 minutes. After sodium triacetoxyborohydride (170 mg) was added to the reaction mixture, the reaction mixture was stirred at room temperature for 2 hours, and then left to stand at room temperature overnight. A saturated aqueous sodium hydrogen carbonate solution was added to the reaction mixture, and extraction was carried out using chloroform. After the organic layer was dried over anhydrous sodium sulfate, the desiccant was removed, and then the solvent was evaporated under reduced pressure. The obtained residue was purified by silica gel column chromatography (chloroform-methanol), and tosic acid monohydrate (100 mg) was added to a solution of the obtained oily material (160 mg) in acetone (2 ml). After the solvent was evaporated under reduced pressure, ethanol and diisopropyl ether were added to the obtained residue. The reaction mixture was heated to reflux while stirring, and then cooled to room temperature. The resulting solid was collected by filtration, and then dried under reduced pressure. The obtained solid was purified by ODS column chromatography (acetonitrile-water-trifluoroacetic acid), and then the solvent in the obtained fraction was evaporated under reduced pressure. A saturated aqueous sodium hydrogen carbonate solution was added to the obtained residue, and then extraction was carried out using chloroform. After the organic layer was dried over anhydrous sodium sulfate, the desiccant was removed, and then the solvent was evaporated under reduced pressure. Tosic acid monohydrate (91 mg) was added to a solution of the obtained oily material (140 mg) in acetone (2 ml). Ethanol and diisopropyl ether were added to the obtained residue, followed by stirring at room temperature. The resulting solid was collected by filtration, and then dried under reduced pressure, thereby obtaining (1-{1-[(6-methoxypyridin-3-yl)methyl]piperidin-4-yl}-1H-indol-5-yl){4-[4-(trifluoromethyl)benzyl]piperazin-1-yl}methanone ditosylate (190 mg) as a solid.

Example 3

A mixture of [2-(piperidin-4-yl)-1H-benzimidazol-6-yl]{4-[4-(trifluoromethyl)benzyl]piperazin-1-yl}methanone (100 mg), 4-methoxybenzaldehyde (39 µl), acetic acid (18 µl), and dichloromethane (3.4 ml) was stirred at room temperature for 30 minutes. After sodium triacetoxyborohydride (110 mg) was added to the reaction mixture, the reaction mixture was stirred at room temperature for 2 hours, and then left to stand at room temperature overnight. A saturated aqueous sodium hydrogen carbonate solution was added to the reaction mixture, and extraction was carried out using chloroform. After the organic layer was dried over anhydrous sodium sulfate, the desiccant was removed, and then the solvent was evaporated under reduced pressure. After the obtained residue was purified by silica gel column chromatography (chloroform-methanol), a 4 M hydrogen chloride/dioxane solution was added to a solution of the obtained oily material (120 mg) in dioxane, and then the solvent was evaporated under reduced pressure. Ethyl acetate and hexane were added to the obtained residue, followed by stirring at room temperature. The resulting solid was collected by filtration, and then dried under reduced pressure, thereby obtaining {2-[1-(4-methoxybenzyl)piperidin-4-yl]-1H-benzimidazol-6-yl}{4-[4-(trifluoromethyl) benzyl]piperazin-1-yl}methanone dihydrochloride (82 mg) as a solid.

Example 4

A mixture of [1-(piperidin-4-yl)-1H-indol-5-yl]{4-[4-(trifluoromethyl)benzyl]piperazin-1-yl}methanone (150 mg), 4-methoxybenzaldehyde (58 µl), acetic acid (27 µl), and dichloromethane (5 ml) was stirred at room temperature for 30 minutes. After sodium triacetoxyborohydride (170 mg) was added to the reaction mixture, the reaction mixture was stirred at room temperature for 2 hours, and then left to stand at room temperature overnight. A saturated aqueous sodium hydrogen carbonate solution was added to the reaction mixture, and extraction was carried out using chloroform. After the organic layer was dried over anhydrous sodium sulfate, the desiccant was removed, and then the solvent was evaporated under reduced pressure. The obtained residue was purified by silica gel column chromatography (chloroform-methanol), and tosic acid monohydrate (120 mg) was added to a solution of the obtained oily material (190 mg) in acetone (2 ml). After the solvent was evaporated under reduced pressure, ethanol and diisopropyl ether were added to the obtained residue, followed by stirring at room temperature. The resulting solid was collected by filtration, and then dried under reduced pressure. The obtained solid was purified by ODS column chromatography (acetonitrile-water-trifluoroacetic acid), and then the solvent in the obtained fraction was evaporated under reduced pressure. A saturated aqueous sodium hydrogen carbonate solution was added to the obtained residue, and then extraction was carried out using chloroform. After the organic layer was dried over anhydrous sodium sulfate, the desiccant was removed, and then the solvent was evaporated under reduced pressure. Tosic acid monohydrate (100 mg) was added to a solution of the obtained oily material (160 mg) in acetone (2 ml). After the solvent was evaporated under reduced pressure, ethanol and diisopropyl ether were added to the obtained residue, followed by stirring at room temperature. The resulting solid was collected by filtration, and then dried under reduced pressure. The obtained solid was purified by ODS column chromatography (acetonitrile-water-trifluoroacetic acid), and then the solvent in the obtained fraction was evaporated under reduced pressure. A saturated aqueous sodium hydrogen carbonate solution was added to the obtained residue, and then extraction was carried out using chloroform. After the organic layer was dried over anhydrous sodium sulfate, the desiccant was removed, and then the solvent was evaporated under reduced pressure. A 4 M hydrogen chloride/dioxane solution was added to a solution of the obtained oily material (78 mg) in dioxane, and then the solvent was evaporated under reduced pressure. Ethanol and diisopropyl ether were added to the obtained residue, followed by stirring at room temperature. The resulting solid was collected by filtration, and then dried under reduced pressure, thereby obtaining {1-[1-(4-methoxybenzyl)piperidin-4-yl]-1H-indol-5-yl}{4-[4-(trifluoromethyl)benzyl]piperazin-1-yl}methanone dihydrochloride (77 mg) as a solid.

Example 5

Sodium triacetoxyborohydride (200 mg) was added to a mixture of [6-(piperidin-4-yl)-1H-indol-2-yl]{4-[4-(trifluoromethyl)benzyl]piperazin-1-yl}methanone (160 mg), 6-methoxynicotinaldehyde (50 mg), acetic acid (5 µl), and dichloromethane (4 ml) at room temperature, followed by stirring at room temperature for 89 hours. A saturated aqueous sodium hydrogen carbonate solution was added to the reaction mixture, and extraction was carried out using chloroform. Activated charcoal was added to the organic layer, followed by drying over anhydrous magnesium sulfate. The activated charcoal and desiccant were removed, and then the solvent was evaporated under reduced pressure. After the obtained residue was purified by silica gel column chromatography (chloroform-methanol), fumaric acid (25 mg) was added to a suspension of the obtained solid (140 mg) in methanol, and then the solvent was evaporated under reduced pressure. Diethyl ether was added to the obtained residue, and then the solvent was evaporated under reduced pressure. After heptane was added to the obtained residue, the resulting solid was collected by filtration, and then heated to dry under reduced pressure, thereby obtaining (6-{1-[(6-methoxypyridin-3-yl)methyl]piperidin-4-yl}-1H-indol-2-yl){4-[4-(trifluoromethyl)benzyl]piperazin-1-yl}methanone fumarate (130 mg) as a solid.

Example 6

A mixture of [5-(piperidin-4-yl)-1,3-benzothiazol-2-yl]{4-[4-(trifluoromethyl)benzyl]piperazin-1-yl}methanone (43 mg), 6-methoxynicotinaldehyde (14 mg), acetic acid (10 µl), and dichloromethane (2 ml) was stirred at room temperature for 1 hour. Sodium triacetoxyborohydride (37 mg) was added to the reaction mixture, followed by stirring at room temperature overnight. A saturated aqueous sodium hydrogen carbonate solution was added to the reaction mixture, and extraction was carried out using chloroform. The organic layer was washed with a saturated aqueous sodium chloride solution, and dried over anhydrous sodium sulfate. The desiccant was removed, and then the solvent was evaporated under reduced pressure. After the obtained residue was purified by silica gel column chromatography (chloroform-methanol), ethanol was added to the obtained oily material. The resulting solid was collected by filtration, and then dried under reduced pressure, thereby obtaining (5-{1-[(6-methoxypyridin-3-yl)methyl]piperidin-4-yl}-1,3-benzothiazol-2-yl){4-[4-(trifluoromethyl)benzyl]piperazin-1-yl}methanone (11 mg) as a solid.

Example 7

2-(Chloromethyl)-5-methoxypyrazine (16 mg) was added to a mixture of [5-(piperidin-4-yl)-1H-benzimidazol-2-yl]{(4-[4-(trifluoromethyl)benzyl]piperazin-1-yl}methanone (47 mg), N,N-diisopropylethylamine (68 µl), acetonitrile (1 ml), and DMF (1 ml), followed by stirring at room temperature for 5 days. Water was added to the reaction mixture, and extraction was carried out using ethyl acetate. After the organic layer was dried over anhydrous sodium sulfate, the desiccant was removed, and then the solvent was evaporated under reduced pressure. After the obtained crude product was purified by silica gel column chromatography (chloroform-methanol), tosic acid monohydrate (24 mg) and ethyl acetate (3 ml) were added to a solution of the obtained oily material (38 mg) in acetone (2 ml), followed by stirring at room temperature overnight. The resulting solid was collected by filtration, and then dried under reduced pressure, thereby obtaining (5-{1-[(5-methoxypyrazin-2-yl)methyl]piperidin-4-yl}-1H-benzimidazol-2-yl){4-[4-(trifluoromethyl)benzyl]piperazin-1-yl}methanone ditosylate (53 mg) as a solid. In addition, a mixture of the solid (200 mg) obtained after the crude product obtained in the same manner as above was purified by amino silica gel column chromatography (hexane-ethyl acetate), acetone (18 ml), and acetonitrile (3 ml) was stirred at 80° C., and then tosic acid monohydrate (130 mg) was added thereto. The mixture was cooled to room temperature while stirring, and then stirred at room temperature for 72 hours. The resulting solid was collected by filtration, and then dried under reduced pressure, thereby obtaining (5-{1-[(5-methoxypyrazin-2-yl)methyl]piperidin-4-yl}-1H-benzimidazol-2-yl){4-[4-(trifluoromethyl)benzyl]piperazin-1-yl}methanone ditosylate (300 mg) as a crystal. The powder X-ray diffraction data of this crystal are shown in Tables below.

Example 8

2-(Chloromethyl)-5-methylpyrazine hydrochloride (19 mg) was added to a mixture of [5-(piperidin-4-yl)-1H-benzimidazol-2-yl]{4-[4-(trifluoromethyl)benzyl]piperazin-1-yl}methanone (48 mg), N,N-diisopropylethylamine (70 µl), acetonitrile (1 ml), and DMF (1 ml), followed by stirring at room temperature for 5 days. Water was added to the reaction mixture, and extraction was carried out using ethyl acetate. After the organic layer was dried over anhydrous sodium sulfate, the desiccant was removed, and then the solvent was evaporated under reduced pressure. The obtained residue was purified by silica gel column chromatography (chloroform-methanol), and then a 4 M hydrogen chloride/ethyl acetate solution (200 µl) was added to a solution of the obtained oily material in ethyl acetate (1 ml), followed by stirring at room temperature for 10 minutes. The solvent was evaporated under reduced pressure, and then ethyl acetate was added to the obtained residue. The resulting solid was collected by filtration, and then dried under reduced pressure, thereby obtaining (6-{1-[(5-methylpyrazin-2-yl)methyl]piperidin-4-yl}-1H-benzimidazol-2-yl)

{4-[4-(trifluoromethyl)benzyl]piperazin-1-yl}methanone trihydrochloride (55 mg) as a solid.

Example 36

Sodium triacetoxyborohydride (720 mg) was added to a mixture of [7-(piperidin-4-yl)imidazo[1,2-a]pyridin-2-yl]{4-[4-(trifluoromethyl)benzyl]piperazin-1-yl}methanone (200 mg), 6-methoxynicotinaldehyde (87 mg), acetic acid (110 µl), and dichloromethane (8 ml) at room temperature, followed by stirring at room temperature overnight. A saturated aqueous sodium hydrogen carbonate solution was added to the reaction mixture, and extraction was carried out using chloroform. After the organic layer was dried over anhydrous sodium sulfate, the desiccant was removed, and then the solvent was evaporated under reduced pressure. After the obtained residue was purified by amino silica gel column chromatography (hexane-ethyl acetate), tosic acid monohydrate (130 mg) was added to a solution of the obtained solid (200 mg) in methanol (10 ml), and then the solvent was evaporated under reduced pressure. After hexane (20 ml) was added to a suspension of the obtained solid in acetone (10 ml), the solid was collected by filtration, and then dried under reduced pressure, thereby obtaining (7-{1-[(6-methoxypyridin-3-yl)methyl]piperidin-4-yl}imidazo[1,2-a]pyridin-2-yl){4-[4-(trifluoromethyl)benzyl]piperazin-1-yl}methanone ditosylate (260 mg) as a solid.

Example 59

A mixture of (5-{1-[(6-methoxypyridin-3-yl)methyl]piperidin-4-yl}-1H-benzimidazol-2-yl)(piperazin-1-yl)methanone (100 mg), 4-chlorobenzaldehyde (42 mg), acetic acid (40 µl), and dichloromethane (1 ml) was stirred at room temperature for 30 minutes. Sodium triacetoxyborohydride (150 mg) was added to the reaction mixture, followed by stirring at room temperature overnight. Sodium hydrogen carbonate, water, and chloroform were added to the reaction mixture, and liquid-liquid partition was carried out by Presep (diatomaceous earth, granular shape, manufactured by Wako Pure Chemical Industries, Ltd.). Extraction was performed on the aqueous layer using chloroform, and then the solvent of the collected organic layer was evaporated under reduced pressure. The obtained residue was purified by silica gel column chromatography (chloroform-methanol), and then tosic acid monohydrate (82 mg) was added to a mixture of the obtained oily material, acetonitrile (1 ml), and chloroform (2 ml), followed by stirring at room temperature for 1 hour. The solvent was evaporated under reduced pressure, and then ether (50 ml) was added to a solution of the obtained residue in chloroform (1 ml), followed by stirring at room temperature for 30 minutes. The resulting solid was collected by filtration, and then dried under reduced pressure, thereby obtaining [4-(4-chlorobenzyl)piperazin-1-yl](6-{1-[(6-methoxypyridin-3-yl)methyl]piperidin-4-yl}-1H-benzimidazol-2-yl)methanone ditosylate (160 mg) as a solid.

In the same manner as methods of Preparation Examples and Examples described above, compounds of Preparation Examples and Examples shown in the following tables were prepared. Structures, manufacturing methods and physicochemical data of Preparation Example compounds and Example compounds are shown in the following tables.

Moreover, the following abbreviations are used in the following tables.

Pre: Preparation Example No, Ex: Example No, Str: Chemical Structure Formula, Syn: Preparation Method (It represents Preparation Example No. or Example No. prepared by the same method among Examples/Preparation Examples described above. Here, P before a number represents Preparation Example, and E represents Example, respectively. For example, it indicates that the compound in Preparation Example 41 is prepared by the same method as in the compound in Preparation Example 1, and the compound in Example 9 is prepared by the same method as in the compound in Example 1, respectively. In addition, as Syn, two Preparation Examples are described in some Example compounds, and this indicates that the Example compound is prepared by carrying out two Preparation Methods described in Syn in the description order. For example, it indicates that the compound in Example 55 is prepared by the same method as in Preparation Example 1 using the compound prepared in the same method as in Example 21 as a starting material.), Dat: physicochemical data, ESI+: m/z value in mass spectrometry (ionization method ESI, [M+H]⁺ unless otherwise specified), ESI−: m/z values in mass spectrometry (ionization method ESI, [M−H]⁻ unless otherwise specified), APCI/ESI: APCI/ESI-MS (atmospheric pressure chemical ionization APCI, APCI/ESI refers to the simultaneous measurement of APCI and ESI APCI/ESI+ is [M+H]⁺, APCI/ESI− is [M−H]⁻ unless otherwise specified), CI: CI[M+H]⁺, NMR1: δ (ppm) of peak in ¹H-NMR in CD₃OD, NMR2: δ (ppm) of peak in ¹H-NMR in DMSO-d₆, Me: methyl, Et: ethyl, iPr: isopropyl, Boc: tert-butoxycarbonyl, Cbz: benzyloxycarbonyl.

Further, in the chemical structure formulas, HCl indicates that the compound is hydrochloride, 2HCl indicates that the compound is dihydrochloride, 3HCl indicates that the compound is trihydrochloride, xHCl indicates that the compound is hydrochloride, but the molar ratio of hydrogen chloride is undetermined, 2TsOH indicates that the compound is ditesilate ditosylate, 3TsOH indicates that the compound is tritosylate, and Fum indicates that the compound is fumarate, respectively.

TABLE 5

| Pre | Syn | Str | Dat |
|---|---|---|---|
| 1 | P1 | Br-[benzimidazole]-C(O)-N[piperazine]N-CH₂-[phenyl]-CF₃ | ESI+: 467, 469 |

TABLE 5-continued

| Pre | Syn | Str | Dat |
|---|---|---|---|
| 2 | P2 | 2-chloroquinoline-6-carbonyl-[4-(4-trifluoromethylbenzyl)piperazine] | ESI+: 434 |
| 3 | P3 | 6-bromo-1H-imidazo[4,5-b]pyridine-2-carbonyl-[4-(4-trifluoromethylbenzyl)piperazine] | ESI+: 468, 470 |
| 4 | P4 | 5-(1-Boc-piperidin-4-yl)-1-methyl-1H-indole-2-carbonyl-[4-(4-trifluoromethylbenzyl)piperazine] | ESI+: 607 [M + Na]+ |
| 5 | P5 | 5-bromo-1-methyl-1H-benzimidazole-2-carbonyl-[4-(4-trifluoromethylbenzyl)piperazine] | APCI/ESI+: 481, 483 |

TABLE 6

| Pre | Syn | Str | Dat |
|---|---|---|---|
| 6 | P6 | 6-bromo-3-methyl-3H-benzimidazole-2-carbonyl-[4-(4-trifluoromethylbenzyl)piperazine] | APCI/ESI+: 481, 483 |

TABLE 6-continued

| Pre | Syn | Str | Dat |
|---|---|---|---|
| 7-1 | P7 | 1-(1-Boc-piperidin-4-yl)-1H-indazole-5-carboxylic acid ethyl ester | ESI+: 374 |
| 7-2 | P7 | 2-(1-Boc-piperidin-4-yl)-2H-indazole-5-carboxylic acid ethyl ester | ESI+: 374 |
| 8 | P8 | 1-[4-(difluoromethyl)benzyl]piperazine | ESI+: 227 |
| 9 | P9 | 5-(1-Boc-1,2,3,6-tetrahydropyridin-4-yl)-2-{[4-(4-trifluoromethylbenzyl)piperazin-1-yl]carbonyl}-1H-benzimidazole | ESI+: 570 |
| 10 | P10 | methyl 4-amino-3-[(1-Boc-piperidin-4-yl)ethynyl]benzoate | ESI+: 381 [M + Na]+ |

TABLE 7

| Pre | Syn | Str | Dat |
|---|---|---|---|
| 11 | P11 | 5-(4-Boc-piperazin-1-yl)-2-{[4-(4-trifluoromethylbenzyl)piperazin-1-yl]carbonyl}-1H-benzimidazole | APCI/ESI+: 573 |

TABLE 7-continued
| Pre | Syn | Str | Dat |
|---|---|---|---|
| 12 | P12 | 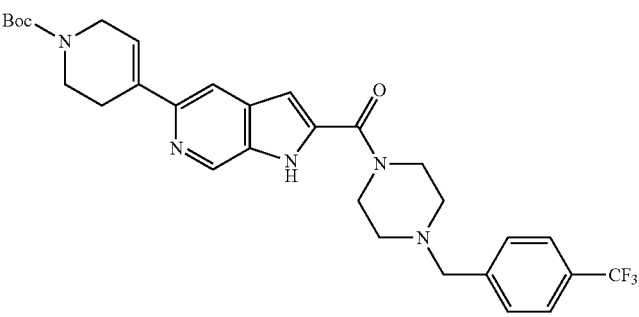 [SMILES: CC(C)(C)OC(=O)N1CC=C(c2cc3cc(C(=O)N4CCN(Cc5ccc(C(F)(F)F)cc5)CC4)[nH]c3cn2)CC1] | APCI/ESI+: 570 |
| 13 | P13 | 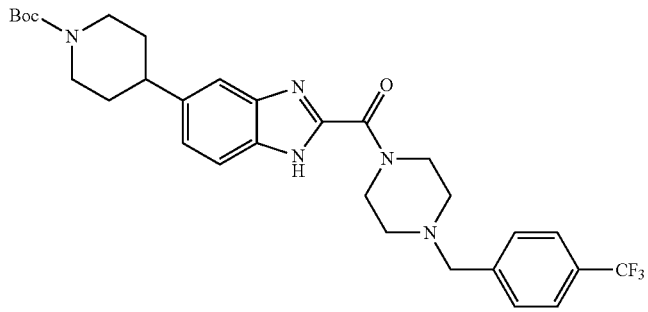 [SMILES: CC(C)(C)OC(=O)N1CCC(c2ccc3[nH]c(C(=O)N4CCN(Cc5ccc(C(F)(F)F)cc5)CC4)nc3c2)CC1] | ESI+: 572 |
| 14 | P14 | 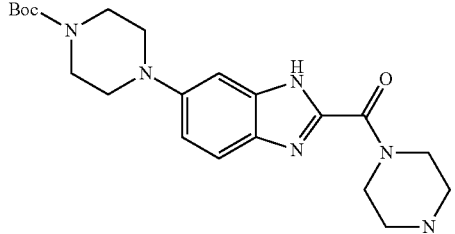 | APCI/ESI+: 414 |
| 15 | P15 | 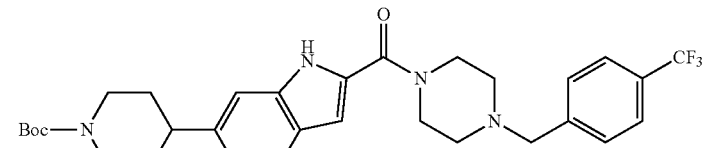 | ESI−: 569 |
TABLE 8
| Pre | Syn | Str | Dat |
|---|---|---|---|
| 16 | P16 | 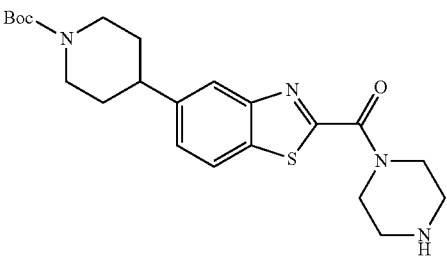 [SMILES: CC(C)(C)OC(=O)N1CCC(c2ccc3sc(C(=O)N4CCNCC4)nc3c2)CC1] | ESI+: 431 |

TABLE 8-continued

| Pre | Syn | Str | Dat |
|---|---|---|---|
| 17 | P17 | (structure) | APCI/ESI+: 573 |
| 18 | P18 | (structure) | ESI−: 371 |
| 19 | P19 | (structure) | APCI/ESI−: 588 |
| 20 | P20 | (structure) ×HCl | ESI+: 472 |

TABLE 9

| Pre | Syn | Str | Dat |
|---|---|---|---|
| 21 | P21 | (structure) | ESI+: 471 |

TABLE 9-continued
| Pre | Syn | Str | Dat |
|---|---|---|---|
| 22 | P22 | 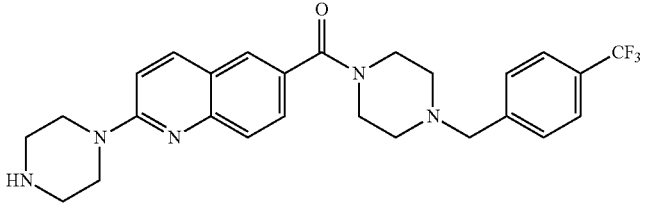 [SMILES: O=C(c1ccc2nc(N3CCNCC3)ccc2c1)N1CCN(Cc2ccc(C(F)(F)F)cc2)CC1] | ESI+: 484 |
| 23 | P23 | 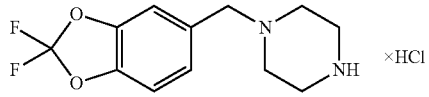 [SMILES: FC1(F)Oc2ccc(CN3CCNCC3)cc2O1] | APCI/ESI+: 257 |
| 24 | P24 | 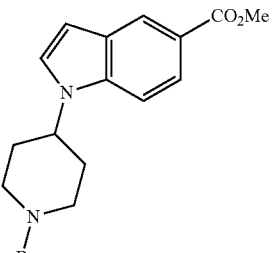 | ESI+: 359 |
| 25 | P25 | 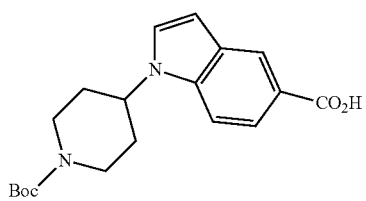 [SMILES: CC(C)(C)OC(=O)N1CCC(n2ccc3cc(C(=O)O)ccc32)CC1] | ESI+: 345 |
| 26 | P26 | 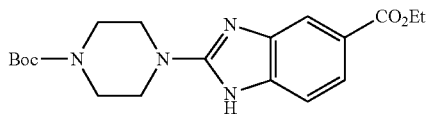 [SMILES: CCOC(=O)c1ccc2[nH]c(N3CCN(C(=O)OC(C)(C)C)CC3)nc2c1] | ESI+: 375 |
TABLE 10
| Pre | Syn | Str | Dat |
|---|---|---|---|
| 27 | P27 | 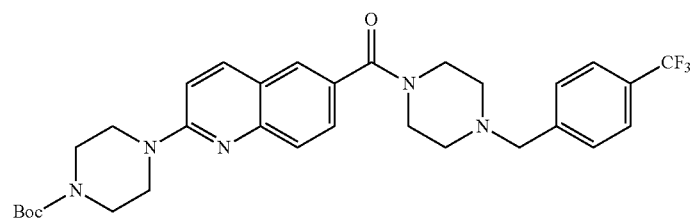 [SMILES: CC(C)(C)OC(=O)N1CCN(c2ccc3cc(C(=O)N4CCN(Cc5ccc(C(F)(F)F)cc5)CC4)ccc3n2)CC1] | ESI+: 584 |
| 28 | P28 | 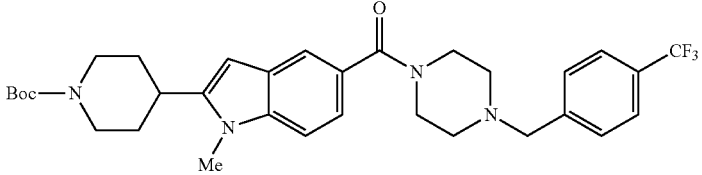 [SMILES: Cn1c(C2CCN(C(=O)OC(C)(C)C)CC2)cc2cc(C(=O)N3CCN(Cc4ccc(C(F)(F)F)cc4)CC3)ccc21] | ESI+: 585 |

TABLE 10-continued

| Pre | Syn | Str | Dat |
|---|---|---|---|
| 29 | P29 | (Boc-N-piperidine-indole with Me, CO2Me, N-Me) | ESI+: 409 [M + Na]+ |
| 30 | P30 | (Boc-N-piperidine-indole-carbonyl-piperazine-CH2-C6H4-CF3, N-Me) | ESI+: 607 [M + Na]+ |
| 31 | P31 | (2-F, 4-CF3-benzyl piperazine-Boc) | APCI/ESI+: 363 |
| 32 | P32 | (Me-piperazine-CH2-C6H4-CF3, ×HCl) | ESI+: 259 |
| 33 | P33 | (Boc-N-piperidine-benzimidazole-carbonyl-piperazine-CH2-C6H4-CN) | APCI/ESI−: 527 |

TABLE 11

| Pre | Syn | Str | Dat |
|---|---|---|---|
| 34 | P34 | (MeO2C-benzimidazole-piperidine-N-Boc) | ESI+: 360 |
| 35 | P35 | (Br, F-benzimidazole-2-CO2H) | ESI+: 259, 261 |
| 36 | P36 | (Br-imidazo[4,5-b]pyridine-2-CCl3) | ESI+: 314, 316, 318 |

TABLE 11-continued

| Pre | Syn | Str | Dat |
|---|---|---|---|
| 37 | P37 | ![5-bromo-1-methyl-benzimidazole-2-carboxylic acid methyl ester] | APCI/ESI+: 269 |
| 38 | P38 | ![5-bromo-3-methyl-1H-indole-2-carboxylic acid] | ESI+: 268, 270 |
| 39 | P39 | ![2-(1-Boc-piperidin-4-yl)-1H-indole-5-carboxylic acid methyl ester] | ESI−: 357 |
| 40 | P40 | ![4-(difluoromethyl)benzyl chloride] | CI+: 176 [M]+ |
| 41 | P1 | ![1-(1-Boc-piperidin-4-yl)-5-[4-(4-trifluoromethylbenzyl)piperazine-1-carbonyl]-1H-indole] | ESI+: 571 |

TABLE 12

| Pre | Syn | Str | Dat |
|---|---|---|---|
| 42 | P25 | ![2-(1-Boc-piperidin-4-yl)-1H-benzimidazole-5-carboxylic acid] | ESI+: 346 |
| 43 | P1 | ![2-(1-Boc-piperidin-4-yl)-5-[4-(4-trifluoromethylbenzyl)piperazine-1-carbonyl]-1H-benzimidazole] | ESI+: 572 |
| 44 | P21 | ![2-(piperidin-4-yl)-5-[4-(4-trifluoromethylbenzyl)piperazine-1-carbonyl]-1H-benzimidazole] | ESI+: 472 |
| 45 | P25 | ![2-(4-Boc-piperazin-1-yl)-1H-benzimidazole-5-carboxylic acid] | ESI+: 347 |

TABLE 12-continued

| Pre | Syn | Str | Dat |
|---|---|---|---|
| 46 | P1 | Boc-N(piperazine)-N-(2-benzimidazolyl)-C(=O)-N(piperazine)-N-CH2-C6H4-CF3 | ESI+: 573 |
| 47 | P21 | HN(piperazine)-N-(2-benzimidazolyl)-C(=O)-N(piperazine)-N-CH2-C6H4-CF3 | APCI/ESI+: 473 |
| 48 | P25 | Boc-N(piperidine)-(2-indolyl)-5-CO2H | ESI-: 343 |
| 49 | P21 | HN(piperidine)-(2-indolyl)-5-C(=O)-N(piperazine)-N-CH2-C6H4-CF3 | ESI+: 471 |

TABLE 13

| Pre | Syn | Str | Dat |
|---|---|---|---|
| 50 | P1 | Boc-N(piperidine)-(2-indolyl)-5-C(=O)-N(piperazine)-N-CH2-C6H4-CF3 | ESI+: 571 |
| 51 | P21 | HN(piperidine)-(2-indolyl, N-Me)-5-C(=O)-N(piperazine)-N-CH2-C6H4-CF3 | APCI/ESI+: 485 |
| 52 | P23 | HN(piperazine)-N-CH2-C6H3(2-F)(4-CF3) · xHCl | ESI+: 263 |
| 53 | P1 | 5-Br-6-F-benzimidazole-2-C(=O)-N(piperazine)-N-CH2-C6H4-CF3 | ESI-: 483, 485 |

TABLE 13-continued
| Pre | Syn | Str | Dat |
|---|---|---|---|
| 54 | P1 | 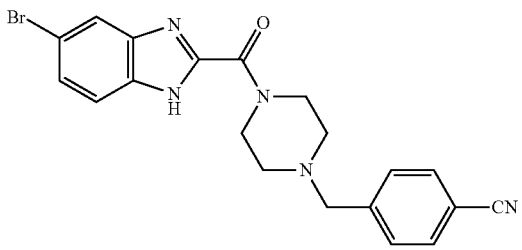 [SMILES: N#Cc1ccc(CN2CCN(C(=O)c3nc4cc(Br)ccc4[nH]3)CC2)cc1] | ESI+: 424, 426 |
| 55 | P1 | 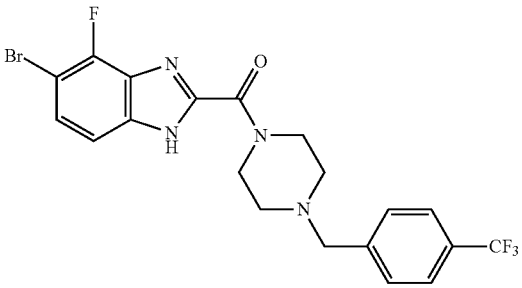 [SMILES: O=C(c1nc2c(F)c(Br)ccc2[nH]1)N1CCN(Cc2ccc(C(F)(F)F)cc2)CC1] | ESI+: 485, 487 |
TABLE 14
| Pre | Syn | Str | Dat |
|---|---|---|---|
| 56 | P1 | 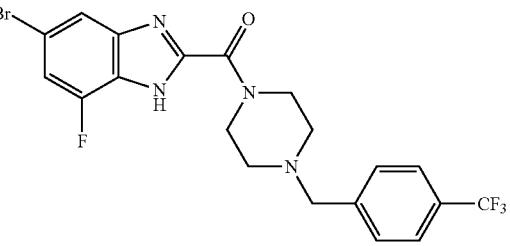 | ESI+: 485, 487 |
| 57 | P35 | 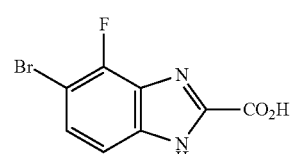 | ESI+: 259, 261 |
| 58 | P35 | 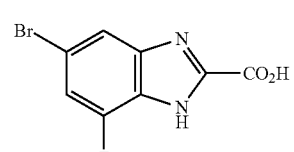 | ESI+: 259, 261 |
| 59 | P9 | 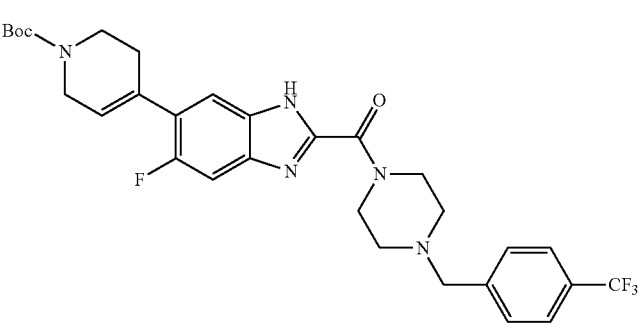 [SMILES: CC(C)(C)OC(=O)N1CC=C(c2cc3[nH]c(C(=O)N4CCN(Cc5ccc(C(F)(F)F)cc5)CC4)nc3cc2F)CC1] | ESI+: 588 |

TABLE 14-continued

| Pre | Syn | Str | Dat |
|---|---|---|---|
| 60 | P1 | 5-bromo-1H-benzimidazol-2-yl with piperazine-N-CH2-(4-CHF2-phenyl) | APCI/ESI+: 449, 451 |
| 61 | P9 | Boc-tetrahydropyridinyl-benzimidazole-2-carbonyl-piperazine-CH2-(4-CN-phenyl) | APCI/ESI+: 527 |

TABLE 15

| Pre | Syn | Str | Dat |
|---|---|---|---|
| 62 | P9 | Boc-tetrahydropyridinyl-benzimidazole-2-carbonyl-piperazine-CH2-(4-CHF2-phenyl) | APCI/ESI+: 552 |
| 63 | P17 | Boc-piperidinyl-benzimidazole-2-carbonyl-piperazine-CH2-(4-CHF2-phenyl) | APCI/ESI−: 552 |

TABLE 15-continued

| Pre | Syn | Str | Dat |
|---|---|---|---|
| 64 | P21 | (structure) | APCI/ESI+: 470 |
| 65 | P65 | (structure) | APCI/ESI+: 472 |
| 66 | P21 | (structure) | APCI/ESI+: 454 |

TABLE 16

| Pre | Syn | Str | Dat |
|---|---|---|---|
| 67 | P21 | (structure) | APCI/ESI+: 429 |

TABLE 16-continued
| Pre | Syn | Str | Dat |
|---|---|---|---|
| 68 | P9 | 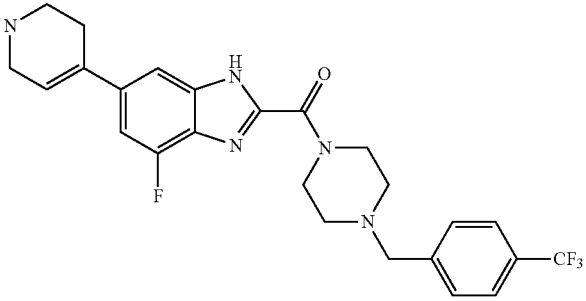 | APCI/ESI+: 588 |
| 69 | P9 | 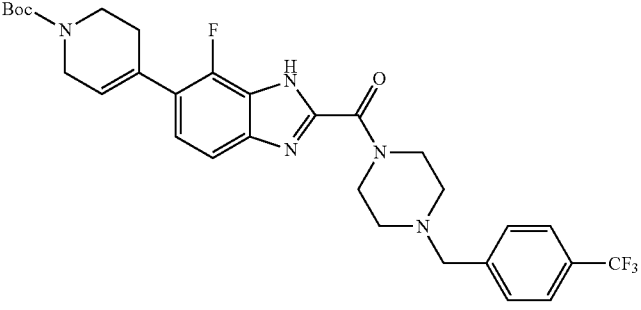 [SMILES: CC(C)(C)OC(=O)N1CC=C(c2ccc3nc(C(=O)N4CCN(Cc5ccc(C(F)(F)F)cc5)CC4)[nH]c3c2F)CC1] | APCI/ESI+: 588 |
| 70 | P9 | 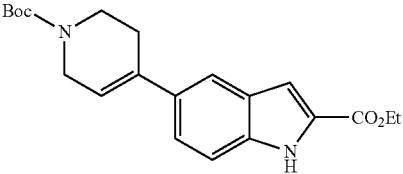 [SMILES: CCOC(=O)c1cc2cc(C3=CCN(C(=O)OC(C)(C)C)CC3)ccc2[nH]1] | ESI−: 369 |
| 71 | P17 | 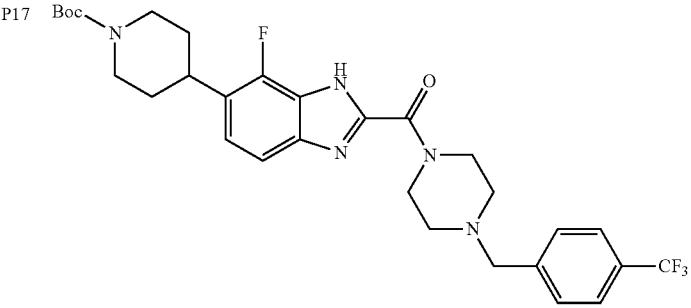 | APCI/ESI−: 588 |
TABLE 17
| Pre | Syn | Str | Dat |
|---|---|---|---|
| 72 | P17 | 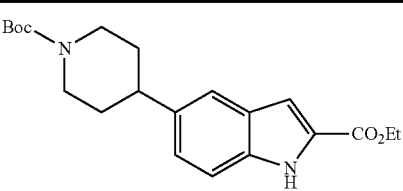 | ESI+: 395 [M + Na]+ |

TABLE 17-continued

| Pre | Syn | Str | Dat |
|---|---|---|---|
| 73 | P25 | [structure] | ESI−: 343 |
| 74 | P17 | [structure] | APCI/ESI−: 588 |
| 75 | P9 | [structure] | ESI−: 369 |
| 76 | P1 | [structure] | ESI+: 571 |

TABLE 18

| Pre | Syn | Str | Dat |
|---|---|---|---|
| 77 | P21 | [structure] | APCI/ESI+: 471 |

TABLE 18-continued

| Pre | Syn | Str | Dat |
|---|---|---|---|
| 78 | P21 | (structure) | APCI/ESI+: 490 |
| 79 | P1 | (structure) | ESI+: 466, 468 |
| 80 | P1 | (structure) | APCI/ESI+: 424 |
| 81 | P9 | (structure) | APCI/ESI+: 571 |

TABLE 19

| Pre | Syn | Str | Dat |
|---|---|---|---|
| 82 | P9 | (structure) | ESI+: 569 |

TABLE 19-continued
| Pre | Syn | Str | Dat |
|---|---|---|---|
| 83 | P21 | 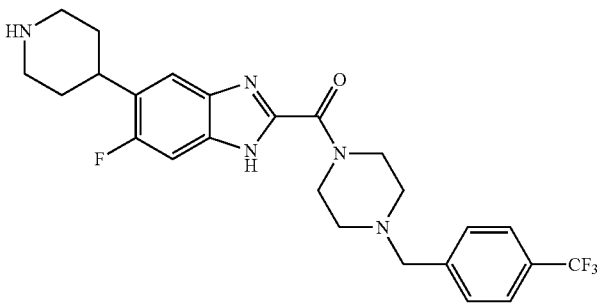 [SMILES: O=C(c1nc2cc(C3CCNCC3)c(F)cc2[nH]1)N1CCN(Cc2ccc(C(F)(F)F)cc2)CC1] | APCI/ESI+: 490 |
| 84 | P9 | 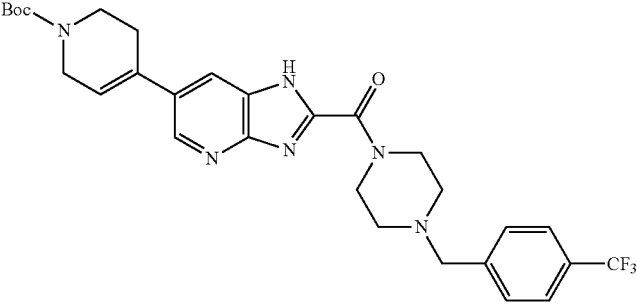 [SMILES: CC(C)(C)OC(=O)N1CC=C(c2cnc3nc(C(=O)N4CCN(Cc5ccc(C(F)(F)F)cc5)CC4)[nH]c3c2)CC1] | APCI/ESI+: 571 |
| 85 | P17 | 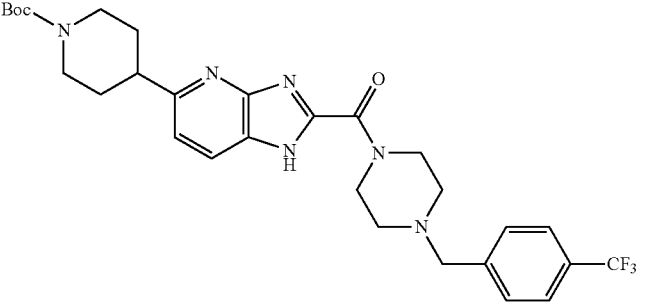 [SMILES: CC(C)(C)OC(=O)N1CCC(c2ccc3[nH]c(C(=O)N4CCN(Cc5ccc(C(F)(F)F)cc5)CC4)nc3n2)CC1] | ESI+: 573 |
| 86 | P21 | 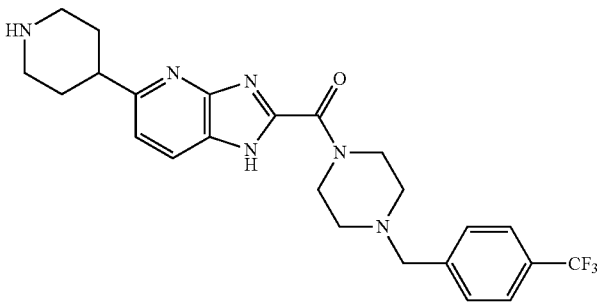 [SMILES: O=C(c1nc2nc(C3CCNCC3)ccc2[nH]1)N1CCN(Cc2ccc(C(F)(F)F)cc2)CC1] | APCI/ESI+: 473 |

TABLE 20

| Pre | Syn | Str | Dat |
|-----|-----|-----|-----|
| 87 | P21 | | APCI/ESI+: 473 |
| 88 | P21 | | ESI+: 471 |
| 89 | P21 | | ESI+: 490 |
| 90 | P25 | | ESI−: 357 |
| 91 | P1 | | ESI+: 467, 469 |

TABLE 21
| Pre | Syn | Str | Dat |
|---|---|---|---|
| 92 | P92 | 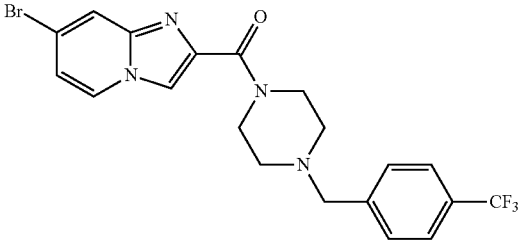 [SMILES: O=C(c1cn2ccc(Br)cc2n1)N1CCN(Cc2ccc(C(F)(F)F)cc2)CC1] | ESI+: 467, 469 |
| 93 | P1 | 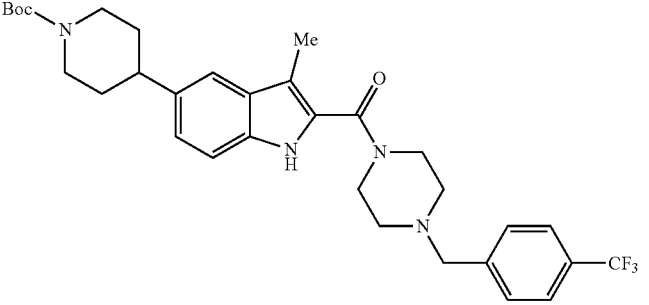 [SMILES: Cc1c(C(=O)N2CCN(Cc3ccc(C(F)(F)F)cc3)CC2)[nH]c2ccc(C3CCN(C(=O)OC(C)(C)C)CC3)cc12] | ESI+: 585 |
| 94 | P21 | 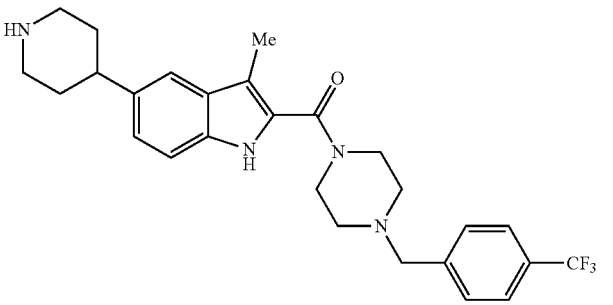 [SMILES: Cc1c(C(=O)N2CCN(Cc3ccc(C(F)(F)F)cc3)CC2)[nH]c2ccc(C3CCNCC3)cc12] | ESI+: 485 |
| 95 | P9 | 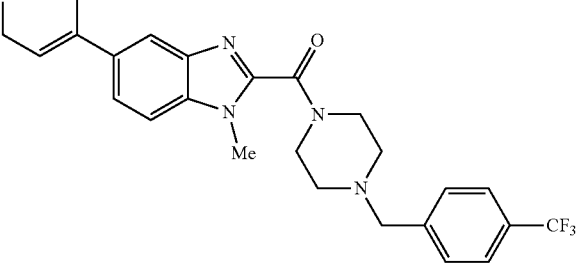 | APCI/ESI+: 584 |
| 96 | P21 | 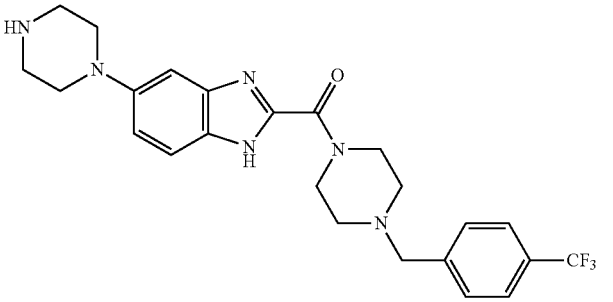 [SMILES: O=C(c1nc2cc(N3CCNCC3)ccc2[nH]1)N1CCN(Cc2ccc(C(F)(F)F)cc2)CC1] | APCI/ESI+: 473 |

TABLE 22
| Pre | Syn | Str | Dat |
|---|---|---|---|
| 97 | P17 | 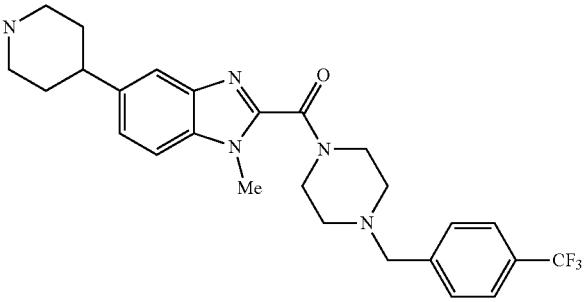 | APCI/ESI+: 586 |
| 98 | P21 | 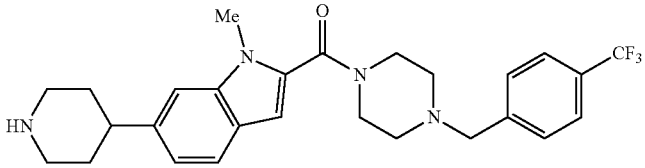 [SMILES: Cn1c(C(=O)N2CCN(Cc3ccc(C(F)(F)F)cc3)CC2)cc2ccc(C3CCNCC3)cc21] | ESI+: 485 |
| 99 | P9 | 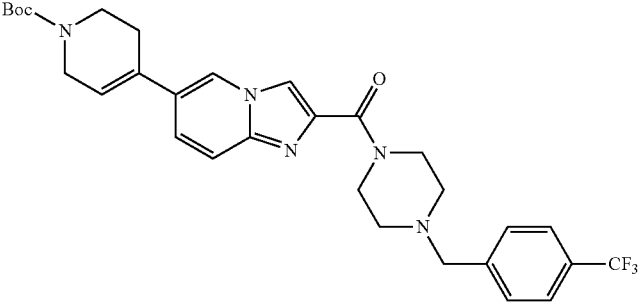 [SMILES: CC(C)(C)OC(=O)N1CC=C(c2ccc3nc(C(=O)N4CCN(Cc5ccc(C(F)(F)F)cc5)CC4)cn3c2)CC1] | ESI+: 570 |
| 100 | P100 | 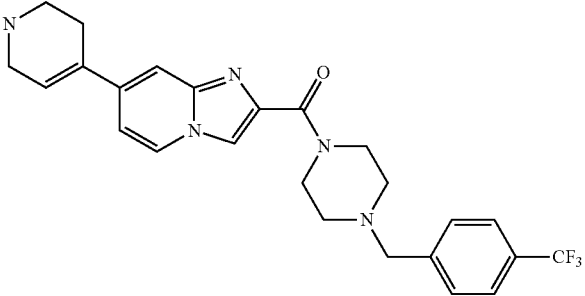 | ESI+: 570 |
| 101 | P29 | 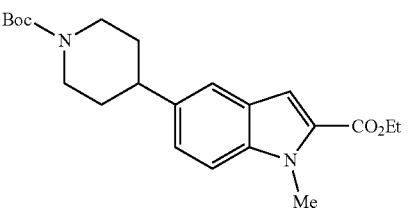 [SMILES: CCOC(=O)c1cc2cc(C3CCN(C(=O)OC(C)(C)C)CC3)ccc2n1C] | ESI+: 409 [M + Na]+ |

TABLE 23

| Pre | Syn | Str | Dat |
|-----|-----|-----|-----|
| 102 | P25 | Boc-piperidine-4-yl-1-methyl-1H-indole-2-carboxylic acid | APCI/ESI-: 357 |
| 103 | P21 | 5-(piperidin-4-yl)-1-methyl-benzimidazole-2-yl-[4-(4-trifluoromethylbenzyl)piperazin-1-yl]methanone | ESI+: 486 |
| 104 | P21 | 5-(piperidin-4-yl)-1,3-dimethyl-indole-2-yl-[4-(4-trifluoromethylbenzyl)piperazin-1-yl]methanone | APCI/ESI+: 499 |
| 105 | P21 | 5-(piperidin-4-yl)-1-methyl-indole-2-yl-[4-(4-trifluoromethylbenzyl)piperazin-1-yl]methanone | ESI+: 485 |
| 106 | P21 | 6-(piperidin-4-yl)-imidazo[1,2-a]pyridin-2-yl-[4-(4-trifluoromethylbenzyl)piperazin-1-yl]methanone | ESI+: 472 |

TABLE 24
| Pre | Syn | Str | Dat |
|---|---|---|---|
| 107 | P107 | 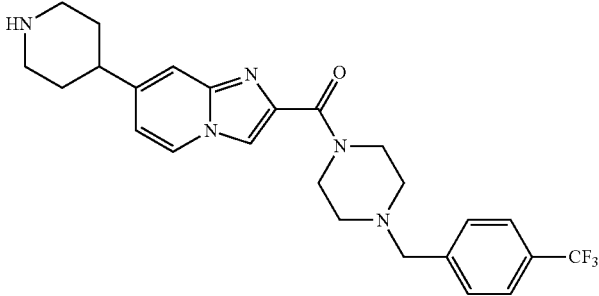 [SMILES: O=C(c1cn2ccc(C3CCNCC3)cc2n1)N1CCN(Cc2ccc(C(F)(F)F)cc2)CC1] | ESI+: 472 |
| 108 | P17 | 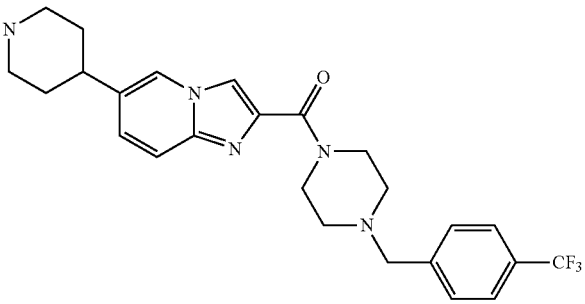 | ESI+: 572 |
| 109 | P109 | 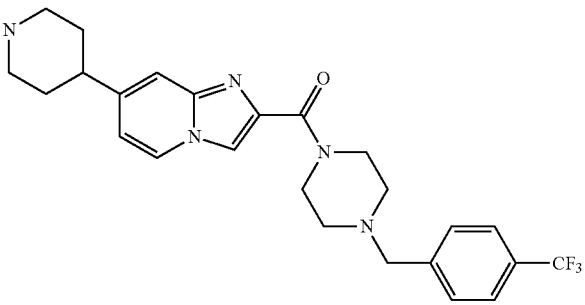 | ESI+: 572 |
| 110 | P25 | 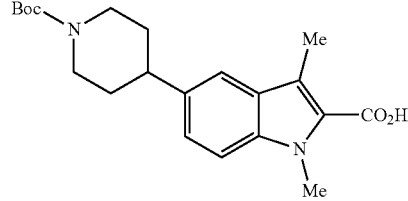 [SMILES: Cc1c(C(=O)O)n(C)c2ccc(C3CCN(C(=O)OC(C)(C)C)CC3)cc12] | ESI−: 371 |
| 111 | P4 | 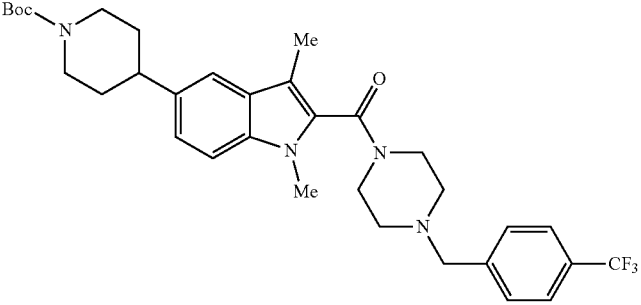 [SMILES: Cc1c(C(=O)N2CCN(Cc3ccc(C(F)(F)F)cc3)CC2)n(C)c2ccc(C3CCN(C(=O)OC(C)(C)C)CC3)cc12] | ESI+: 599 |

TABLE 25

| Pre | Syn | Str | Dat |
|-----|-----|-----|-----|
| 112 | P1 | 6-bromo-benzoxazol-2-yl carbonyl piperazine benzyl-4-CF3 | ESI+: 468, 470 |
| 113 | P1 | 5-bromo-benzoxazol-2-yl carbonyl piperazine benzyl-4-CF3 | ESI+: 468, 470 |
| 114 | P36 | 5-bromo-2-(trichloromethyl)-1H-benzimidazole | ESI+: 313, 315, 317 |
| 115 | P9 | Boc-tetrahydropyridinyl-benzoxazol-2-yl carbonyl piperazine benzyl-4-CF3 | ESI+: 571 |
| 116 | P9 | Boc-tetrahydropyridinyl-benzoxazol-2-yl carbonyl piperazine benzyl-4-CF3 | ESI+: 571 |

TABLE 26

| Pre | Syn | Str | Dat |
|-----|-----|-----|-----|
| 117 | P17 | | ESI+: 595 [M + Na]+ |
| 118 | P1 | | ESI+: 485, 487 |
| 119 | P1 | | ESI+: 479, 481 |
| 120 | P36 | | ESI+: 327, 329, 331 |
| 121 | P21 | | APCI/ESI+: 490 |

TABLE 27

| Pre | Syn | Str | Dat |
|---|---|---|---|
| 122 | P21 | | ESI+: 484 |
| 123 | P1 | | ESI+: 423, 425 |
| 124 | P9 | | ESI+: 584 |
| 125 | P9 | | ESI+: 588 |
| 126 | P9 | | ESI+: 582 |

TABLE 28
| Pre | Syn | Str | Dat |
|---|---|---|---|
| 127 | P17 | 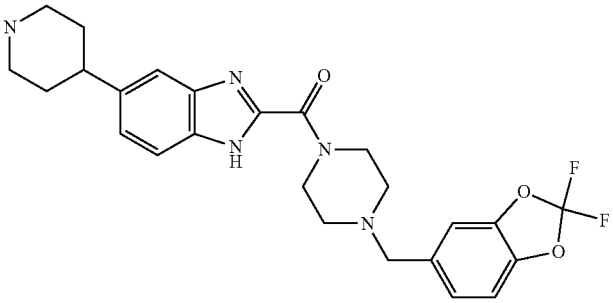 | APCI/ESI−: 582 |
| 128 | P17 | 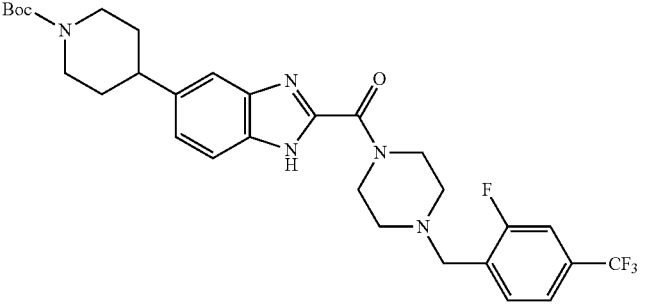 [SMILES: CC(C)(C)OC(=O)N1CCC(c2ccc3[nH]c(C(=O)N4CCN(Cc5ccc(C(F)(F)F)cc5F)CC4)nc3c2)CC1] | ESI+: 590 |
| 129 | P4 | 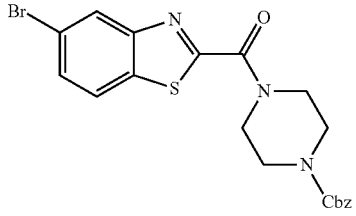 [SMILES: O=C(OCc1ccccc1)N1CCN(C(=O)c2nc3cc(Br)ccc3s2)CC1] | APCI/ESI+: 460, 462 |
| 130 | P4 | 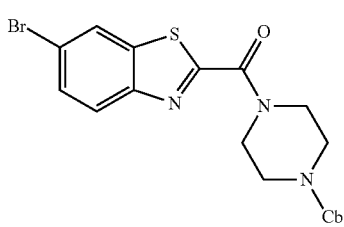 | APCI/ESI+: 460, 462 |
| 131 | P30 | 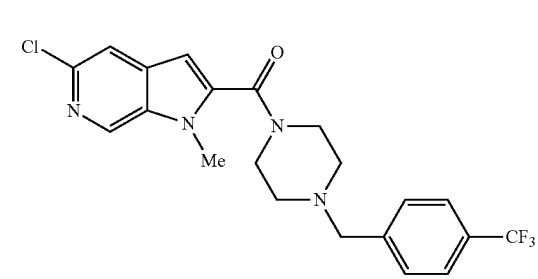 [SMILES: Cn1c(C(=O)N2CCN(Cc3ccc(C(F)(F)F)cc3)CC2)cc2cc(Cl)ncc21] | APCI/ESI+: 437 |

TABLE 29
| Pre | Syn | Str | Dat |
|---|---|---|---|
| 132 | P12 | 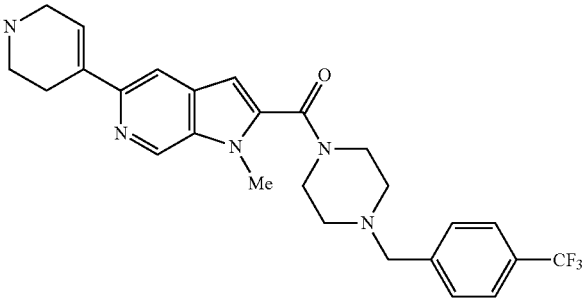 | ESI+: 584 |
| 133 | P17 | 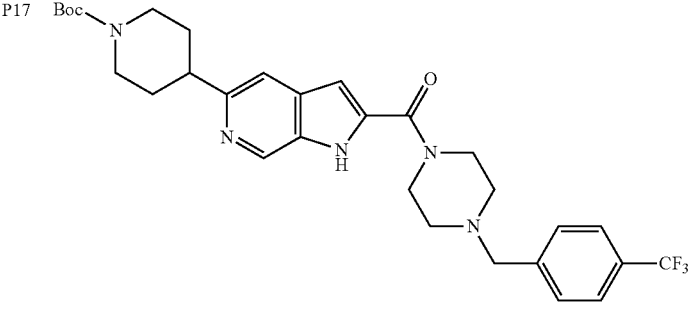 | ESI+: 572 |
| 134 | P3 | 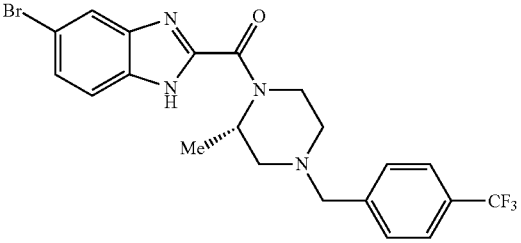 [SMILES: C[C@H]1CN(Cc2ccc(C(F)(F)F)cc2)CCN1C(=O)c1nc2cc(Br)ccc2[nH]1] | ESI+: 481, 483 |
| 135 | P9 | 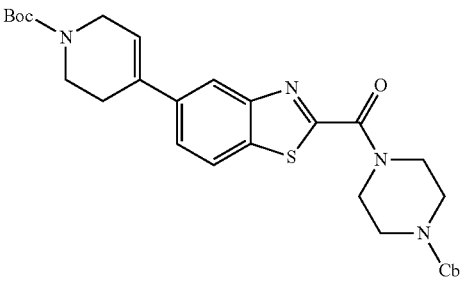 | APCI/ESI+: 563 |
| 136 | P9 | 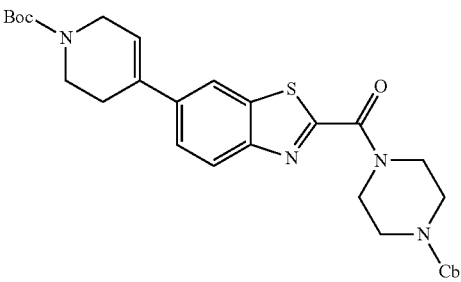 | APCI/ESI+: 563 |

TABLE 30
| Pre | Syn | Str | Dat |
|---|---|---|---|
| 137 | P9 | 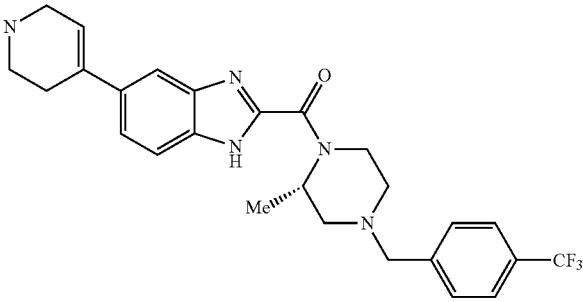 | ESI+: 584 |
| 138 | P17 | 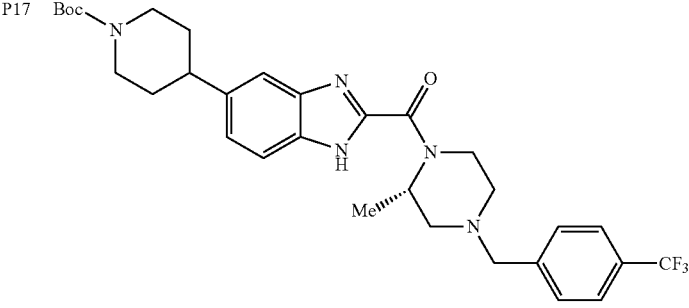 | ESI+: 586 |
| 139 | P1 | 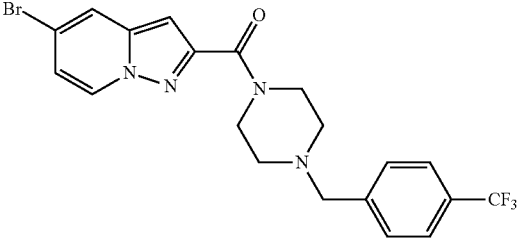 [SMILES: O=C(c1cc2cc(Br)ccn2n1)N1CCN(Cc2ccc(C(F)(F)F)cc2)CC1] | ESI+: 467, 469 |
| 140 | P9 | 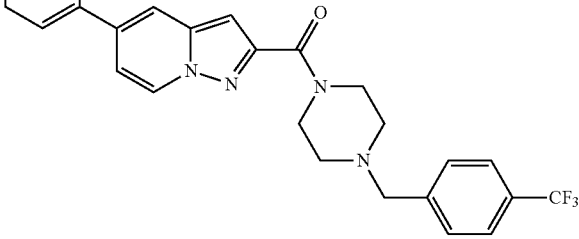 | ESI+: 570 |
| 141 | P16 | 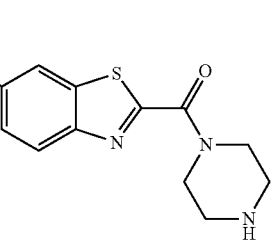 | ESI+: 431 |

TABLE 31
| Pre | Syn | Str | Dat |
|---|---|---|---|
| 142 | P21 | 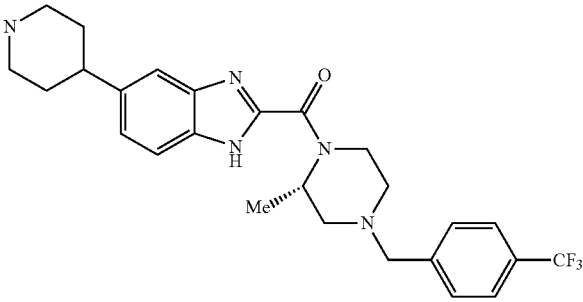 | ESI+: 486 |
| 143 | P33 | 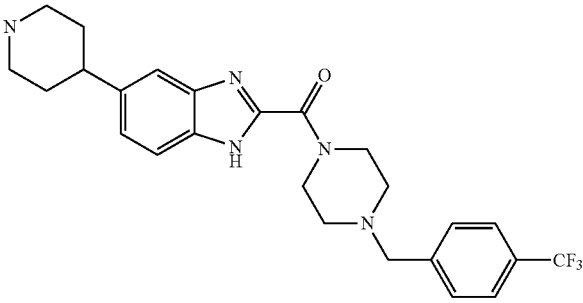 | ESI+: 589 |
| 144 | P33 | 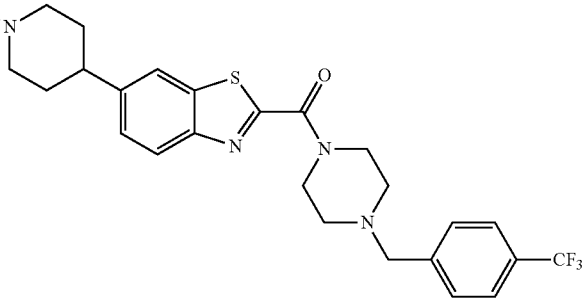 | APCI/ESI+: 589 |
| 145 | P21 | 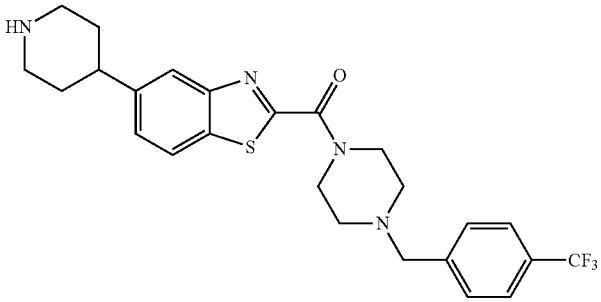 | ESI+: 489 |
| 146 | P21 | 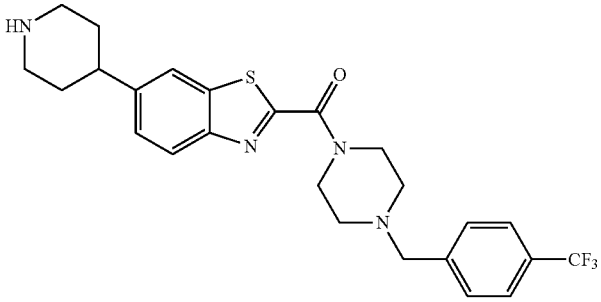 [SMILES: O=C(c1nc2ccc(C3CCNCC3)cc2s1)N1CCN(Cc2ccc(C(F)(F)F)cc2)CC1] | ESI+: 489 |

TABLE 32

| Pre | Syn | Str | Dat |
|-----|-----|-----|-----|
| 147 | P17 | | ESI+: 595 [M + Na]+ |
| 148 | P21 | | APCI/ESI+: 473 |
| 149 | P21 | | APCI/ESI+: 473 |
| 150 | P21 | | APCI/ESI+: 472 |
| 151 | P15 | | ESI+: 572 |

TABLE 33

| Pre | Syn | Str | Dat |
|---|---|---|---|
| 152 | P17 | Boc-piperidine-pyrrolo[2,3-c]pyridine(N-Me)-C(O)-piperazine-CH2-C6H4-CF3 | ESI+: 586 |
| 153 | P21 | HN-piperidine-pyrrolo[2,3-c]pyridine(N-Me)-C(O)-piperazine-CH2-C6H4-CF3 | ESI+: 486 |
| 154 | P4 | Boc-piperidine-indole(N-Me)-C(O)-piperazine-CH2-C6H4-CHF2 | ESI+: 567 |
| 155 | P21 | HN-piperidine-indole(N-Me)-C(O)-piperazine-CH2-C6H4-CHF2 | ESI+: 467 |
| 156 | P4 | Boc-piperidine-indole(N-Me)-C(O)-piperazine-CH2-C6H4-CN | ESI+: 542 |

TABLE 34
| Pre | Syn | Str | Dat |
|---|---|---|---|
| 157 | P21 | 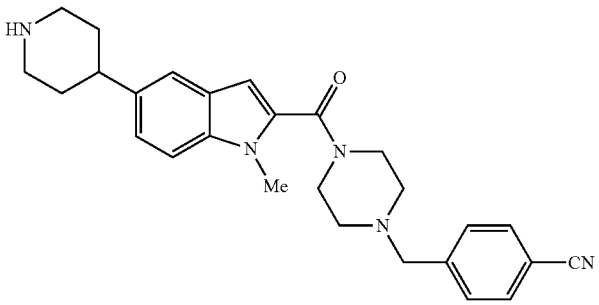 [SMILES: Cn1c(C(=O)N2CCN(Cc3ccc(C#N)cc3)CC2)cc2cc(C3CCNCC3)ccc21] | ESI+: 442 |
| 158 | P21 | 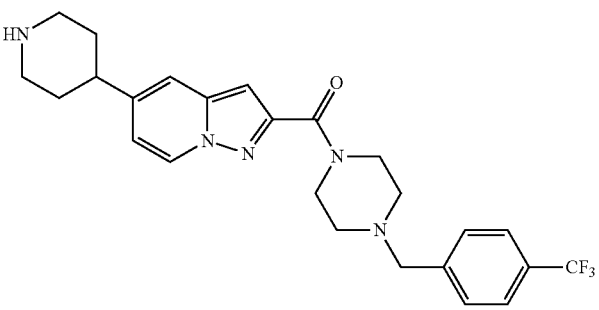 [SMILES: O=C(c1cc2cc(C3CCNCC3)ccn2n1)N1CCN(Cc2ccc(C(F)(F)F)cc2)CC1] | ESI+: 472 |
| 159 | P25 | 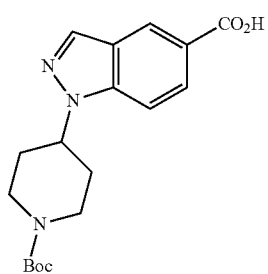 [SMILES: CC(C)(C)OC(=O)N1CCC(n2ncc3cc(C(=O)O)ccc32)CC1] | ESI−: 344 |
| 160 | P25 | 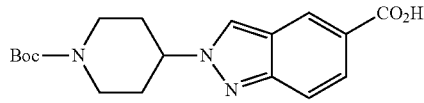 [SMILES: CC(C)(C)OC(=O)N1CCC(n2cc3cc(C(=O)O)ccc3n2)CC1] | ESI−: 344 |
| 161 | P1 | 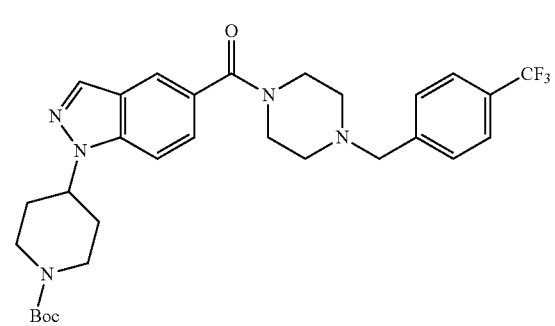 [SMILES: CC(C)(C)OC(=O)N1CCC(n2ncc3cc(C(=O)N4CCN(Cc5ccc(C(F)(F)F)cc5)CC4)ccc32)CC1] | ESI+: 572 |
TABLE 35
| Pre | Syn | Str | Dat |
|---|---|---|---|
| 162 | P1 | 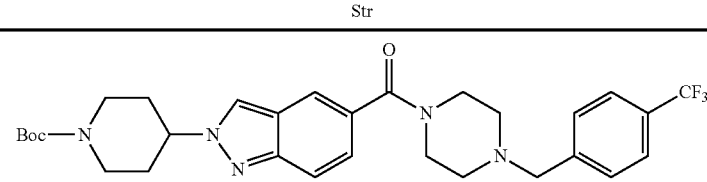 | ESI+: 572 |

TABLE 35-continued

| Pre | Syn | Str | Dat |
|---|---|---|---|
| 163 | P17 | | APCI/ESI+: 586 |
| 164 | P21 | | APCI/ESI+: 486 |
| 165 | P165 | | ESI+: 155 |
| 166 | P166 | | ESI+: 173, 175 |
| 167 | P167 | | ESI+: 435 |

TABLE 36

| Pre | Syn | Str | Dat |
|---|---|---|---|
| 168 | P168 | | ESI+: 344 |

TABLE 36-continued

| Pre | Syn | Str | Dat |
|---|---|---|---|
| 169 | P169 | | ESI−: 411 |
| 170 | P170 | | ESI+: 243 |
| 171 | P171 | | ESI+: 531 |
| 172 | P1 | | ESI+: 508 |

TABLE 37

| Pre | Syn | Str | Dat |
|---|---|---|---|
| 173 | P15 | | ESI+: 510 |

TABLE 37-continued

| Pre | Syn | Str | Dat |
|---|---|---|---|
| 174 | P20 | (structure) HCl | ESI+: 410 |
| 175 | P166 | (structure) | ESI+: 157, 159 |
| 176 | P1 | (structure) | ESI+: 423, 425 |
| 177 | P1 | (structure) | ESI+: 442, 444 |

TABLE 38

| Pre | Syn | Str | Dat |
|---|---|---|---|
| 178 | P9 | (structure) | ESI+: 545 |
| 179 | P169 | (structure) | ESI+: 432 |

TABLE 38-continued

| Pre | Syn | Str | Dat |
|---|---|---|---|
| 180 | P9 | (structure) | ESI+: 526 |
| 181 | P33 | (structure) | ESI+: 547 |
| 182 | P21 | (structure) | ESI+: 447 |

TABLE 39

| Pre | Syn | Str | Dat |
|---|---|---|---|
| 183 | P33 | (structure) | ESI−: 526 |
| 184 | P30 | (structure) | ESI+: 542 |
| 185 | P21 | (structure) | ESI+: 442 |
| 186 | P165 | (structure) | ESI+: 139 |

TABLE 40
| Ex | Str |
|---|---|
| 1 | 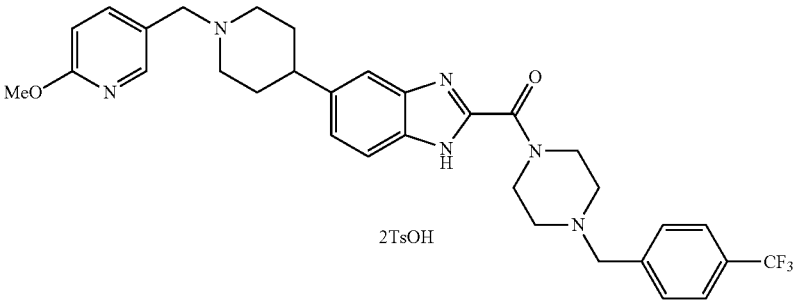 [SMILES: COc1ccc(CN2CCC(c3ccc4[nH]c(C(=O)N5CCN(Cc6ccc(C(F)(F)F)cc6)CC5)nc4c3)CC2)cn1] 2TsOH |
| 2 | 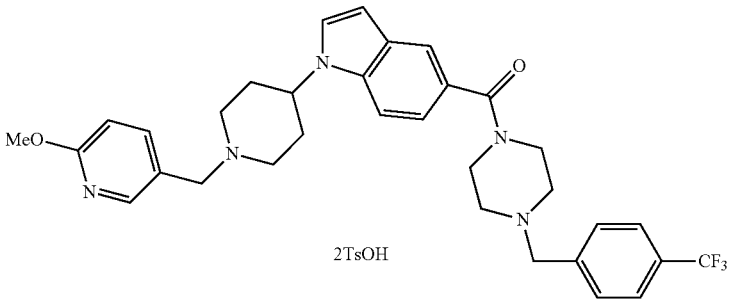 [SMILES: COc1ccc(CN2CCC(n3ccc4cc(C(=O)N5CCN(Cc6ccc(C(F)(F)F)cc6)CC5)ccc43)CC2)cn1] 2TsOH |
| 3 | 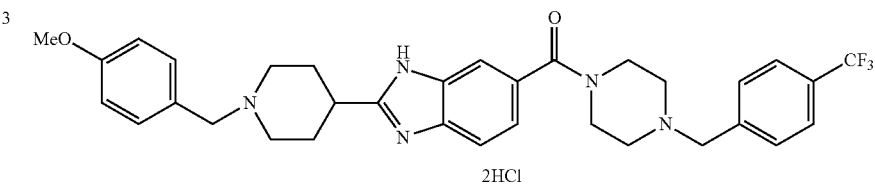 2HCl |
| 4 | 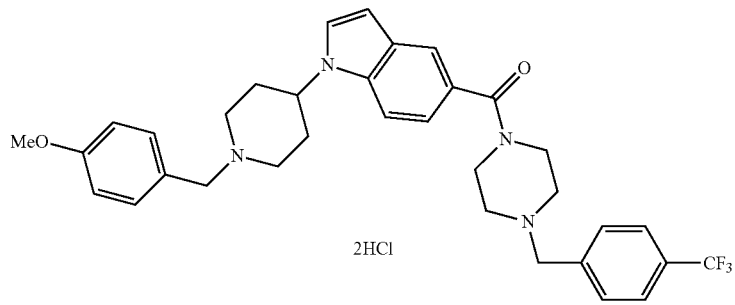 [SMILES: COc1ccc(CN2CCC(n3ccc4cc(C(=O)N5CCN(Cc6ccc(C(F)(F)F)cc6)CC5)ccc43)CC2)cc1] 2HCl |
| 5 | 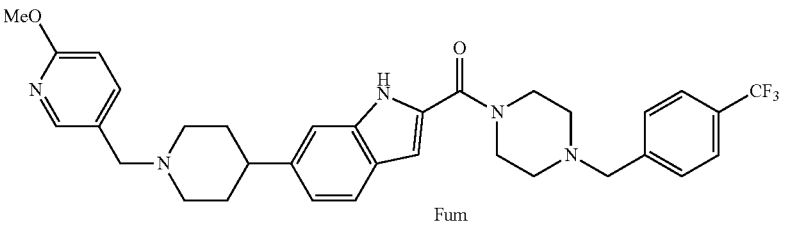 [SMILES: COc1ccc(CN2CCC(c3ccc4cc(C(=O)N5CCN(Cc6ccc(C(F)(F)F)cc6)CC5)[nH]c4c3)CC2)cn1] Fum |

TABLE 41

| Ex | Str |
|---|---|
| 6 | (structure: 6-methoxypyridin-3-ylmethyl-piperidinyl-benzothiazole-2-carbonyl-piperazinyl-4-(trifluoromethyl)benzyl) |
| 7 | (structure: 5-methoxypyrazin-2-ylmethyl-piperidinyl-1H-benzimidazole-2-carbonyl-piperazinyl-4-(trifluoromethyl)benzyl) · 2TsOH |
| 8 | (structure: 5-methoxypyrazin-2-ylmethyl-piperidinyl-1H-benzimidazole-2-carbonyl-piperazinyl-4-(trifluoromethyl)benzyl) · 3HCl |
| 9 | (structure: 6-methoxypyridin-3-ylmethyl-piperidinyl-1H-benzimidazol-2-yl with 5-carbonyl-piperazinyl-4-(trifluoromethyl)benzyl) · 3TsOH |
| 10 | (structure: 6-methoxypyridin-3-ylmethyl-piperazinyl-1H-benzimidazol-2-yl-5-carbonyl-piperazinyl-4-(trifluoromethyl)benzyl) · 2TsOH |
| 11 | (structure: 4-methoxybenzyl-piperazinyl-1H-benzimidazol-2-yl-5-carbonyl-piperazinyl-4-(trifluoromethyl)benzyl) · 3HCl |

TABLE 42
| Ex | Str |
|----|-----|
| 12 | 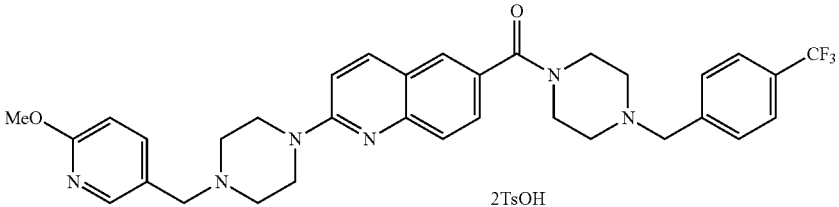 [SMILES: COc1ccc(CN2CCN(c3ccc4cc(C(=O)N5CCN(Cc6ccc(C(F)(F)F)cc6)CC5)ccc4n3)CC2)cn1] 2TsOH |
| 13 | 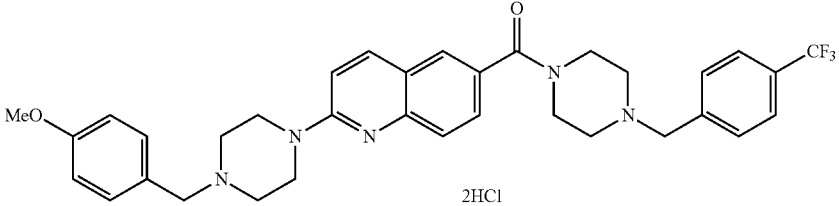 [SMILES: COc1ccc(CN2CCN(c3ccc4cc(C(=O)N5CCN(Cc6ccc(C(F)(F)F)cc6)CC5)ccc4n3)CC2)cc1] 2HCl |
| 14 | 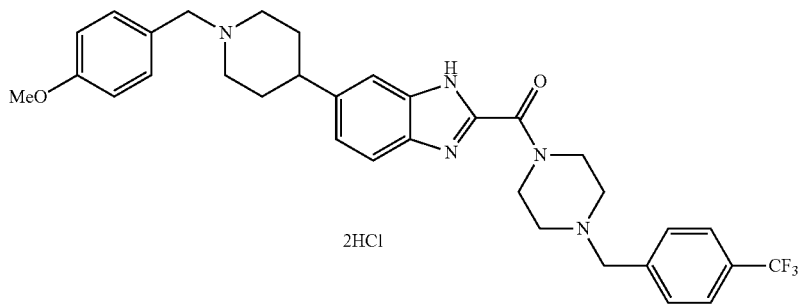 [SMILES: COc1ccc(CN2CCC(c3ccc4nc(C(=O)N5CCN(Cc6ccc(C(F)(F)F)cc6)CC5)[nH]c4c3)CC2)cc1] 2HCl |
| 15 | 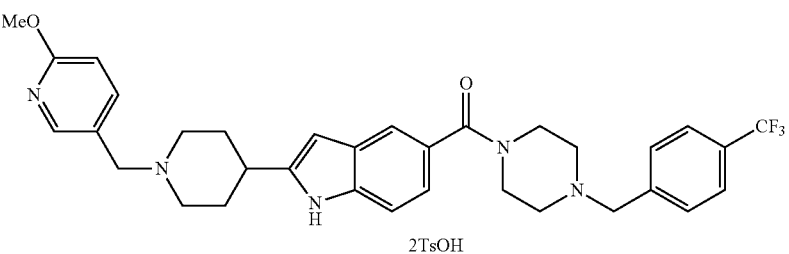 [SMILES: COc1ccc(CN2CCC(c3cc4cc(C(=O)N5CCN(Cc6ccc(C(F)(F)F)cc6)CC5)ccc4[nH]3)CC2)cn1] 2TsOH |
| 16 | 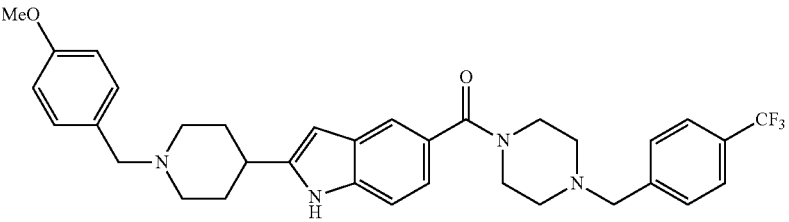 2HCl |

TABLE 43

| Ex | Str |
|---|---|
| 17 | (6-methoxypyridin-3-yl)methyl-piperidin-4-yl-1-methyl-1H-indole-5-carbonyl-piperazine-4-(trifluoromethyl)benzyl, 2TsOH |
| 18 | (6-methoxypyridin-3-yl)methyl-piperidin-4-yl-1-methyl-1H-benzimidazole-2-carbonyl-piperazine-4-(trifluoromethyl)benzyl, 2TsOH |
| 19 | (6-methoxypyridin-3-yl)methyl-piperidin-4-yl-1-methyl-1H-benzimidazole-2-carbonyl-piperazine-4-(trifluoromethyl)benzyl, 2TsOH |
| 20 | (6-methoxypyridin-3-yl)methyl-tetrahydropyridin-4-yl-1H-benzimidazole-2-carbonyl-piperazine-4-(trifluoromethyl)benzyl, 2TsOH |
| 21 | (6-methoxypyridin-3-yl)methyl-piperidin-4-yl-1H-benzimidazole-2-carbonyl-piperazine-4-(difluoromethyl)benzyl, 2TsOH |

TABLE 44

| Ex | Str |
|---|---|
| 22 | (structure; 3HCl) |
| 23 | (structure; 2TsOH) |
| 24 | (structure; 2TsOH) |
| 25 | (structure; 2TsOH) |
| 26 | (structure; 2TsOH) |

TABLE 45
| Ex | Str |
|---|---|
| 27 | 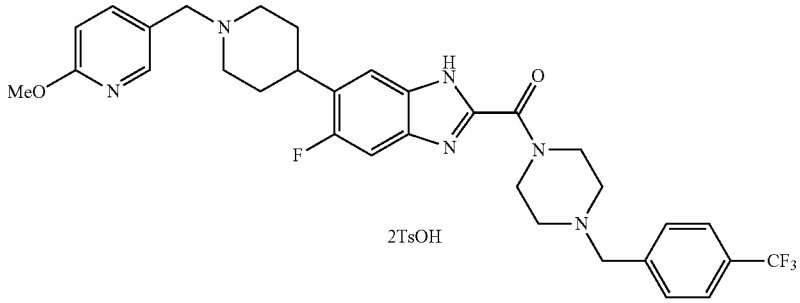 [SMILES: COc1ccc(CN2CCC(c3cc4[nH]c(C(=O)N5CCN(Cc6ccc(C(F)(F)F)cc6)CC5)nc4cc3F)CC2)cn1] 2TsOH |
| 28 | 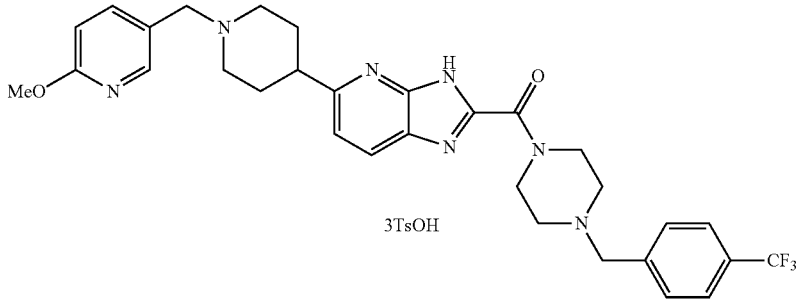 [SMILES: COc1ccc(CN2CCC(c3ccc4nc(C(=O)N5CCN(Cc6ccc(C(F)(F)F)cc6)CC5)[nH]c4n3)CC2)cn1] 3TsOH |
| 29 | 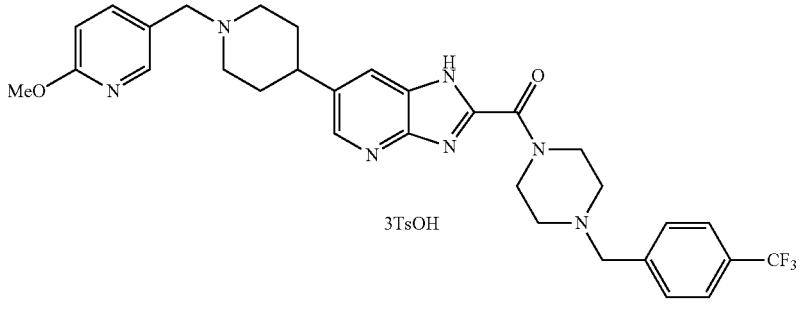 [SMILES: COc1ccc(CN2CCC(c3cnc4nc(C(=O)N5CCN(Cc6ccc(C(F)(F)F)cc6)CC5)[nH]c4c3)CC2)cn1] 3TsOH |
| 30 | 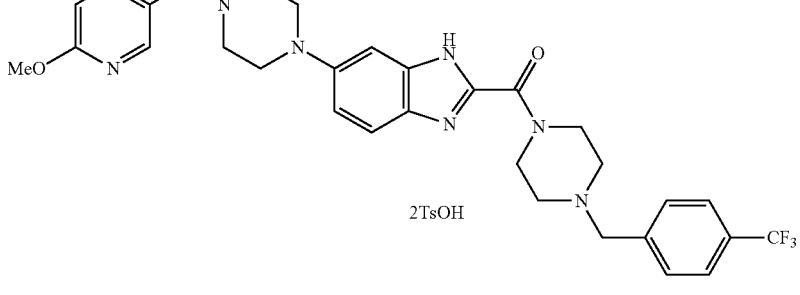 2TsOH |
| 31 | 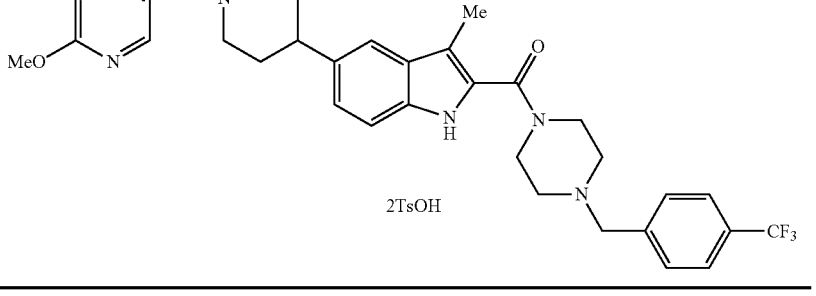 2TsOH |

TABLE 46
| Ex | Str |
|---|---|
| 32 | 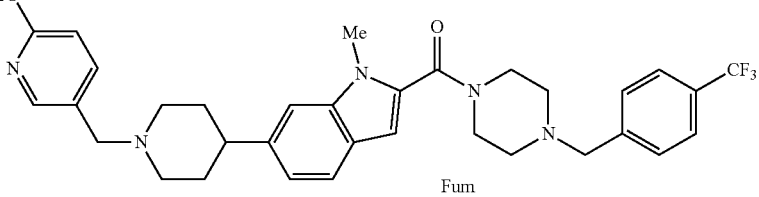 Fum |
| 33 | 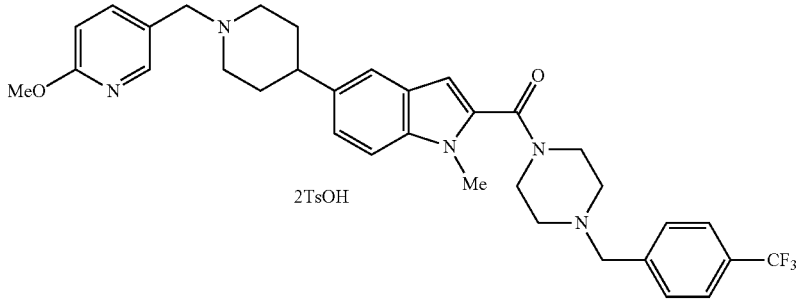 [SMILES: COc1ccc(CN2CCC(c3ccc4c(c3)cc(C(=O)N3CCN(Cc5ccc(C(F)(F)F)cc5)CC3)n4C)CC2)cn1] 2TsOH |
| 34 | 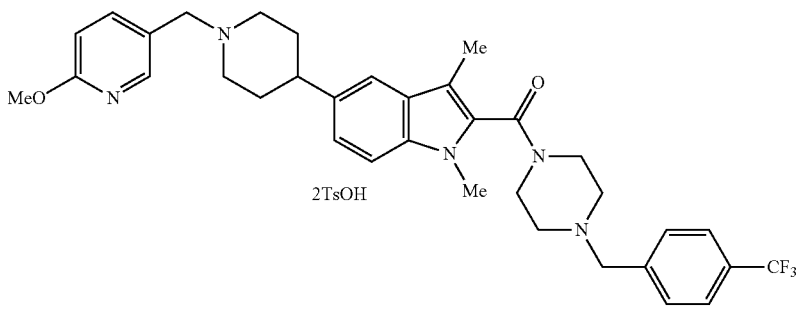 [SMILES: COc1ccc(CN2CCC(c3ccc4c(c3)c(C)c(C(=O)N3CCN(Cc5ccc(C(F)(F)F)cc5)CC3)n4C)CC2)cn1] 2TsOH |
| 35 | 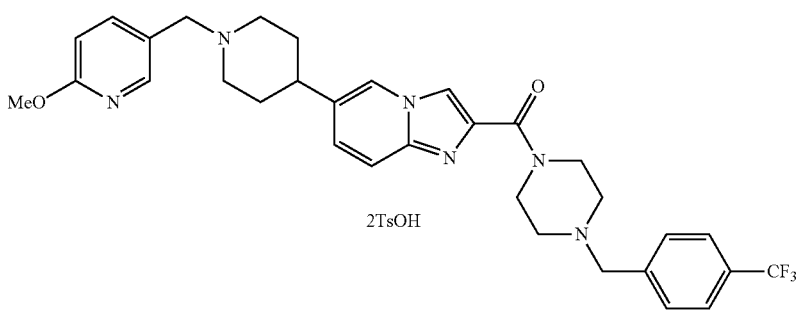 [SMILES: COc1ccc(CN2CCC(c3ccc4nc(C(=O)N5CCN(Cc6ccc(C(F)(F)F)cc6)CC5)cn4c3)CC2)cn1] 2TsOH |
| 36 | 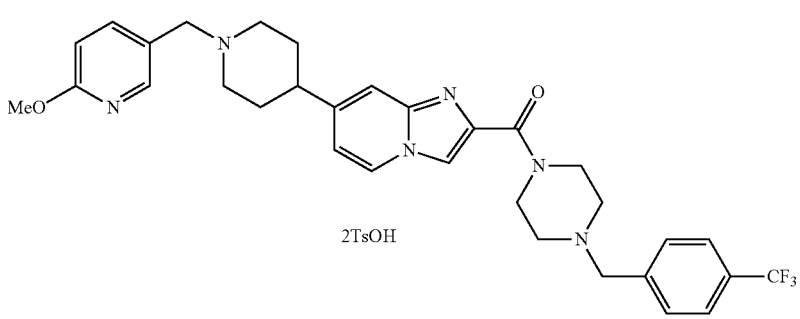 [SMILES: COc1ccc(CN2CCC(c3ccn4cc(C(=O)N5CCN(Cc6ccc(C(F)(F)F)cc6)CC5)nc4c3)CC2)cn1] 2TsOH |

TABLE 47
| Ex | Str |
|---|---|
| 37 | 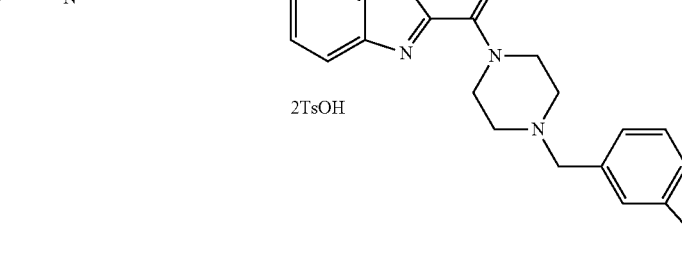 <br> 2TsOH |
| 38 | 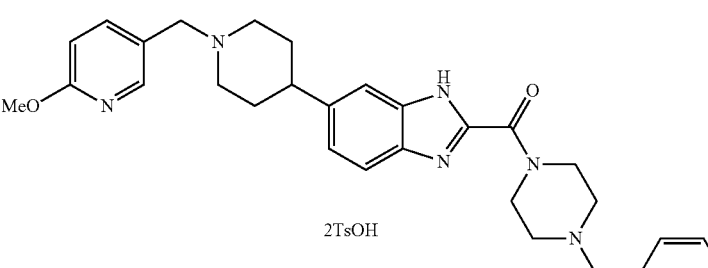 <br> 2TsOH |
| 39 | 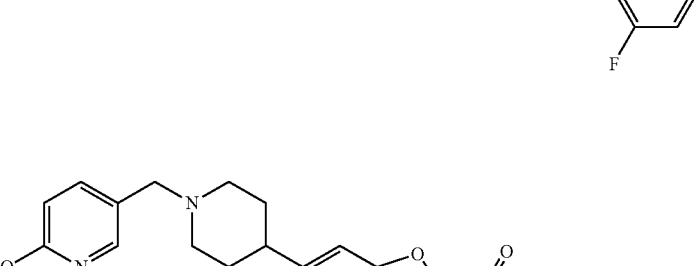 <br> 2TsOH |
| 40 | 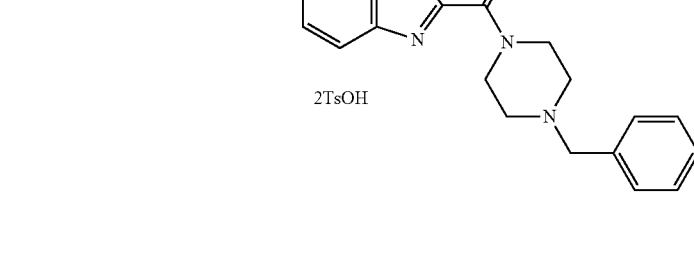 <br> 2TsOH |

TABLE 48
| Ex | Str |
|---|---|
| 41 | 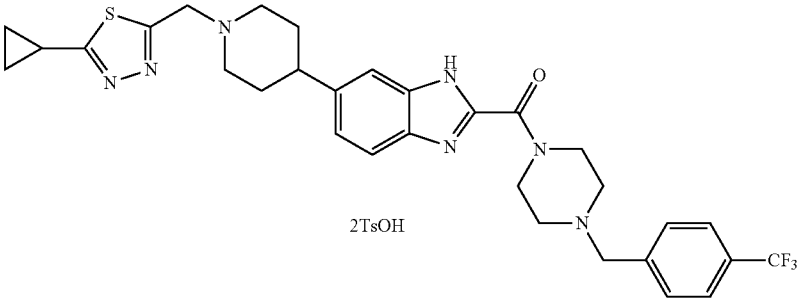 [SMILES: O=C(c1nc2ccc(C3CCN(Cc4nnc(C5CC5)s4)CC3)cc2[nH]1)N1CCN(Cc2ccc(C(F)(F)F)cc2)CC1]<br>2TsOH |
| 42 | 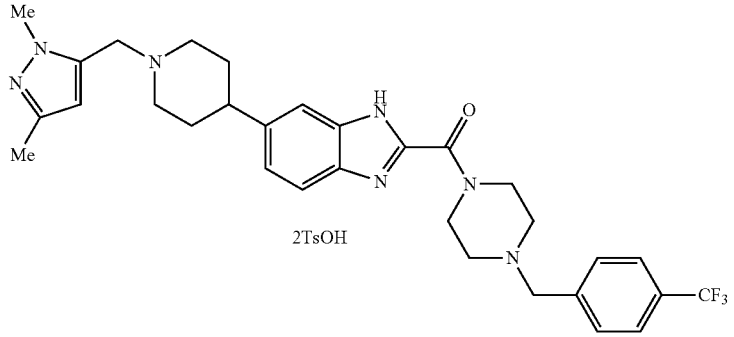 [SMILES: Cc1cc(CN2CCC(c3ccc4nc(C(=O)N5CCN(Cc6ccc(C(F)(F)F)cc6)CC5)[nH]c4c3)CC2)n(C)n1]<br>2TsOH |
| 43 | 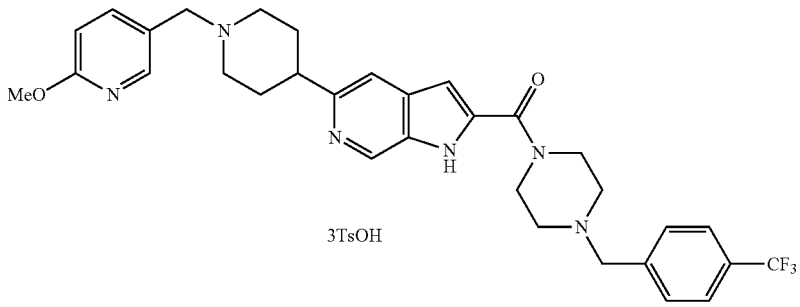 [SMILES: COc1ccc(CN2CCC(c3cc4cc(C(=O)N5CCN(Cc6ccc(C(F)(F)F)cc6)CC5)[nH]c4cn3)CC2)cn1]<br>3TsOH |
| 44 | 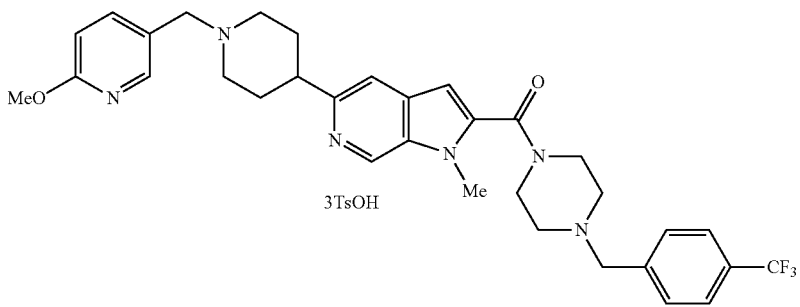 [SMILES: COc1ccc(CN2CCC(c3cc4cc(C(=O)N5CCN(Cc6ccc(C(F)(F)F)cc6)CC5)n(C)c4cn3)CC2)cn1]<br>3TsOH |

TABLE 49

| Ex | Str |
|---|---|
| 45 | (structure: 6-methoxypyridin-3-yl-CH2-piperidin-4-yl-[1-methylindole-2-carbonyl]-piperazine-CH2-(4-CHF2-phenyl); 2TsOH) |
| 46 | (structure: 5-methoxypyrazin-2-yl-CH2-piperidin-4-yl-[1-methylindole-2-carbonyl]-piperazine-CH2-(4-CHF2-phenyl); 2TsOH) |
| 47 | (structure: 5-methoxypyrazin-2-yl-CH2-piperidin-4-yl-[1-methylindole-2-carbonyl]-piperazine-CH2-(4-CHF2-phenyl); 2TsOH) |
| 48 | (structure: 6-methoxypyridin-3-yl-CH2-piperidin-4-yl-[1-methylindole-2-carbonyl]-piperazine-CH2-(4-CN-phenyl); 2TsOH) |

TABLE 50
| Ex | Str |
|---|---|
| 49 | 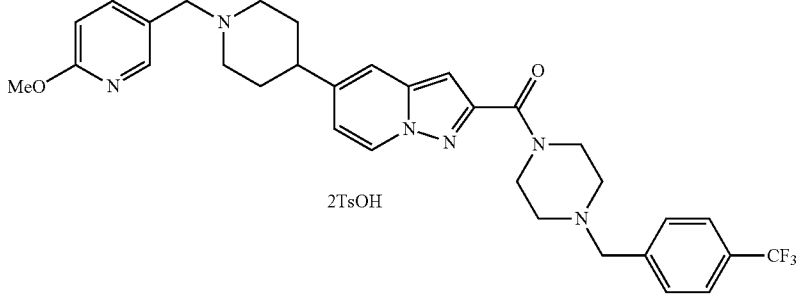 [SMILES: COc1ccc(CN2CCC(c3ccn4nc(C(=O)N5CCN(Cc6ccc(C(F)(F)F)cc6)CC5)cc4c3)CC2)cn1]<br>2TsOH |
| 50 | 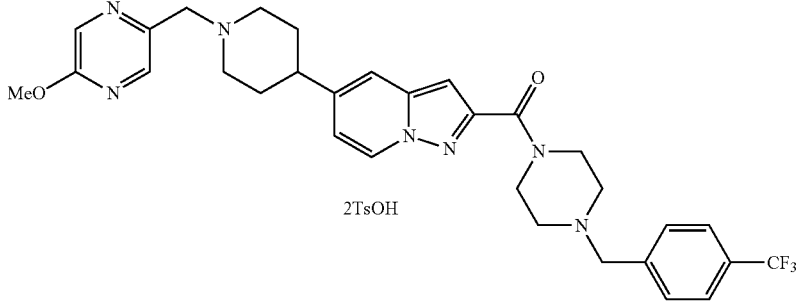 [SMILES: COc1cnc(CN2CCC(c3ccn4nc(C(=O)N5CCN(Cc6ccc(C(F)(F)F)cc6)CC5)cc4c3)CC2)cn1]<br>2TsOH |
| 51 | 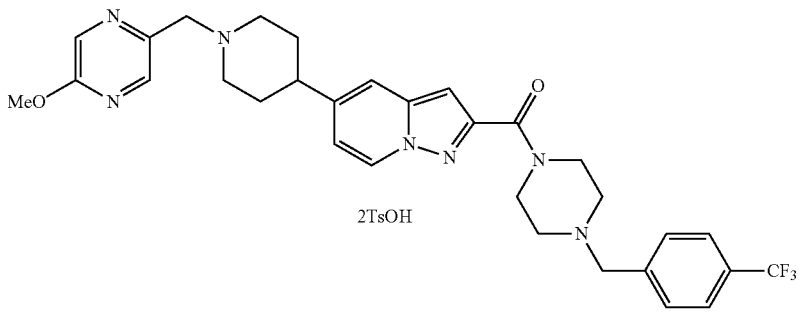 [SMILES: COc1cnc(CN2CCC(c3ccn4nc(C(=O)N5CCN(Cc6ccc(C(F)(F)F)cc6)CC5)cc4c3)CC2)cn1]<br>2TsOH |
| 52 | 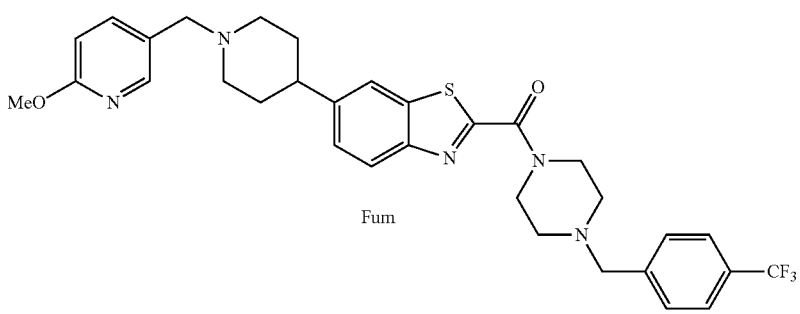 [SMILES: COc1ccc(CN2CCC(c3ccc4nc(C(=O)N5CCN(Cc6ccc(C(F)(F)F)cc6)CC5)sc4c3)CC2)cn1]<br>Fum |
| 53 | 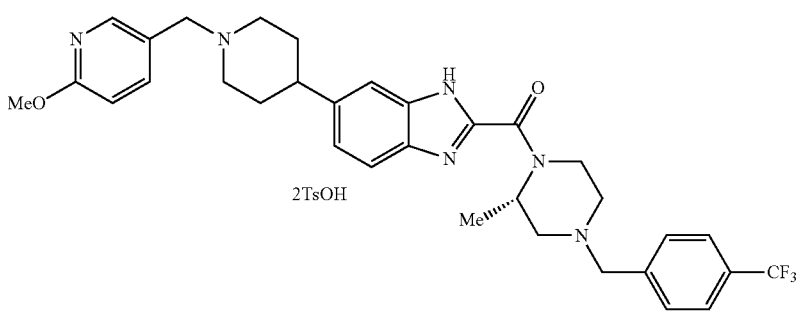 [SMILES: COc1ccc(CN2CCC(c3ccc4nc(C(=O)N5CCN(Cc6ccc(C(F)(F)F)cc6)C[C@@H]5C)[nH]c4c3)CC2)cn1]<br>2TsOH |

TABLE 51
| Ex | Str |
|---|---|
| 54 | 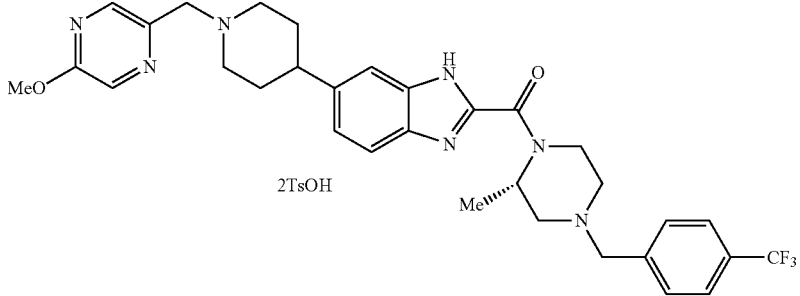 [SMILES: COc1cnc(CN2CCC(c3ccc4nc(C(=O)N5CCN(Cc6ccc(C(F)(F)F)cc6)C[C@@H]5C)[nH]c4c3)CC2)cn1] 2TsOH |
| 55 | 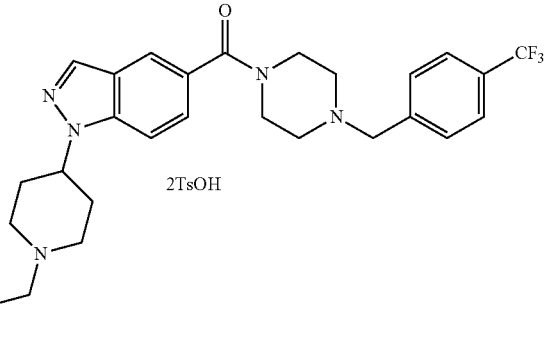 2TsOH |
| 56 | 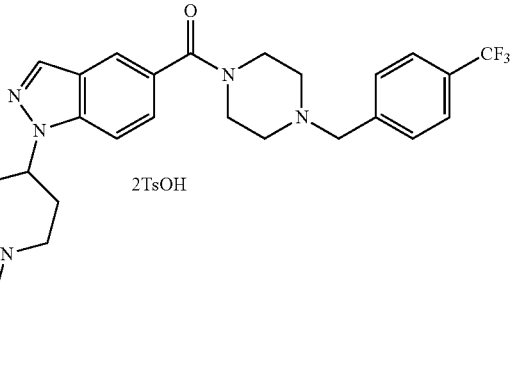 2TsOH |
| 57 | 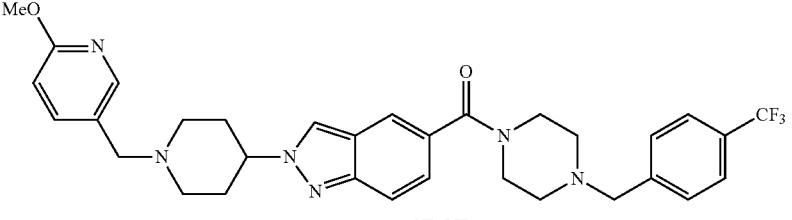 2TsOH |
| 58 | 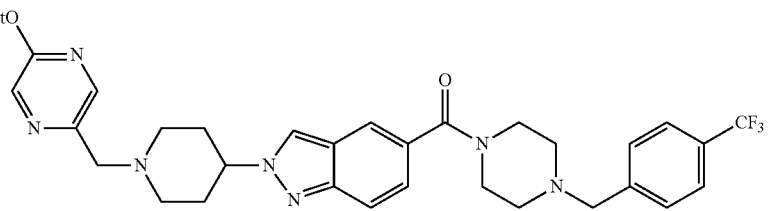 2TsOH |

TABLE 52
| Ex | Str |
|---|---|
| 59 | 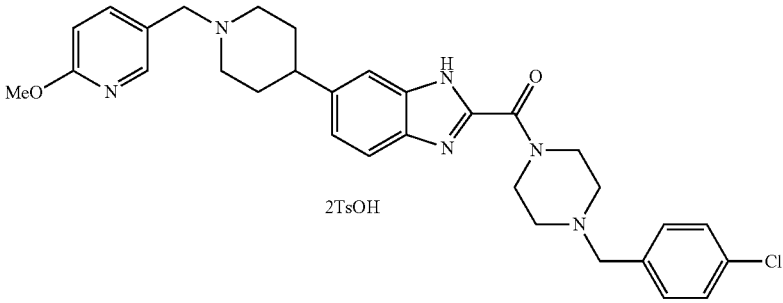 [SMILES: COc1ccc(CN2CCC(c3ccc4nc(C(=O)N5CCN(Cc6ccc(Cl)cc6)CC5)[nH]c4c3)CC2)cn1]<br>2TsOH |
| 60 | 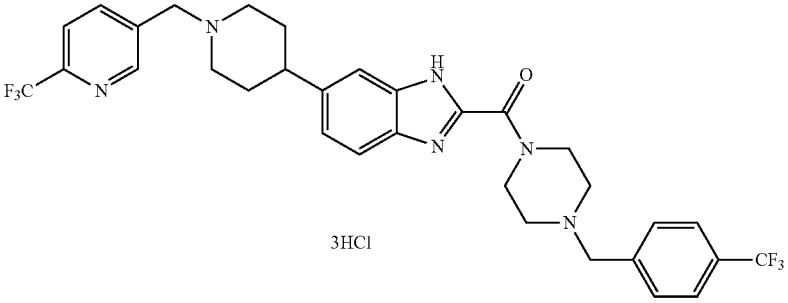 [SMILES: O=C(c1nc2ccc(C3CCN(Cc4ccc(C(F)(F)F)nc4)CC3)cc2[nH]1)N1CCN(Cc2ccc(C(F)(F)F)cc2)CC1]<br>3HCl |
| 61 | 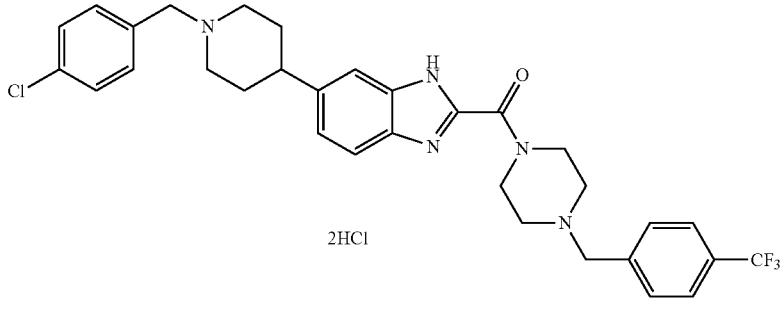 [SMILES: O=C(c1nc2ccc(C3CCN(Cc4ccc(Cl)cc4)CC3)cc2[nH]1)N1CCN(Cc2ccc(C(F)(F)F)cc2)CC1]<br>2HCl |
| 62 | 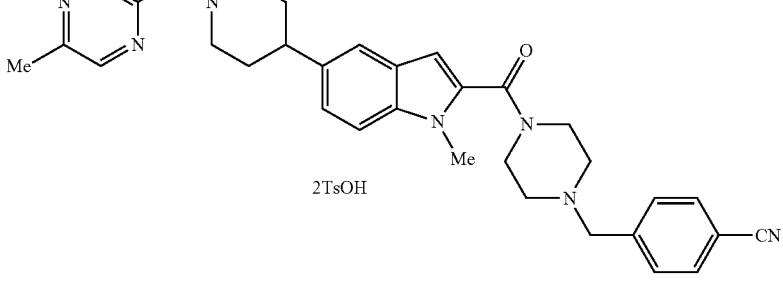<br>2TsOH |
| 63 | 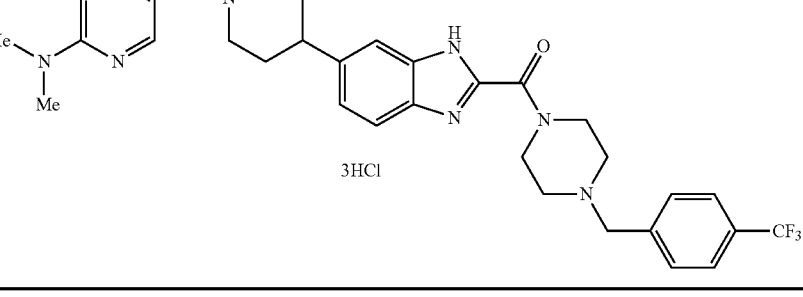<br>3HCl |

TABLE 53
| Ex | Str |
|---|---|
| 64 | 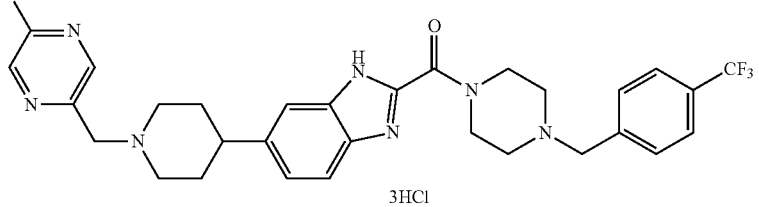 3HCl |
| 65 | 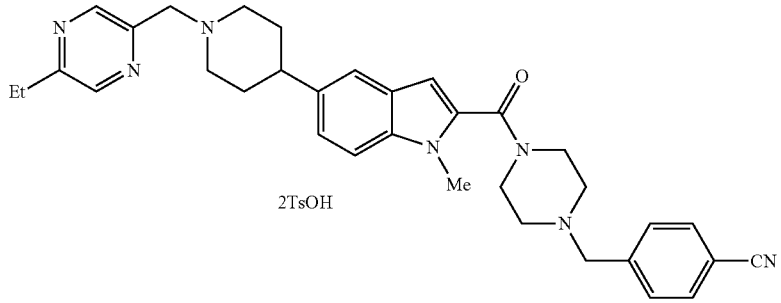 [SMILES: CCc1cnc(CN2CCC(c3ccc4c(c3)cc(C(=O)N3CCN(Cc5ccc(C#N)cc5)CC3)n4C)CC2)cn1] 2TsOH |
| 66 | 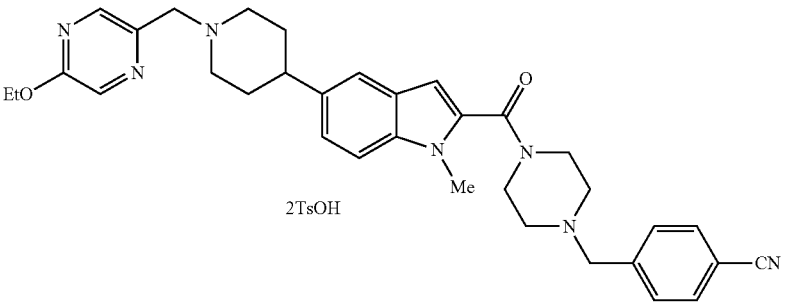 [SMILES: CCOc1cnc(CN2CCC(c3ccc4c(c3)cc(C(=O)N3CCN(Cc5ccc(C#N)cc5)CC3)n4C)CC2)cn1] 2TsOH |
| 67 | 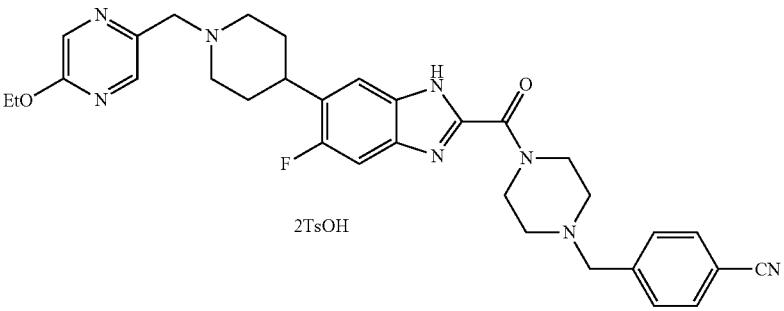 [SMILES: CCOc1cnc(CN2CCC(c3cc4[nH]c(C(=O)N5CCN(Cc6ccc(C#N)cc6)CC5)nc4cc3F)CC2)cn1] 2TsOH |
| 68 | 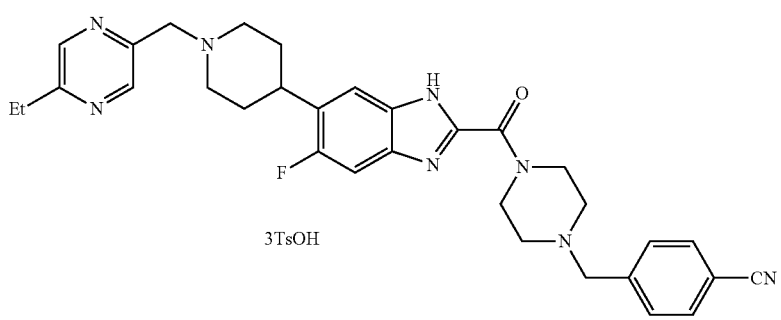 [SMILES: CCc1cnc(CN2CCC(c3cc4[nH]c(C(=O)N5CCN(Cc6ccc(C#N)cc6)CC5)nc4cc3F)CC2)cn1] 3TsOH |

TABLE 54

| Ex | Str |
|---|---|
| 69 | (structure: 5-ethoxypyrazin-2-yl-CH2-N-piperidine-4-yl bonded to 1-methyl-indole-6-yl; indole-2-carbonyl-piperazine-N-CH2-(4-cyanophenyl); 2TsOH) |
| 70 | (structure: 2-ethylpyrimidin-5-yl-CH2-N-piperidine-4-yl bonded to 1H-benzimidazol-6-yl; benzimidazole-2-carbonyl-piperazine-N-CH2-(4-CF3-phenyl); 2TsOH) |
| 71 | (structure: 6-methoxypyridin-3-yl-CH2-N-piperidine-4-yl bonded to 1H-benzimidazol-6-yl; benzimidazole-2-carbonyl-piperazine-N-CH2-(4-OMe-phenyl); 2TsOH) |
| 72 | (structure: 6-methoxypyridin-3-yl-CH2-N-piperidine-4-yl bonded to 1H-benzimidazol-6-yl; benzimidazole-2-carbonyl-piperazine-N-CH2-(4-OiPr-phenyl); 2TsOH) |
| 73 | (structure: 6-methoxypyridin-3-yl-CH2-N-piperidine-4-yl bonded to 1H-benzimidazol-6-yl; benzimidazole-2-carbonyl-piperazine-N-CH2-(4-OCF3-phenyl); 2TsOH) |

TABLE 55
| Ex | Str |
|---|---|
| 74 | 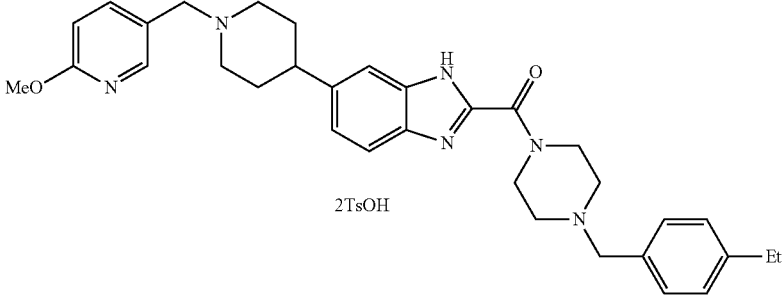 [SMILES: CCc1ccc(CN2CCN(C(=O)c3nc4ccc(C5CCN(Cc6ccc(OC)nc6)CC5)cc4[nH]3)CC2)cc1] |
| 75 | 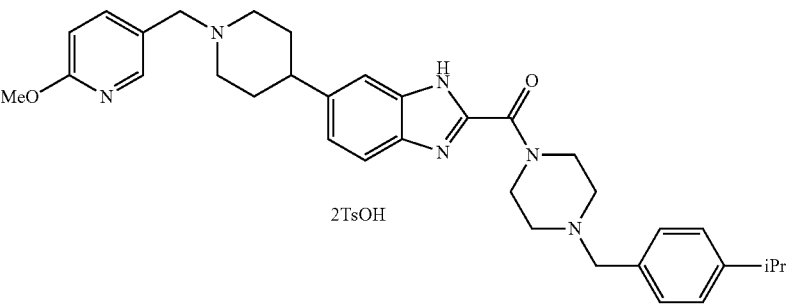 [SMILES: COc1ccc(CN2CCC(c3ccc4nc(C(=O)N5CCN(Cc6ccc(C(C)C)cc6)CC5)[nH]c4c3)CC2)cn1] |
| 76 | 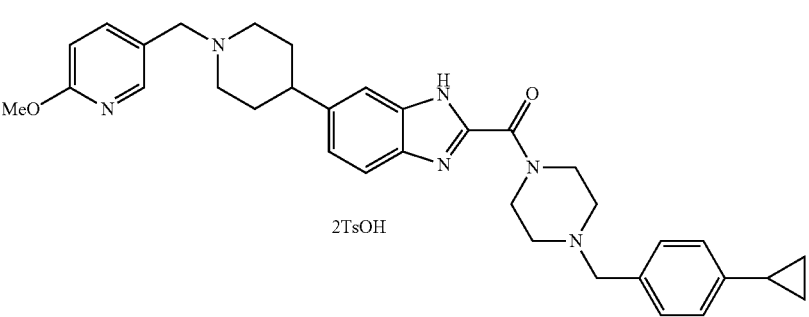 [SMILES: COc1ccc(CN2CCC(c3ccc4nc(C(=O)N5CCN(Cc6ccc(C7CC7)cc6)CC5)[nH]c4c3)CC2)cn1] |
| 77 | 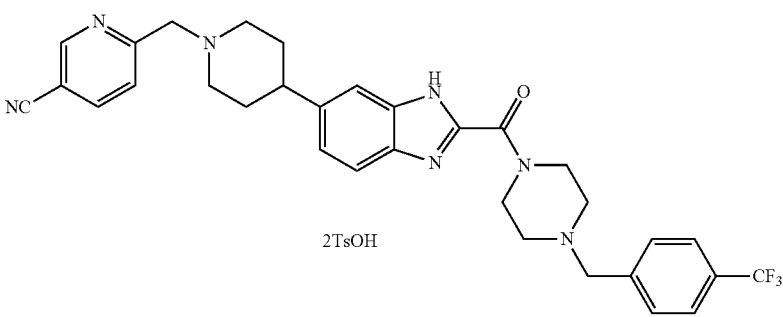 [SMILES: N#Cc1ccc(CN2CCC(c3ccc4nc(C(=O)N5CCN(Cc6ccc(C(F)(F)F)cc6)CC5)[nH]c4c3)CC2)nc1] |
| 78 | 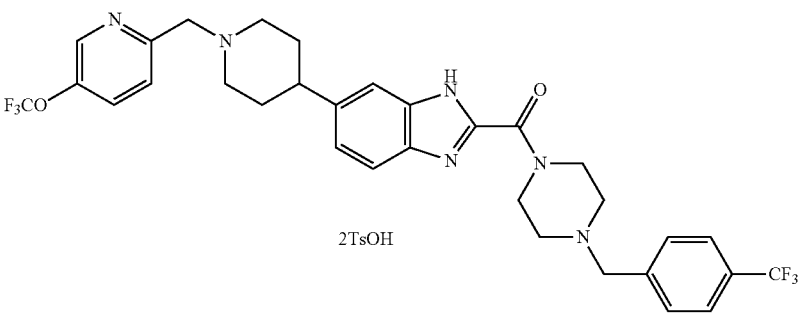 [SMILES: O=C(c1nc2ccc(C3CCN(Cc4ccc(OC(F)(F)F)cn4)CC3)cc2[nH]1)N1CCN(Cc2ccc(C(F)(F)F)cc2)CC1] |

TABLE 56

| Ex | Str |
|---|---|
| 79 | 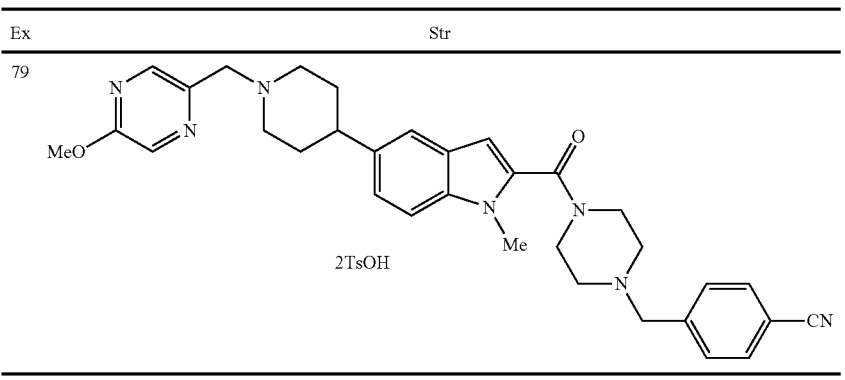 2TsOH |

TABLE 57

| Ex | Syn | Dat |
|---|---|---|
| 1 | E1 | ESI+: 593;<br>NMR1: 1.98-2.21 (4H, m), 2.38 (6H, s), 2.99-3.09 (1H, m), 3.12-3.27 (2H, m), 3.27-3.58 (8H, m), 3.59-3.68 (2H, m), 3.95 (3H, s), 4.36 (2H, s), 4.39-4.51 (2H, m), 6.86-6.92 (1H, m), 7.19-7.24 (4H, m), 7.25-7.30 (1H, m), 7.54-7.65 (2H, m), 7.68-7.83 (8H, m), 7.85 (1H, dd, J = 2.8, 8.4 Hz), 8.31 (1H, d, J = 2.0 Hz);<br>2θ (°) = 6.5, 10.1, 15.2, 16.2, 18.6, 19.6, 20.1, 20.8, 23.3, 25.8 |
| 2 | E2 | ESI+: 592 |
| 3 | E3 | ESI+: 592 |
| 4 | E4 | ESI+: 591 |
| 5 | E5 | ESI+: 592 |
| 6 | E6 | ESI+: 610 |
| 7 | E7 | ESI+: 594;<br>NMR1: 2.01-2.22 (4H, m), 2.35 (6H, s), 3.01-3.11 (1H, m), 3.20-3.80 (12H, m), 4.02 (3H, s), 4.47 (2H, s), 4.52 (2H, s), 7.18-7.25 (4H, m), 7.31 (1H, dd, J = 1.6, 8.6 Hz), 7.55-7.59 (1H, m), 7.64 (1H, d, J = 8.5 Hz), 7.67-7.73 (4H, m), 7.75-7.78 (2H, m), 7.78-7.84 (2H, m), 8.31-8.35 (2H, m);<br>2θ (°) = 6.2, 6.7, 13.3, 15.2, 16.4, 19.0, 20.5, 20.9, 22.6, 24.8 |
| 8 | E8 | ESI+: 578;<br>NMR1: 2.06-2.29 (4H, m), 2.62 (3H, m), 3.06-3.95 (13H, m), 4.54 (2H, s), 4.57 (2H, s), 7.40 (1H, dd, J = 1.6, 8.6 Hz), 7.59-7.65 (1H, m), 7.70 (1H, d, J = 8.6 Hz), 7.78-7.88 (4H, m), 8.62-8.71 (2H, m) |
| 9 | E1 | ESI+: 593 |
| 10 | E1 | ESI+: 594 |
| 11 | E3 | ESI+: 593 |
| 12 | E1 | ESI+: 605 |
| 13 | E3 | ESI+: 604 |
| 14 | E3 | ESI+: 592;<br>NMR1: 2.01-2.22 (4H, m), 3.03-3.23 (3H, m), 3.26-3.70 (10H, m), 3.84 (3H, s), 4.31 (2H, s), 4.52-4.57 (2H, m), 7.03-7.07 (2H, m), 7.38 (1H, dd, J = 1.6, 8.8 Hz), 7.48-7.52 (2H, m), 7.59-7.63 (1H, m), 7.69 (1H, d, J = 8.4 Hz), 7.80-7.86 (4H, m) |
| 15 | E1 | ESI+: 592 |

TABLE 58

| Ex | Syn | Dat |
|---|---|---|
| 16 | E3 | ESI+: 591 |
| 17 | E1 | ESI+: 606 |
| 18 | E1 | ESI+: 607;<br>NMR1: 2.00-2.23 (4H, m), 2.36 (6H, s), 3.03-3.14 (1H, m), 3.15-3.26 (2H, m), 3.27-3.78 (10H, m), 3.95 (3H, s), 3.96 (3H, s), 4.36 (2H, s), 4.48 (2H, s), 6.88-6.93 (1H, m), 7.19-7.25 (4H, m), 7.28 (1H, dd, J = 1.5, 8.6 Hz), 7.49-7.54 (1H, m), 7.65-7.83 (9H, m), 7.85 (1H, dd, J = 2.5, 8.7 Hz), 8.31 (1H, d, J = 2.4 Hz) |

TABLE 58-continued

| Ex | Syn | Dat |
|---|---|---|
| 19 | E1 | ESI+: 607;<br>NMR1: 1.95-2.21 (4H, m), 2.36 (6H, s), 3.00-3.11 (1H, m), 3.14-3.25 (2H, m), 3.25-3.74 (10H, m), 3.93-3.98 (6H, m), 4.35 (2H, s), 4.52 (2H, s), 6.89-6.93 (1H, m), 7.19-7.25 (4H, m), 7.38 (1H, dd, J = 1.4, 8.7 Hz), 7.58-7.63 (2H, m), 7.67-7.73 (4H, m), 7.73-7.83 (4H, m), 7.85 (1H, dd, J = 2.5, 8.7 Hz), 8.31 (1H, d, J = 2.4 Hz) |
| 20 | E1 | ESI+: 591 |
| 21 | E1 | ESI+: 575 |
| 22 | E3 | ESI+: 577 |
| 23 | E1 | ESI+: 550;<br>NMR1: 1.96-2.11 (2H, m), 2.11-2.20 (2H, m), 2.35 (6H, s), 2.99-3.10 (1H, m), 3.11-3.25 (2H, m), 3.30-3.74 (10H, m), 3.96 (3H, s), 4.35 (2H, s), 4.50 (2H, s), 6.88-6.93 (1H, m), 7.17-7.25 (4H, m), 7.29 (1H, dd, J = 1.6, 8.6 Hz), 7.53-7.58 (1H, m), 7.63 (1H, d, J = 8.6 Hz), 7.67-7.77 (6H, m), 7.81-7.90 (3H, m), 8.31 (1H, d, J = 2.2 Hz) |
| 24 | E1 | ESI+: 611 |
| 25 | E1 | ESI+: 592 |
| 26 | E1 | ESI+: 611 |
| 27 | E1 | ESI+: 611 |
| 28 | E1 | ESI+: 594 |
| 29 | E1 | ESI+: 594 |
| 30 | E1 | ESI+: 594 |
| 31 | E1 | ESI+: 606 |
| 32 | E5 | ESI+: 606 |
| 33 | E1 | ESI+: 606 |
| 34 | E1 | ESI+: 620 |

TABLE 59

| Ex | Syn | Dat |
|---|---|---|
| 35 | E1 | ESI+: 593;<br>NMR1: 1.94-2.08 (2H, m), 2.14-2.22 (2H, m), 2.35 (6H, s), 2.92-3.03 (1H, m), 3.07-3.51 (10H, m), 3.58-3.68 (2H, m), 3.95 (3H, s), 4.35 (2H, s), 4.41 (2H, s), 6.86-6.91 (1H, m), 7.20-7.24 (4H, m), 7.37-7.42 (1H, m), 7.57 (1H, d, J = 9.6 Hz), 7.67-7.81 (8H, m), 7.84 (1H, dd, J = 2.4, 8.8 Hz), 8.26-8.34 (2H, m), 8.41 (1H, s) |
| 36 | E36 | ESI+: 593;<br>NMR1: 1.93-2.07 (2H, m), 2.18-2.26 (2H, m), 2.36 (6H, s), 3.00-3.09 (1H, m), 3.11-3.52 (10H, m), 3.62-3.68 (2H, m), 3.95 (3H, s), 4.36 (2H, s), 4.47 (2H, s), 6.88-6.91 (1H, m), 7.03-7.07 (1H, m), 7.21-7.25 (4H, m), 7.46-7.51 (1H, m), 7.67-7.86 (9H, m), 8.29-8.34 (2H, m), 8.49 (1H, d, J = 7.2 Hz) |
| 37 | E1 | ESI+: 605;<br>NMR1: 1.96-2.11 (2H, m), 2.12-2.23 (2H, m), 2.35 (6H, s), 2.98-3.10 (1H, m), 3.14-3.25 (2H, m), 3.25-3.80 (10H, m), 3.96 (3H, s), 4.35 (2H, s), 4.44 (2H, s), 6.88-6.93 (1H, m), 7.18-7.25 (4H, m), 7.27 (1H, dd, J = 1.5, 8.5 Hz), 7.31-7.39 (2H, m), 7.44 (1H, dd, J = 1.5 Hz), |

TABLE 59-continued

| Ex | Syn | Dat |
|---|---|---|
| | | 7.52-7.57 (1H, m), 7.62 (1H, d, J = 8.5 Hz), 7.67-7.74 (4H, m), 7.85 (1H, dd, J = 2.5, 8.7 Hz), 8.31 (1H, d, J = 2.2 Hz) |
| 38 | E1 | ESI+: 611; NMR1: 1.98-2.21 (4H, m), 2.35 (6H, s), 2.99-3.10 (1H, m), 3.14-3.25 (2H, m), 3.25-3.75 (10H, m), 3.96 (3H, s), 4.35 (2H, s), 4.59 (2H, s), 6.89-6.94 (1H, m), 7.18-7.25 (4H, m), 7.30 (1H, dd, J = 1.6, 8.6 Hz), 7.55-7.59 (1H, m), 7.61-7.75 (7H, m), 7.82-7.91 (2H, m), 8.32 (1H, d, J = 2.3 Hz) |
| 39 | E1 | ESI+: 594 |
| 40 | E1 | ESI+: 594 |
| 41 | E7 | ESI+: 610 |
| 42 | E1 | ESI+: 580 |
| 43 | E1 | ESI+: 593 |

TABLE 60

| Ex | Syn | Dat |
|---|---|---|
| 44 | E1 | ESI+: 607; NMR1: 2.15-2.37 (4H, m), 2.36 (9H, s), 3.17-3.62 (11H, m), 3.63-3.73 (2H, m), 3.95 (3H, s), 4.04 (3H, s), 4.37 (2H, s), 4.48 (2H, s), 6.87 (1H, d, J = 8.6 Hz), 7.16 (1H, s), 7.20-7.25 (6H, m), 7.66-7.79 (10H, m), 7.85 (1H, dd, J = 2.5, 8.6 Hz), 8.11 (1H, s), 8.31 (1H, d, J = 2.5 Hz), 9.23 (1H, s) |
| 45 | E1 | ESI+: 588 |
| 46 | E7 | ESI+: 589 |
| 47 | E7 | ESI+: 573 |
| 48 | E1 | ESI+: 563 |
| 49 | E1 | ESI+: 593; NMR1: 1.91-2.06 (2H, m), 2.06-2.25 (2H, m), 2.36 (6H, s), 2.91-3.04 (1H, m), 3.11-3.72 (12H, m), 3.95 (3H, s), 4.35 (2H, s), 4.47 (2H, s), 6.86-6.98 (3H, m), 7.19-7.25 (4H, m), 7.53-7.57 (1H, m), 7.67-7.82 (8H, m), 7.84 (1H, dd, J = 2.5, 8.7 Hz), 8.30 (1H, d, J = 2.4 Hz), 8.50 (1H, d, J = 7.3 Hz) |
| 50 | E7 | ESI+: 594; NMR1: 1.94-2.09 (2H, m), 2.09-2.25 (2H, m), 2.36 (6H, s), 2.94-3.09 (1H, m), 3.09-3.84 (12H, m), 4.02 (3H, s), 4.34-4.58 (4H, m), 6.89-6.99 (2H, m), 7.18-7.27 (4H, m), 7.53-7.60 (1H, m), 7.66-7.86 (8H, m), 8.29-8.37 (2H, m), 8.51 (1H, d, J = 7.3 Hz) |
| 51 | E7 | ESI+: 578 |
| 52 | E5 | ESI+: 610 |
| 53 | E1 | ESI+: 607 |
| 54 | E7 | ESI+: 608 |
| 55 | P21, E1 | ESI+: 593 |
| 56 | P21, E7 | ESI+: 608 |
| 57 | P21, E1 | ESI+: 593; NMR1: 2.36 (6H, s), 2.40-2.58 (4H, m), 3.19-3.77 (12H, m), 3.98 (3H, s), 4.34-4.57 (4H, m), 4.86-4.97 (1H, m), 6.93-7.01 (1H, m), 7.19-7.26 (4H, m), 7.34-7.42 (1H, m), 7.66-7.81 (9H, m), 7.89-7.99 (2H, m), 8.35 (1H, d, J = 2.3 Hz), 8.46 (1H, s) |

TABLE 61

| Ex | Syn | Dat |
|---|---|---|
| 58 | P21, E7 | ESI+: 608; NMR1: 1.42 (3H, t, J = 7.1 Hz), 2.36 (6H, s), 2.39-2.73 (4H, m), 3.18-3.85 (12H, m), 4.41-4.53 (6H, m), 4.87-4.98 (1H, m), 7.19-7.25 (4H, m), 7.36-7.44 (1H, m), 7.67-7.81 (9H, m), 7.92-7.98 (1H, m), 8.28-8.33 (2H, m), 8.43-8.57 (1H, m) |
| 59 | E59 | ESI+: 559 |
| 60 | E3 | ESI+: 631 |
| 61 | E3 | ESI+: 596 |
| 62 | E7 | ESI+: 548 |
| 63 | E3 | ESI+: 606 |
| 64 | E8 | ESI+: 592 |

TABLE 61-continued

| Ex | Syn | Dat |
|---|---|---|
| 65 | E7 | ESI+: 562 |
| 66 | E7 | ESI+: 578 NMR2: 1.38 (3H, t, J = 7.1 Hz), 1.85-2.06 (4H, m), 2.29 (6H, s), 2.83-2.95 (1H, m), 3.06-3.70 (12H, m), 3.76 (3H, s), 4.34-4.67 (4H, m), 4.41 (2H, q, J = 7.1 Hz), 6.61-6.82 (1H, m), 7.06-7.13 (4H, m), 7.13-7.18 (1H, m), 7.38-7.43 (1H, m), 7.44-7.55 (5H, m), 7.61-7.80 (2H, m), 7.85-8.09 (2H, m), 8.39 (1H, d, J = 1.3 Hz), 8.42 (1H, d, J = 1.3 Hz), 9.66- 9.79 (1H, m), 9.86-10.19 (1H, m) |
| 67 | E7 | ESI+: 583 |
| 68 | E7 | ESI+: 567 |
| 69 | E7 | ESI+: 578 NMR2: 1.38 (3H, t, J = 7.0 Hz), 1.89-2.10 (4H, m), 2.29 (6H, s), 2.88-3.00 (1H, m), 3.02-3.69 (12H, m), 3.76 (3H, s), 4.26-4.63 (4H, m), 4.41 (2H, q, J = 7.1 Hz), 6.61-6.79 (1H, m), 6.96-7.03 (1H, m), 7.06-7.14 (4H, m), 7.32 (1H, s), 7.44-7.51 (4H, m), 7.57 (1H, d, J = 8.3 Hz), 7.62-7.81 (2H, m), 7.85-8.10 (2H, m), 8.39 (1H, d, J = 1.2 Hz), 8.42 (1H, d, J = 1.2 Hz), 9.67-9.81 (1H, m), 9.89-10.16 (1H, m); 2θ (°) = 3.6, 7.2, 10.9, 16.1, 16.7, 17.2, 19.2, 20.9, 22.8, 26.6 |
| 70 | E7 | ESI+: 592 |
| 71 | E59 | ESI+: 555 |
| 72 | E59 | ESI+: 583 |
| 73 | E59 | ESI+: 609 |
| 74 | E59 | ESI+: 553 |
| 75 | E59 | ESI+: 567 |

TABLE 62

| Ex | Syn | Dat |
|---|---|---|
| 76 | E59 | ESI+: 565 |
| 77 | E1 | ESI+: 588 |
| 78 | E7 | ESI+: 647 |
| 79 | E7 | ESI+: 564 NMR2: 1.84-2.07 (4H, m), 2.29 (6H, s), 2.82-2.94 (1H, m), 3.08-3.68 (12H, m), 3.75 (3H, s), 3.97 (3H, s), 4.21-4.66 (4H, m), 6.57-6.80 (1H, m), 7.06-7.13 (4H, m), 7.12-7.19 (1H, m), 7.37-7.43 (1H, m), 7.44-7.54 (5H, m), 7.58-7.79 (2H, m), 7.84-8.10 (2H, m), 8.41 (1H, d, J = 1.2 Hz), 8.46 (1H, d, J = 1.3 Hz), 9.64-9.83 (1H, m), 9.87-10.16 (1H, m); 2θ (°) = 7.5, 9.8, 13.2, 14.7, 15.6, 16.9, 18.8, 19.5, 20.0, 22.6 |

INDUSTRIAL APPLICABILITY

The compound of the formula (I) or a salt thereof of the present invention has an excellent Complex I inhibitory effect and AMPK activation effect, and can be used as an agent for treating breast cancer, in particular, breast cancer in which the MCT4 is not expressed, and among others, PIK3CA mutation-positive breast cancer in which the MCT4 is not expressed.

The invention claimed is:

1. A compound of the formula (I) or a salt thereof:

wherein R¹ is aryl or monocyclic nitrogen-containing heteroaryl, each of which is optionally substituted with at least one substituent selected from the group consisting of halogen, lower alkyl, —O-lower alkyl, halogeno-lower alkyl, —O-halogeno-lower alkyl, —CN, dimethylamino, and cycloalkyl;

wherein X is CH, N, or C;

is a single bond if X is CH or N or is a double bond if X is C;

Y is a cyclic group of any of formulae Y-1 to Y-11:

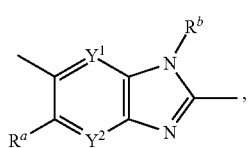 (Y-1)

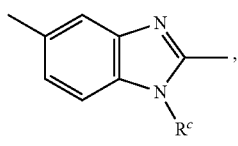 (Y-2)

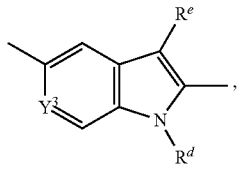 (Y-3)

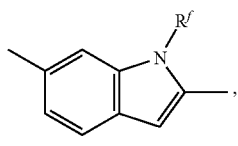 (Y-4)

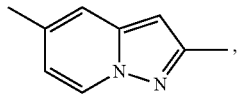 (Y-5)

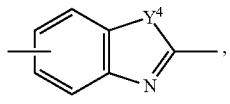 (Y-6)

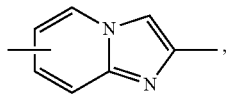 (Y-7)

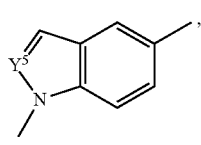 (Y-8)

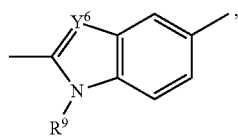 (Y-9)

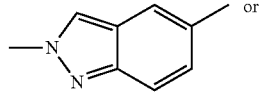 (Y-10)

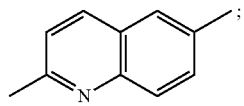 (Y-11)

$Y^1$ is $CR^h$ or N;
$Y^2$ is $CR^i$ or N;
$Y^1$ and $Y^2$ are not both N;
$R^a$, $R^b$, and $R^i$ are each independently H or halogen;
$R^b$ is H or lower alkyl;
$R^c$ is lower alkyl;
$Y^3$ is CH or N;
$R^d$ and $R^e$ are each independently H or lower alkyl;
$R^f$ is H or lower alkyl;
$Y^4$ is O or S;
$Y^5$ is CH or N;
$Y^6$ is CH or N;
$R^g$ is H or lower alkyl;
$R^2$ is H or lower alkyl; and
either
$R^3$ and $R^4$ are each independently H, halogen, lower alkyl, —O-lower alkyl, halogeno-lower alkyl, —O-halogeno-lower alkyl, cycloalkyl, or —CN,
or
$R^3$ and $R^4$ form 2,2-difluoro-1,3-benzodioxole with the benzene ring to which $R^3$ and $R^4$ are bonded.

2. The compound or salt thereof according to claim 1, wherein $R^2$ is H.

3. The compound or salt thereof according to claim 2, wherein X is CH.

4. The compound or salt thereof according to claim 3, wherein Y is of any of formulae Y-1-A, Y-2, Y-3-A, Y-3-B, Y-4, Y-5, Y-6-A, Y-7-A, Y-7-B, or Y-10:

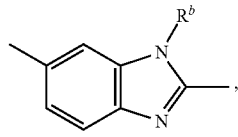 (Y-1-A)

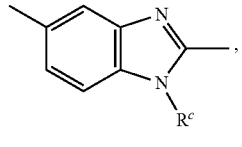 (Y-2)

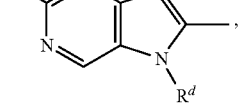 (Y-3-A)

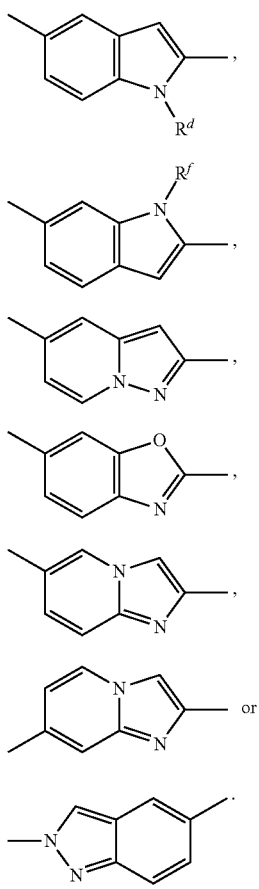

5. The compound or salt thereof according to claim 4, wherein $R^b$ is H or methyl, $R^c$ is methyl, $R^d$ is methyl, and $R^f$ is methyl.

6. The compound or salt thereof according to claim 5, wherein either
 $R^3$ is H or halogen and $R^4$ is halogeno-lower alkyl, —O-lower alkyl, or —CN,
 or
 $R^3$ and $R^4$ form 2,2-difluoro-1,3-benzodioxole with the benzene ring to which $R^3$ and $R^4$ are bonded.

7. The compound or salt thereof according to claim 6, wherein $R^1$ is phenyl, pyridyl, pyrazinyl, pyrimidinyl, or pyrazolyl, each of which is optionally substituted with at least one substituent selected from the group consisting of lower alkyl and —O-lower alkyl.

8. The compound or salt thereof according to claim 1, wherein the compound is selected from the group consisting of
 (5-{1-[(6-methoxypyridin-3-yl)methyl]piperidin-4-yl}-1H-benzimidazol-2-yl){4-[4-(trifluoromethyl)benzyl]piperazin-1-yl}methanone,
 (5-{1-[(5-methoxypyrazin-2-yl)methyl]piperidin-4-yl}-1H-benzimidazol-2-yl){4-[4-(trifluoromethyl)benzyl]piperazin-1-yl}methanone,
 (6-{1-[(5-methylpyrazin-2-yl)methyl]piperidin-4-yl}-1H-benzimidazol-2-yl){4-[4-(trifluoromethyl)benzyl]piperazin-1-yl}methanone,
 (7-{1-[(6-methoxypyridin-3-yl)methyl]piperidin-4-yl}imidazo[1,2-a]pyridin-2-yl){4-[4-(trifluoromethyl)benzyl]piperazin-1-yl}methanone,
 4-({4-[(5-{1-[(5-ethoxypyrazin-2-yl)methyl]piperidin-4-yl}-1-methyl-1H-indol-2-yl)carbonyl]piperazin-1-yl}methyl)benzonitrile,
 4-({4-[(6-{1-[(5-ethoxypyrazin-2-yl)methyl]piperidin-4-yl}-1-methyl-1H-indol-2-yl)carbonyl]piperazin-1-yl}methyl)benzonitrile, and
 4-({4-[(5-{1-[(5-methoxypyrazin-2-yl)methyl]piperidin-4-yl}-1-methyl-1H-indol-2-yl)carbonyl]piperazin-1-yl}methyl)benzonitrile.

9. A pharmaceutical composition, comprising a compound or salt thereof according to claim 8 and a pharmaceutically acceptable excipient.

10. The compound or salt thereof of claim 8, wherein the compound is (5-{1-[(6-methoxypyridin-3-yl)methyl]piperidin-4-yl}-1H-benzimidazol-2-yl){4-[4-(trifluoromethyl)benzyl]piperazin-1-yl}methanone.

11. The compound or salt thereof of claim 8, wherein the compound is (5-{1-[(5-methoxypyrazin-2-yl)methyl]piperidin-4-yl}-1H-benzimidazol-2-yl){4-[4-(trifluoromethyl)benzyl]piperazin-1-yl}methanone.

12. The compound or salt thereof of claim 8, wherein the compound is 4-({4-[(6-{1-[(5-ethoxypyrazin-2-yl)methyl]piperidin-4-yl}-1-methyl-1H-indol-2-yl)carbonyl]piperazin-1-yl}methyl)benzonitrile.

13. The compound or salt thereof of claim 8, wherein the compound is 4-({4-[(5-{1-[(5-methoxypyrazin-2-yl)methyl]piperidin-4-yl}-1-methyl-1H-indol-2-yl)carbonyl]piperazin-1-yl}methyl)benzonitrile.

14. A method for treating breast cancer, the method comprising administering to a subject in need thereof an effective amount of a compound or salt thereof according to claim 8.

15. The method according to claim 14, wherein said breast cancer is breast cancer in which MCT4 is not expressed.

16. The method according to claim 14, wherein said breast cancer is PIK3CA mutation-positive breast cancer in which MCT4 is not expressed.

17. The compound or a salt thereof according to claim 8, wherein the compound is
 (5-{1-[(6-methoxypyridin-3-yl)methyl]piperidin-4-yl}-1H-benzimidazol-2-yl){4-[4-(trifluoromethyl)benzyl]piperazin-1-yl}methanone ditosylate.

18. The compound or a salt thereof according to claim 8, wherein the compound is
 (5-{1-[(5-methoxypyrazin-2-yl)methyl]piperidin-4-yl}-1H-benzimidazol-2-yl){4-[4-(trifluoromethyl)benzyl]piperazin-1-yl}methanone ditosylate.

19. The compound or a salt thereof according to claim 8, wherein the compound is
 4-({4-[(6-{1-[(5-ethoxypyrazin-2-yl)methyl]piperidin-4-yl}-1-methyl-1H-indol-2-yl)carbonyl]piperazin-1-yl}methyl)benzonitrile ditosylate.

20. The compound or a salt thereof according to claim 8, wherein the compound is
 4-({4-[(5-{1-[(5-methoxypyrazin-2-yl)methyl]piperidin-4-yl}-1-methyl-1H-indol-2-yl)carbonyl]piperazin-1-yl}methyl)benzonitrile ditosylate.

* * * * *